(12) United States Patent
Chou et al.

(10) Patent No.: US 10,612,055 B2
(45) Date of Patent: Apr. 7, 2020

(54) CONTROL OF BIOFILM DISPERSAL FOR THE PRODUCTION OF AMINO ACIDS OR AMINO ACID-DERIVED PRODUCTS

(71) Applicants: CATHAY BIOTECH INC., Shanghai (CN); CIBT AMERICA INC., Newark, DE (US)

(72) Inventors: Howard Chou, Shanghai (CN); Xiucai Liu, Shanghai (CN)

(73) Assignees: Cathay Biotec Inc., Shanghai (CN); CIBT America Inc., Newark, DE (US)

( * ) Notice: Subject to any disclaimer, the term of this patent is extended or adjusted under 35 U.S.C. 154(b) by 0 days.

(21) Appl. No.: 16/325,610

(22) PCT Filed: Aug. 15, 2016

(86) PCT No.: PCT/CN2016/095281
§ 371 (c)(1),
(2) Date: Feb. 14, 2019

(87) PCT Pub. No.: WO2018/032240
PCT Pub. Date: Feb. 22, 2018

(65) Prior Publication Data
US 2019/0194705 A1 Jun. 27, 2019

(51) Int. Cl.
| | |
|---|---|
| *C12N 9/88* | (2006.01) |
| *C12P 13/08* | (2006.01) |
| *C12N 15/52* | (2006.01) |
| *C12P 13/00* | (2006.01) |
| *C07K 14/195* | (2006.01) |
| *C12N 1/20* | (2006.01) |
| *C12N 15/70* | (2006.01) |
| *C12N 15/74* | (2006.01) |
| *C12R 1/15* | (2006.01) |
| *C12R 1/19* | (2006.01) |

(52) U.S. Cl.
CPC ............ *C12P 13/08* (2013.01); *C07K 14/195* (2013.01); *C12N 1/20* (2013.01); *C12N 9/88* (2013.01); *C12N 15/52* (2013.01); *C12N 15/70* (2013.01); *C12N 15/74* (2013.01); *C12P 13/001* (2013.01); *C12R 1/15* (2013.01); *C12R 1/19* (2013.01); *C12N 2510/02* (2013.01); *C12Y 401/01018* (2013.01)

(58) Field of Classification Search
CPC ........... C12N 15/52; C12N 1/20; C12P 13/08; C07K 14/195

USPC ....................................................... 425/252.3
See application file for complete search history.

(56) References Cited

FOREIGN PATENT DOCUMENTS

| CN | 101240258 A | 8/2008 |
|---|---|---|
| CN | 105624175 A | 6/2016 |
| WO | 2015109265 A1 | 7/2015 |
| WO | 2016054792 A1 | 4/2016 |

OTHER PUBLICATIONS

Valentini et al. The Journal of Biological Chemistry vol. 291, No. 24, pp. 12547-12555, (2016) (Year: 2016).*
International Search Report and Written Opinion issued in Application No. PCT/CN2016/095281 dated Apr. 26, 2017, 10 pages.
Ma, Q. et al., "Engineering a novel c-di-GMP-binding protein for biofilm dispersal", Environmental Microbiology, 2011, 13 (3), pp. 631-642.
Ma, Q. et al., "*Escherichia coli* BdcA controls biofilm dispersal in Pseudomona aeruginosa and Rhizobium Meliloti", BMC Research Notes, Oct. 26, 2011, 4, 10 pages.
Qun Ma et al, "Engineering a Novel c-di-GMP-Binding Protein for Biofilm Dispersal", NIH Public Access, Environ Microbiol. Mar. 2011; 13(3): 631-642.
Dana M. Lord et al., "BdcA, a Protein Important for *Escherichia coli* Biofilm Dispersal, Is a Short-Chain Dehydrogenase/Reductase that Binds Specifically to NADPH", PLOS ONE, vol. 9, Issue 9, Sep. 2014, pp. 1-8.
Ece Karatan et al., "Signals, Regulatory Networks, and Materials That Build and Break Bacterial Biofilms", Microbiology and Molecular Biology Reviews, Jun. 2009, pp. 310-347.
Qun Ma et al., "*Escherichia coli* BdcA controls biofilm dispersal in Pseudomonas aeruginosa and Rhizobium meliloti", BMC Research Notes 2011, 4:447, pp. 1-10.

* cited by examiner

*Primary Examiner* — Tekchand Saidha
(74) *Attorney, Agent, or Firm* — Rothwell, Figg Ernst & Manbeck, P.C.

(57) ABSTRACT

Provided herein is a genetically modified host cell comprising a heterologous nucleic acid encoding a biofilm dispersal polypeptide that decreases intracellular c-di-GMP levels and enhances the production of lysine and lysine derivatives. Further provided are methods of generating such cell and producing lysine and lysine derivatives using the genetically modified host cell.

36 Claims, 2 Drawing Sheets
Specification includes a Sequence Listing.

Figure 1. CLUSTAL O(1.2.1) multiple sequence alignment EAL domains of YahA and homologs

```
Pa_rocR_AAG07334.1      advvrgldngefeayyqpkvaldgggligaevlarwnhphlgvlppshflyvmetynlvd
Vc_vieA_EAZ76549.1      -eieqaflhdhifnyyqpqfdfrsgamvgvealvryehpthgmlspavflplieqcglhe
Ec_yahA_AHY69061.1      eaislalenhefkpwiqpvfcaqtgvltgcevlvrwehpqtgiippdqfiplaessgliv
Pa_bifA_AAG07755.1      -dlrdalqrhelhlvyqpqvdyrdhrvvgvealrwqhplhgfvppdlfiplaeqngsif
                         :.   .   :       * *.* *::**   *.: .*   *:.: *

Pa_rocR_AAG07334.1      klfwqlfsqglatrrk-laqlgqpinlafnvhpsqlgsralaenisalltefhlppssvm
Vc_vieA_EAZ76549.1      klfltvleksvsalas----igadlqlsvnisqrnlqhs-icdpilaicerygfpasklt
Ec_yahA_AHY69061.1      imtrqlmkqtadilmpvkhllpdnfhiginvsagcflaagfekeclnlvkklgndkiklv
Pa_bifA_AAG07755.1      sigewvldqacrqlrewhdqgfddlrmavnlstvqlhhnalprvvsnllqvyrlparsle
                          :   :                           :         :    :

Pa_rocR_AAG07334.1      feitetglisapasslenlvrlrimgcglamddfgagyssldrlcefpfsqikldrtfvq
Vc_vieA_EAZ76549.1      lemtehevyngtptslanlarlrmygvglsiddfgtgyaslgqlqpftelkidrsfvh
Ec_yahA_AHY69061.1      lelternpipvtpearaifdslhqhnitfalddfgtgyatyrylqafpvdfikidksfvq
Pa_bifA_AAG07755.1      levtetglmedistaaqhllslrragaliaiddfgtgysslyklspldkikidksfvq
                        :*:***     :  : ::::****:**::    *    :*:.:  .  :**:::***:

Pa_rocR_AAG07334.1      kmktqprscavissvvalaqalgislvvegvesdeqrvrlielgcsiaggylfarpmpeq
Vc_vieA_EAZ76549.1      dlatnykhqqltnmclllaqslglhcvvegveneetwqylrqlgvdtcqgyyaakpmpia
Ec_yahA_AHY69061.1      masvdeisghivdnivelarkpglsivaegvetqeqadlmigkgvhflqgylysppvp--
Pa_bifA_AAG07755.1      dllqdeddativraliqlgkslgmqviaegvetaeqeayiiaegcneggqylyskplpar
                                   .   *    .    : :.****. *     * .***  :  *:.*

Pa_rocR_AAG07334.1      h
Vc_vieA_EAZ76549.1      q
Ec_yahA_AHY69061.1      l
Pa_bifA_AAG07755.1      e Pa = Pseudomonas aeruginosa
Vc = Vibrio cholerae
Ec = Escherichia coli
```

Figure 2 CLUSTAL O(1.2.1) multiple sequence alignment--bdcA

```
Ec_bdcaA_OAC37747.1    ----------------------mgaftgktvlilggsrgigaaivrrfvtdganvrftya
Re_phaB_3VZS_A         ---------------MRGSHHHHHHGSTQRIAYVTGMGGIGTAICQRLAKDGFRVVAGCG
Se_4DMM_C              mgsshhhhhssglvprgshmtalpltdrialvtgasrgigraialelaaagakvavnya
Bs_fabG_NP_389473.1    ---------------mlndktaivtgasrgigrsialdlaksganvvvnys
                                              .  : .*. ** .* :   *..*

Ec_bdcaA_OAC37747.1    gskdaakrlaqetgat-----avftdsa-----drdavidvvrksgaldilvvnagivfg
Re_phaB_3VZS_A         PNSPRREKWLEQQKALGFDFIASEGNVADWDSTKTAFDKVKSEVGEVDVLINNAGITRDV
Se_4DMM_C              ssagaadevvaaiaaaggeafavkadvsqeseveafaavierwgrldvlvnnagitrdt
Bs_fabG_NP_389473.1    gneakanevvdeiksmgrkaiavkadvsnpedvqnmiketlsvfstidilvnnagitrdn
                                      *             .         .    . .:*:*: ****

Ec_bdcaA_OAC37747.1    ealelnaddidrlfkinihapyhasveaargmpe--ggriliigsvngdrmpvagmaaya
Re_phaB_3VZS_A         VFRKMTRADWDAVIDTNLTSLFNVTKQVIDGMADRGWGRIVNISSVNGQK-GQFGQTNYS
Se_4DMM_C              lllrmkrddwqsvldlnlggvflcsraaakimlkqrsgriiniasvvgem-gnpgqanys
Bs_fabG_NP_389473.1    limrmkedewddvininlkgvfnctkavtrqmmkqrsgriinvssivgvs-gnpgqanyv
                                   *  :  .    *  .  :  . :::*:   . .:*:*:* *

Ec_bdcaA_OAC37747.1    asksalqgmarglardfgprgitinvvqpgpidtdanpan-gpmrdmlhslmaikrhgqp
Re_phaB_3VZS_A         TAKAGLHGFTMALAQEVATKGVTVNTVSPGYIATDMVKAIRQDVLDKIVATIPVKRLGLP
Se_4DMM_C              aakagviglktkvakelasrgitvnavapgfiatdmtselaa---eklleviplgrygea
Bs_fabG_NP_389473.1    aakagviglktkssakelasrnitvnaiapgfistdmtdklakdvqdemlkqiplarfgep
                       :: *::.: *::.  *:::..  : .:*:: :** ** **

Ec_bdcaA_OAC37747.1    eevagmvawlagp-easfvtgamhtidgafga-
Re_phaB_3VZS_A         EEIASICAWLSSE-ESGFSTGADFSLNGGLHMG
Se_4DMM_C              aevagvvrflaadpaaayitgqvinidgglvma
Bs_fabG_NP_389473.1    sdvssvtflase-garymtgqtlhidggmvm-
                       :::.:  :*:.    . **     :*:.
```

"Re" refers to Ralstonia eutropha
"Se" refers to Synechoccus elongatus
"Bs" refers to Bacillus subtilis

CONTROL OF BIOFILM DISPERSAL FOR THE PRODUCTION OF AMINO ACIDS OR AMINO ACID-DERIVED PRODUCTS

CROSS-REFERENCE TO RELATED APPLICATIONS

The present application is a national stage filing under 35 U.S.C. § 371 of PCT/CN2016/095281, filed on 15 Aug. 2016. Each application is incorporated herein by reference in its entirety.

BACKGROUND OF THE INVENTION

The ability for a molecule to move into and out of a cell can have a significant effect on the intracellular concentration of the molecule. For example, if the molecule is a nutrient, then slowing the movement of the molecule into the cell would inhibit growth (Herbert, D & H L Kornberg, Biochem. J. 156(2), 477-480, 1976). If the molecule is a toxin, then slowing the movement of the molecule out of the cell would inhibit growth. If the molecule is a substrate in a reaction, then slowing the movement of the molecule into the cell would slow down the rate of the reaction. If the molecule is an intermediate in a series of reactions, then slowing the movement of the molecule out of the cell and allowing it to accumulate inside the cell could lead to feedback inhibition (Kikuchi et al., FEMS Microbiology Letters 173:211-215, 1999; Ogawa-Miyata et al., Biosci. Biotechnol. Biochem. 65:1149-1154, 2001).

Previous studies of the production of amino acids, such as lysine, and amino acid-derived products, such as cadaverine, focus on the overexpression or attenuation of genes involved in cellular metabolism. These modifications increase fluxes that lead to the production of the desired product, and decrease fluxes that lead to the production of side products or other metabolites not necessary for the formation of the desired product. However, additional methods of increasing the production of amino acids and their derived products are needed.

BRIEF SUMMARY OF ASPECTS OF THE DISCLOSURE

This disclosure is based, in part, on the surprising discovery that a protein that increases biofilm dispersal by reducing the intracellular concentration of bis-(3'-5')-cyclic diguanosine-monophosphate (c-di-GMP) affects the production of an amino acid, e.g., lysine, and its derived products, such as cadaverine. Although various genes have been shown to hydrolyze c-di-GMP and increase biofilm dispersal activity (e.g., bdcA oryahA from *E. coli*; rapA, fleN, rocR, or bifA from *P. aeruginosa*; vieA or mbaA from *V. cholerae*; and rmdAB from *S. coelicolor*), any effects of increasing biofilm dispersal activity by reducing intracellular c-di-GMP concentrations on the production of amino acids or their derivatives were unknown. Thus, in one aspect, the invention provides a genetically modified microorganism in which a biofilm dispersal polypeptide is overexpressed relative to a counterpart microorganism of the same strain that does not comprise the genetic modification. In some embodiments, the microorganism is genetically modified by introducing an expression vector comprising a nucleic acid sequence that encodes the biofilm dispersal polypeptide into the microorganism. In some embodiments, the microorganism is genetically modified to overexpress an endogenous biofilm dispersal polypeptide by introducing multiple copies of a gene encoding the endogenous biofilm dispersal polypeptide into the genome and/or by increasing expression of an endogenous gene using a heterologous promoter.

In one aspect, the invention provides a genetically modified host cell comprising a heterologous nucleic acid encoding a biofilm dispersal polypeptide, wherein the host cell overexpresses the biofilm dispersal polypeptide and has increased production of an amino acid or its derivative relative to an unmodified counterpart host cell. In some embodiments, the biofilm dispersal polypeptide is a BdcA or YahA polypeptide. In some embodiments, the biofilm dispersal polypeptide has at least 70% identity, or at least 75%, 80%, 85%, 90%, or 95% identity to the biofilm dispersal polypeptide sequence of SEQ ID NO: 4 or SEQ ID NO:6. In some embodiments, the heterologous nucleic acid encoding the biofilm dispersal polypeptide is encoded by an expression vector introduced into the cell, wherein the expression vector comprises the heterologous nucleic acid operably linked to a promoter. In some embodiments, the biofilm dispersal polypeptide is endogenous to the host cell. In some embodiments, the heterologous nucleic acid is integrated into the host chromosome. In some embodiments, the genetically modified host cell host cell overexpresses a lysine decarboxylase and/or one or more lysine biosynthesis polypeptides. In some embodiments, the host cell overexpresses a TetA polypeptide. In some embodiments, the host cell is of the genus *Escherichia*, *Hafnia*, or *Corynebacterium*. In some embodiments, the host cell is *Escherichia coli*, *Hafnia alvei*, or *Corynebacterium glutamicum*. In some embodiments, the biofilm dispersal polypeptide is a BdcA or YahA polypeptide. In some embodiments, the host cell overexpresses a LysC, DapA, LysA, Asd, DapB, AspC, or TetA polypeptide. In some embodiments, the amino acid is lysine and the amino acid derivative is cadaverine.

In a further aspect, the invention provides a method of producing an amino acid or its derivative, the method comprising culturing a genetically modified host cell as described herein, e.g., as described in the preceding paragraph under conditions in which the biofilm dispersal polypeptide is overexpressed. In some embodiments, the amino acid is lysine and the amino acid derivative is cadaverine.

In another aspect, the invention provides a method of engineering a host cell to increase production of an amino acid or its derivative, the method comprising introduce a heterologous nucleic acid encoding a biofilm dispersal polypeptide into the host cell, and culturing the host cell under conditions in which the heterologous biofilm dispersal polypeptide is expressed, wherein expression of the biofilm dispersal polypeptide increases the production of lysine or a lysine derivative relative to an unmodified counterpart control host cell. In some embodiments, the biofilm dispersal polypeptide is a BdcA or YahA polypeptide. In some embodiments, the biofilm dispersal polypeptide has at least 70% identity, or at least 75%, 80%, 85%, 90%, or 95% identity to a biofilm dispersal polypeptide having a sequence set forth in SEQ ID NO: 4 or SEQ ID NO:6. In some embodiments, the heterologous nucleic acid encoding the biofilm dispersal polypeptide is encoded by an expression vector introduced into the cell, wherein the expression vector comprises the heterologous nucleic acid operably linked to a promoter. In some embodiments, the biofilm dispersal polypeptide is endogenous to the host cell. In some embodiments, the heterologous nucleic acid is integrated into the host chromosome. In some embodiments, the host cell overexpresses a lysine decarboxylase and/or one or more lysine biosynthesis polypeptides. In some embodiments, the host cell overexpresses a TetA polypeptide. In some embodiments, the host cell is of the genus *Escherichia, Hafnia*, or *Corynebacterium*. In some embodiments, the host cell is *Escherichia coli, Hafnia alvei*, or *Corynebacterium glutamicum*. In some embodiments, the biofilm dispersal polypeptide is a BdcA or YahA polypeptide. In some embodiments, the host cell overexpresses a lysine decarboxylase polypeptide and a LysC, DapA, LysA, Asd, DapB, or AspC; or a TetA polypeptide. In some embodiments, the amino acid is lysine and the amino acid derivative is cadaverine.

BRIEF DESCRIPTION OF THE DRAWINGS

FIG. 1 showing the sequence alignment of EAL domains of YahA from *Pseudomonas aeruginosa* (Pa_ro-cR_AAG07334.1 (SEQ ID NO: 28); Pa_bifA_AAG07755.1 (SEQ ID NO: 31)), *Vibrio cholera* (Vc_vieA_EAZ76549.1 (SEQ ID NO: 29)), and *Escherichia coli* (Ec_yahA_AHY69061.1 (SEQ ID NO: 30)).

FIG. 2 showing the sequence alignment of bdcA from *Escherichia coli* (Ec_bdcaA_OAC37747.1 (SEQ ID NO: 4)), *Ralstonia eutropha* (Re_phaB_3VZS_A (SEQ ID NO: 32)), *Synechoccus elongatus* (Se_4DMM_C (SEQ ID NO: 33)) and *Bacillus subtilis* ((Bs_fabG_NP_389473.1 SEQ ID NO: 34)).

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

As used herein, the term "biofilm" refers to aggregates of bacteria that form a coating that contains living cells that form on either biotic or abiotic surfaces. Cells forming the biofilm are held together by an extracellular matrix that is composed of various substances, including polysaccharides, lipids, proteins, or DNA. Biofilm development comprises various steps: movement of the cells to the interface, initial reversible attachment of the cells to the interface, irreversible attachment to the interface, formation of small aggregates, biofilm maturation, and biofilm dispersal.

As used herein, the term "biofilm dispersal" refers to the final stage of the biofilm development cycle when cells are dispersed from the biofilm into the environment. Biofilm dispersal is a regulated process that can be caused by various internal and external signals. Some signals that trigger biofilm dispersal are nutrient deprivation, oxygen depletion, and a sudden increase in concentration of a toxic compound produced by the cell.

As used in the context of the present disclosure, a "biofilm dispersal polypeptide" refers to a polypeptide that decreases intracellular c-di-GMP levels. Such a polypeptide may reduce intracellular c-di-GMP levels by sequestering the compounds or by metabolizing c-di-GMP. A polypeptide that decreases intracellular c-di-GMP levels in accordance with the disclosure typically decreases levels by at least 10%, at least 15%, at least 20%, at least 25%, at least 30%, at least 35%, at least 40%, at least 45%, or at least 50%, or greater, when produced by a host cell genetically modified to overexpress the biofilm dispersal polypeptide compared to a wildtype counterpart host cell that has not been genetically modified to overexpress the biofilm dispersal polypeptide.

The term "biofilm dispersal polypeptide" encompasses biologically active variants, alleles, mutants, and interspecies homologs to the specific polypeptides described herein. A nucleic acid that encodes a biofilm dispersal polypeptide refers to a gene, pre-mRNA, mRNA, and the like, including nucleic acids encoding variants, alleles, mutants, and interspecies homologs of the particular amino acid sequences described herein.

One secondary messenger that regulates biofilm dispersal is bis-(3'-5')-cyclic diguanosine-monophosphate (c-di-GMP), which can bind to various proteins to modulate their transcription, translation, enzyme activity, and interaction with other proteins. Biofilm dispersal polypeptides with phosphodiesterase activity that hydrolyze c-di-GMP to the dinucleotide 5'-pGpG have been characterized (see, e.g., Karatan and Watnick, 2009 for a review). One type of conserved structural feature of these polypeptides that have phosphodiesterase activity is the EAL (also known as DUF2) protein domain that contains many conserved acidic amino acid residues and is characterized by the signature motif, glutamate-alanine-leucine (see, e.g., Schmidt et al, 2005). The EAL domain contains the consensus polypeptide sequence motif EAL (glutamate-alanine-leucine) that binds c-di-GMP. Another protein domain found in proteins with the ability to bind c-di-GMP is the PilZ domain, such as that found *E. coli* YcgR (Benach et al., *EMBO J.* 26, 5153-5166, 2007). The polypeptide sequence motifs that binds c-di-GMP in the PilZ domain are RXXXR (arginine-three amino acids-arginine) and (D/N)XSXXG (aspartate/asparagine-amino acid-serine-two amino acids-glycine). YahA is annotated with an EAL protein domain and was demonstrated to have phosphodiesterase activity on c-di-GMP (Sundruyal, et al., *J. Biol. Chem.* 289, 6978-6990, 2014). Although BdcA is not annotated to have an EAL domain or PilZ domain, BdcA contains both the EAL and RXXXR motifs associated with proteins that bind c-di-GMP. In addition, BdcA contains a IGSXXG (isoleucine-glycine-serine-two amino acids-glycine) polypeptide sequence that is similar to the PelZ (D/N)XSXXG c-di-GMP binding motif. The IGSXXG polypeptide sequence is also found in the lon protease (Lon) from *E. coli* along with the RXXXR binding motif. While Lon is also not annotated to have either an EAL or PelZ protein domains, it was predicted to bind c-di-GMP due to the presence of the above polypeptide motifs in its polypeptide sequence. It was also confirmed that Lon does in fact bind to c-di-GMP (Osbourne D O, et al. *Bioengineered* 5:4, 1-5, 2014). BdcA binding to c-di-GMP was shown by Ma, et al., *Environ Microbiol* 13, 631-642, 2011 using HPLC, but it was also observed that BdcA does not bind to c-di-GMP as well as the other cofactor NADPH (Lord, et al. *PLOS One* 9:9, e105751, 2014) using differential scanning fluorimetry. The ability for BdcA to exhibit biofilm dispersal activity was further demonstrated by its expression in a heterologous host where it also led to biofilm dispersal (Ma, et al. *BMC Research Notes* 4:447, 1-10, 2011). Therefore, the EAL, Rte, or IGSXXG polypeptide sequence motifs are important determinants of whether a protein will bind to c-di-GMP or not, or act on a pathway that interacts with c-di-GMP. The EAL, Rte, and IGSXXG motifs are underlined in SEQ ID NO: 4, and the annotated EAL domain is underlined and EAL motif is shown in bold in SEQ ID NO: 6. Thus, in one embodiment, a biofilm dispersal polypeptide in accordance with the present disclosure binds c-di-GMP. In some embodiments, a biofilm dispersal polypeptide in accordance with the present disclosure has phosphodiesterase activity. In some embodiments, a biofilm dispersal polypeptide in accordance with the present disclosure is a BdcA or a YahA.

A "BdcA" polypeptide refers to an *Escherichia coli* BdcA polypeptide having the amino acid sequence of SEQ ID NO:4, or a biologically active variant thereof. Biologically active variants includes alleles, mutants, and interspecies homologs of the *E. coli* BdcA polypeptide. Illustrative BdcA polypeptides from other species include *Shigella boydii* protein sequence accession number EIQ22376.1; *Shigella flexneri* protein sequence accession number WP 000500714.1; *Klebsiella pneumoniae* protein sequence accession number CDK74929.1; and Enterobacteriaceae sp protein sequence accession number WP_004203956.1. A "BdcA" polypeptide has at least 60% amino acid sequence identity, typically at least 65%, 70%, 75%, 80%, 85%, 90%, 91%, 92%, 93%, 94%, 95%, 96%, 97%, 98% or 99% or greater amino acid sequence identity, preferably over a region of at least about 50, 100, 150, or 200, or more, amino acids, or over the length of, the BdcA polypeptide of SEQ ID NO:4. A "BdcA polynucleotide" as used herein refers to a polynucleotide that encodes a BdcA polypeptide. A biologically active variant is able to enhance production of an amino acid, e.g., lysine, or amino acid derivative, e.g., cadaverine, for example when tested in a two-plasmid system as described in the Example section.

A "YahA" polypeptide refers to an *Escherichia coli* YahA polypeptide having the amino acid sequence of SEQ ID NO:6, or a biologically active variant thereof that has phosphodiesterase activity. Biologically active variants includes alleles, mutants, and interspecies homologs of the *E. coli* YahA polypeptide. Illustrative YahA polypeptides from other species include *Salmonella enterica*, protein sequence accession number WP 052944055.1; *Klebsiella pneumoniae* protein sequence accession number EOY80439.1; *Shigella sonnei* protein sequence accession number CSQ46493.1; and *Escherichia albertii* protein sequence accession number WP_00432879.1. A "YahA" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, 100, or more, amino acids, or over the length of the YahA polypeptide of SEQ ID NO: 6. A "YahA polynucleotide" as used herein refers to a polynucleotide that encodes a YahA polypeptide.

The terms "increased expression" and "overexpression" of a biofilm dispersal polypeptide are used interchangeably herein to refer to an increase in the amount of biofilm dispersal polypeptide in a genetically modified cell, e.g., a cell into which an expression construct encoding an biofilm dispersal polypeptide has been introduced, compared to the amount of biofilm dispersal polypeptide in a counterpart cell that does not have the genetic modification, i.e., a cell of the same strain without the modification. An increased level of expression for purposes of this application is at least 5%, or at least 10%, 20%, 30%, 40%, 50%, 60%, 70%, 80%, 90%, 100%, or greater, compared to the counterpart unmodified cell. The unmodified cell need not express the biofilm dispersal polypeptide. Thus, the term "overexpression" also includes embodiments in which a biofilm dispersal polypeptide is expressed in a host cell that does not natively express the biofilm dispersal polypeptide. Increased expression of a biofilm dispersal polypeptide can be assessed by any number of assays, including, but not limited to, measuring the level of RNA transcribed from the biofilm dispersal polypeptide gene, the level of biofilm dispersal polypeptide, and/or the level of biofilm dispersal polypeptide activity.

Phosphodiesterase activity of a biofilm dispersal polypeptide variant, e.g., a YahA polypeptide variant includes, but is not limited to, the ability to hydrolyze c-di-GMP to the dinucleotide 5'-pGpG. Phosphodiesterase activity can be measured using any method. For examples, phosphodiesterase activity may be determined by incubating e a purified protein with [$^{32}$P]c-di-GMP in a buffer such as 75 mM Tris, 250 mM NaCl, 25 mM KCl, and 10 mM MgCl$_2$. An aliquot of the reaction can then be spotted onto PEI-cellulose and allowed to dry. The nucleotides are separated using TLC in 1.5 M KH$_2$PO$_4$, and visualized using phosphoimagery. Alternatively, phosphodiesterase activity may be assess using HPLC with radiolabeled c-di-GMP is described in Schmidt et al., *J. Bacteriol.* 187, 4774-4781, 2005. A YahA variant of the invention typically has at least 20%, 30%, 40%, 50%, 60%, 70%, 80%, 90%, or greater, phosphodiesterase activity compared to a native YahA.

The activity of a biofilm dispersal polypeptide of the disclosure, e.g., the activity of a YahA or of a BdcA biofilm dispersal polypeptide variant, can be assessed using any functional assay reflecting the biofilm dispersal activity, including enhancement the production of an amino acid or amino acid derivative. The Examples section provides illustrative assays.

The term "enhanced" in the context of the production of an amino acid, e.g., lysine, or a lysine derivative, e.g., cadaverine, as used herein refers to an increase in the production of lysine or the derivative of a genetically modified host cell in comparison to a control counterpart cell, such as a cell of the wildtype strain or a cell of the same strain that does not have the genetic modification to increase production of the amino acid or amino acid derivative. Production of the amino acid or its derivative is enhanced by at least 5%, typically at least 0%, 20%, 30%, 40%, 50%, 60%, 70%, 80%, 90%, 100%, or greater compared to the control cell.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a residue in a BdcA polypeptide variant or homolog "corresponds to" an amino acid at a position in SEQ ID NO: 4 when the residue aligns with the amino acid in a comparison of SEQ ID NO: 4 and the homolog or variant in a maximal alignment.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether a biofilm dispersal polypeptide has sequence identity to SEQ ID NO: 4, or 6, or another polypeptide reference sequence, is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). For amino acid sequences, the BLASTP program uses as defaults a word size (W) of 3, an expectation (E) of 10, and the BLOSUM62 scoring matrix (see Henikoff & Henikoff, 1989, Proc. Natl. Acad. Sci. USA 89:10915). Other programs that may be used include the Needleman-Wunsch procedure, J. Mol. Biol. 48: 443-453 (1970), using BLOSUM62, a Gap start penalty of 7 and gap extend penalty of 1; and gapped BLAST 2.0 (see Altschul, et al. 1997, Nucleic Acids Res., 25:3389-3402) both A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)).

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein or enzyme.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, refers to a polypeptide molecule that is free of other components of the cell, i.e., it is not associated with in vivo substances.

Aspects of the Disclosure

The present disclosure is based, in part, on the discovery that increased expression of one or more biofilm dispersal polypeptides in a microorganism, such as a gram negative bacteria, enhances amino acid, e.g., lysine, production and/or production of an amino acid derivative of lysine, such as cadaverine. A biofilm dispersal polypeptide that is overexpressed in accordance with the invention often is a polypeptide with the EAL protein motif.

A host cell that is engineered to overexpress a biofilm dispersal polypeptide is also typically engineered to overexpress an enzyme to synthesize the amino acid derivative, such as a lysine decarboxylase polypeptide, and/or an additional polypeptide that is involved in amino acid biosynthesis. Lysine decarboxylase and lysine biosynthesis polypeptide and nucleic acid sequences are well known in the art.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2014).

Polynucleotides Encoding Biofilm Dispersal Polypeptides

Various polynucleotides have been shown to encode polypeptides that hydrolyze c-di-GMP and increase biofilm dispersal activity (e.g., bdcA or yahA from *E. coli*; rapA, fleN, rocR, or bifA from *P. aeruginosa*; vieA or mbaA from *V. cholerae*; and rmdAB from *S. coelicolor*).

Biofilm dispersal nucleic acid and polypeptide sequences suitable for use in the invention include biofilm dispersal nucleic acid sequences that encode a biofilm dispersal polypeptide as illustrated in any of SEQ NOs: 4, or 6, or substantially identical variants thereof. Such a variant typically has at least 70%, or at least 75%, 80%, 85%, or 90% identity to one of SEQ ID NOS: 4, or 6, or an alternative biofilm dispersal polypeptide, e.g., a homolog of SEQ ID NO: 4, or 6. As used herein, the term "variant" encompasses biologically active polypeptides having one or more substitutions, deletions, or insertions relative to a biofilm dispersal polypeptide reference sequence, such as SEQ ID NO: 4, or 6. Thus, the term "variant" includes biologically active fragments as well as substitution variants.

In some embodiments, a biofilm dispersal polypeptide of the disclosure has phosphodiesterase activity that hydrolyzes bis-(3'-5')-cyclic diguanosine-monophosphate (c-di-GMP), a secondary messenger that regulates biofilm dispersal. These polypeptides have a conserved structural feature known as the EAL (also known as DUF2) protein domain. The EAL domain contains many conserved acidic amino acid residues and is characterized by the signature motif, glutamate-alanine-leucine (e.g., see Schmidt et al, *J Bacteriol.* 187: 4774-4781, 2005, which is incorporated by reference). An illustrative biofilm dispersal YahA polypeptide sequence having phosphodiesterase activity is provided in SEQ ID NO:6. The crystal structure of YahA has been determined. The protein has been shown to have a modified TIM-barrel fold (Sundruyal, et al., *J. Biol. Chem.* 289, 6978-6990, 2014). This fold is shared by other phosphodiesterase proteins with EAL domains and biofilm dispersal activity, such as RocR from *Pseudomonas aeruginosa* (Chen et al., *J. Bacteriol.* 194, 4837-4846, 2012). The EAL domain (Pfam PF00563) is approximately 250 amino acids and is underlined in SEQ ID NO:6. An alignment of the EAL domains from various proteins of difference species of bacteria is shown in FIG. 1. As previously described by Schmidt et al., *J Bacteriol.* 187, 4774-4781, 2005, there are several conserved sequences of amino acids within the domain even though the overall homology across the EAL domain sequences is about 30%.

In some embodiments, a biofilm dispersal polypeptide in accordance with the disclosure is a BdcA polypeptide. An illustrative sequence is provided as SEQ ID NO:4. BdcA has a Rossman-fold specific to binding NADPH. BdcA decreases the intercellular concentration of c-di-GMP in the native organism *E. coli* and when heterologously expressed in other microorganisms (Ma, et al., *BMC Research Notes* 4:447, 2011). SEQ ID NO:4 contains a short EAL sequence (aa 91-93) and forms a dimer, as does YahA and other c-di-GMP phosphodiesterases, but does not exhibit phosphodiesterase activity in vitro. An alignment of SEQ ID NO:4 with homologs from other species is shown in FIG. 2.

One of skill can obtain a biofilm dispersal polypeptide variant by using the sequence alignments and structural analyses available in the art to identify residues within conserved structures that would be expected to retain biofilm dispersal polypeptide function as well as that would be tolerant to substitution. For example, it was shown in Schmidt et al, *J Bacteriol.* 187: 4774-4781, 2005 that a purified EAL domain of YahA is sufficient to hydrolyze c-di-GMP.

The biofilm dispersal polypeptide activity can be assessed using any number of assays, including assays that evaluate the production of an amino acid or an amino acid-derived compound. An illustrative assay measures lysine production in *E. coli* that is modified to co-express LysC, DapA, LysA, Asd, DapB, AspC, and TetA on one plasmid with either BdcA or YahA, or a variant of a biodispersal polypeptide, on a second plasmid. Each plasmid has a unique antibiotic-resistance selectable marker. Antibiotic-resistant colonies are selected and cultured. For example, cultures are grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 µg/mL), and ampicillin (100 µg/mL). The following day, each culture was inoculated into 50 mL of fresh medium with 30 g/L of glucose, 0.7% $Ca(HCO_3)_2$, tetracycline (10 µg/mL), and ampicillin (100 µg/mL), and grown for 72 hours at 37° C., at which point the concentration of cadaverine in each culture was quantified using NMR, and yield is calculated by dividing the molar amount of cadaverine produced by the molar amount of lysine glucose added. A biofilm dispersal polypeptide for use in the invention increases the yield of lysine or cadaverine. Alternatively, colonies are evaluated for increased lysine production or production of another lysine derivative.

Isolation or generation of biofilm dispersal polynucleotide sequences can be accomplished by a number of techniques. Such techniques will be discussed in the context of biofilm dispersal genes. However, one of skill understands that the same techniques can be used to isolate and express other desired genes. In some embodiments, oligonucleotide probes based on the sequences disclosed here can be used to identify the desired polynucleotide in a cDNA or genomic DNA library from a desired bacteria; species. Probes may be used to hybridize with genomic DNA or cDNA sequences to isolate homologous genes in the same or different plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a biofilm dispersal polynucleotide in bacteria can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding a biofilm dispersal polypeptide for use in the disclosure includes genes and gene products identified and characterized by techniques such as hybridization and/or sequence analysis using illustrative nucleic acid sequences, e.g., SEQ ID NO:3 or SEQ ID NO:5. In some embodiments, a host cell is genetically modified by introducing a nucleic acid sequence having at least 60% identity, or at least 70%, 75%, 80%, 85%, or 90% identity, or 100% identity, to a polynucleotide comprising SEQ ID NO:3 or SEQ ID NO:5.

Nucleic acid sequences encoding a biofilm dispersal polypeptide that confers increased production of an amino acid, e.g., lysine, or an amino acid-derived product, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292).

Preparation of Recombinant Vectors

Recombinant vectors for expression of a biofilm dispersal polypeptide can be prepared using methods well known in the art. For example, a DNA sequence encoding a biofilm dispersal polypeptide (described in further detail below), can be combined with transcriptional and other regulatory sequences which will direct the transcription of the sequence from the gene in the intended cells, e.g., bacterial cells such as *E. coli*. In some embodiments, an expression vector that comprises an expression cassette that comprises the gene encoding the biofilm dispersal polypeptide further comprises a promoter operably linked to the biofilm dispersal gene. In other embodiments, a promoter and/or other regulatory elements that direct transcription of the biofilm dispersal gene are endogenous to the host cell and an expression cassette comprising the biofilm dispersal gene is introduced, e.g., by homologous recombination, such that the exogenous gene is operably linked to an endogenous promoter and is expression driven by the endogenous promoter.

As noted above, expression of the gene encoding a biofilm dispersal polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla pormoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, Appl. Environ. Microbiol. 64:82, 1998; Shimada, et al., J. Bacteriol. 186:7112, 2004; and Miksch et al., Appl. Microbiol. Biotechnol. 69:312, 2005.

In some embodiments, a promoter that influences expression of a native biofilm dispersal polypeptide may be modified to increase expression. For example, an endogenous BdcA or YahA promoter may be replaced by a promoter that provides for increased expression compared to the native promoter.

An expression vector may also comprise additional sequences that influence expression of a gene encoding the biofilm dispersal polypeptide. Such sequences include enhancer sequences, a ribosome binding site, or other sequences such as transcription termination sequences, and the like.

A vector expressing a nucleic acid encoding a biofilm dispersal polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*.

Although any suitable expression vector may be used to incorporate the desired sequences, readily available bacterial expression vectors include, without limitation: plasmids such as pSC1O1, pBR322, pBBR1MCS-3, pUR, pET, pEX, pMR1OO, pCR4, pBAD24, p15a, pACYC, pUC, e.g., pUC18 or pUC19, or plasmids derived from these plasmids; and bacteriophages, such as M1 3 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to overexpress a biofilm dispersal polypeptide. Such host cell may comprise a nucleic acid encoding a heterologous biofilm dispersal polypeptide, including any non-naturally occurring biofilm dispersal polypeptide variant; or may be genetically modified to overexpress a native, or endogenous, biofilm dispersal polypeptide relative to a wildtype host cell.

A genetically modified host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a host cell to overexpress a biofilm dispersal polypeptide is performed in conjunction with modifying the host cell to overexpress a lysine decarboxylase polypeptide and/or one or more lysine biosynthesis polypeptides.

A lysine decarboxylase refers to an enzyme that converts L-lysine into cadaverine. The enzyme is classified as E.C. 4.1.1.18. Lysine decarboxylase polypeptides are well characterized enzymes, the structures of which are well known in the art (see, e.g., Kanjee, et al., EMBO J. 30: 931-944, 2011; and a review by Lemmonier & Lane, Microbiology 144; 751-760, 1998; and references described therein). The EC number for lysine decarboxylase is 4.1.1.18. Illustrative lysine decarboxylase sequences are CadA homologs from *Klebsiella* sp., WP 012968785.1; *Enterobacter aerogenes*, YP 004592843.1; *Salmonella enterica*, WP 020936842.1; *Serratia* sp., WP 033635725.1; and *Raoultella ornithinolytica*, YP 007874766.1; and LdcC homologs from *Shigella* sp., WP 001020968.1; *Citrobacter* sp., WP 016151770.1; and *Salmonella enterica*, WP 001021062.1. As used herein, a lysine decarboxylase includes variants of native lysine decarboxylase enzymes that have lysine decarboxylase enzymatic activity. Additional lysine decarboxylase enzyme are described in PCT/CN2014/080873 and PCT/CN2015/072978.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde | asd | 1.2.1.11 | AAC76458.1 |

-continued

| Protein | Gene | EC Number | GenBank Accession No. |
|---|---|---|---|
| dehydrogenase (Asd) dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate:meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/ 4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/ 1.1.1.3 | NP_414543 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

Nucleic acids encoding a lysine decarboxylase or a lysine biosynthesis polypeptide may be introduced into the host cell along with the biofilm dispersal polynucleotide, e.g., encoded on a single expression vector, or introduced in multiple expression vectors at the same time. Alternatively, the host cell may be genetically modified to overexpress lysine decarboxylase or one or more lysine biosynthesis polypeptides before or after the host cells genetically modified to overexpress the biofilm dispersal polypeptide.

In alternative embodiments, a host cell that overexpresses a naturally occurring biofilm dispersal polypeptide can be obtained by other techniques, e.g., by mutagenizing cells, e.g., *E coli* cells, and screening cells to identify those that express a biofilm dispersal polypeptide, e.g., BdcA or YahA, at a higher level compared to the cell prior to mutagenesis.

A host cell comprising a biofilm dispersal polypeptide as described herein is a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella*, or *Klebsiella* taxonomical classes. In some embodiments, the host cells are members of the genus *Escherichia, Hafnia*, or *Corynebacterium*. In some embodiments, the host cell is an *Escherichia coli, Hafnia alvei*, or *Corynebacterium glutamicum* host cell.

In some embodiments, the host cell is a gram-positive bacterial host cell, such as a *Bacillus* sp., e.g., *Bacillus subtilis* or *Bacillus licheniformis*; or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis*.

Host cells modified in accordance with the invention can be screened for increased production of lysine or a lysine derivative, such as cadaverine, as described herein.

Methods of Producing Lysine or a Lysine Derivative.

A host cell genetically modified to overexpress a biofilm dispersal polypeptide can be employed to produce lysine or a derivative of lysine. In some embodiments, the host cell produces cadaverine. To produce lysine or the lysine derivative, a host cell genetically modified to overexpress a biofilm dispersal polypeptide as described herein can be cultured under conditions suitable to allow expression of the polypeptide and expression of genes that encode the enzymes that are used to produce lysine or the lysine derivative. A host cell modified in accordance with the invention provides a higher yield of lysine or lysine derivatives relative to a non-modified counterpart host cell that expresses the biofilm dispersal polypeptide at native levels.

Host cells may be cultured using well known techniques (see, e.g., the illustrative conditions provided in the examples section.

The lysine or lysine derivative then be separated and purified using known techniques. Lysine or lysine derivatives, e.g., cadverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1: Construction of Plasmid Vectors that Encode CadA

A plasmid vector containing wild-type E. coli cadA (SEQ ID NO: 1), which encodes the lysine decarboxylase CadA (SEQ ID NO: 2), was amplified from the E. coli MG1655 K12 genomic DNA using the PCR primers cadA-F and cadA-R, digested using the restriction enzymes SacI and XbaI, and ligated into pUC18 to generate the plasmid pCIB60. The 5' sequence upstream of the cadA gene was optimized using the PCR primers cadA-F2 and cadA-R2 to create pCIB71.

Example 2: Construction of Plasmid Vectors Expressing a Biofilm Dispersal Polypeptide The E. coli gene, bdcA (SEQ ID NO: 3), that encodes the biofilm dispersal protein, BdcA (SEQ ID NO: 4), was amplified from the E. coli MG1655 K12 genomic DNA using the PCR primers bdcA-F and bdcA-R, digested with the restriction enzymes SacI and XbaI, and ligated into a pUC18 plasmid vector to create pCIB85. The 5' sequence upstream of the bdcA gene was optimized using the PCR primers bdcA-F2 and bdcA-R2 to create pCIB119. Similarly, yahA (SEQ ID NO: 5), that encodes the biofilm dispersal protein, YahA (SEQ ID NO: 6), was cloned into a pUC18 plasmid vector using the primers yahA-F and yahA-R to create the plasmid pCIB107. The 5' sequence upstream of the yahA gene was optimized using the PCR primers yahA-F2 and yahA-R2 to create pCIB162.

Example 3: Construction of Plasmid Vectors that Encode a Tetracycline Efflux Pump The synthetic promoter sequence (SEQ ID NO: 7) was synthesized using the PCR primers psyn-1 and psyn-2. Primer psyn-1 contains the promoter sequence and a sequence homologous to pUC18, and primer psyn-2 contains a sequence homologous to pUC18. These two PCR primers were used to amplify a portion of pUC18 that includes the multi-cloning site from the plasmid inserted downstream of the synthetic promoter sequence. Restriction enzymes EcoRI and ScaI were used to digest the amplified DNA containing the synthetic promoter, which was further ligated into pUC18 to construct pCIB10.

The tetA gene (SEQ ID NO: 8), that encodes a tetracycline efflux pump, TetA (SEQ ID NO: 9), was amplified from the E. coli cloning vector pBR322 using the PCR primers tetA-F and tetA-R. The amplified DNA was digested with the restriction enzymes SacI and XbaI, and ligated into pCIB10 plasmid vector to create pCIB20.

Example 4: Construction of Plasmid Vectors Co-Expressing Synthetic Operon I that Contains Three Proteins (LysC, DapA, LysA) from the Lysine Biosynthetic Pathway Three genes from E. coli, lysC, dapA, and lysA, encode proteins involved in the E. coli lysine biosynthetic pathway: aspartate kinase (LysC or AKIII, encoded by lysC), dihydrodipicolinate synthase (DapA or DHDPS, encoded by dapA), and diaminopimelate decarboxylase (LysA, encoded by lysA). The three genes were cloned into a plasmid vector and the three proteins, LysC (SEQ ID NO: 11), DapA (SEQ ID NO: 13), and LysA (SEQ ID NO: 15) were overexpressed in E. coli. The gene lysC was amplified from the E. coli MG1655 K12 genomic DNA using the primers lysC-F and lysC-R, and the amplified fragment was digested using SacI and BamHI, and ligated into pUC18 to create pCIB7. The gene dapA was amplified from the E. coli MG1655 K12 genomic DNA using the primers dapA-F and dapA-R, and the amplified fragment was digested using BamHI and XbaI, and ligated into pCIB7 to create pCIB8. The gene lysA was amplified from the E. coli MG1655 K12 genomic DNA using the primers lysA-F and lysA-R, and the amplified fragment was digested using XbaI and SalI, and ligated into pCIB8 to create pCIB9. The three-gene operon was amplified from pCIB9 using the primers lysC-F and lysA-R. The amplified product was digested using SacI and SalI, and the digested fragment was ligated into pCIB10 to create pCIB32. The gene tetA was amplified from pCIB20 using the primers tetA-F3 and tetA-R3, and the amplified fragment was digested using SbfI and XhoI, and ligated into pCIB32 to generate plasmid pCIB42.

Example 5: Construction of Plasmid Vectors Co-Expressing Various Aspartokinases. Various Aspartokinases were Expressed in Order to Increase Lysine Production Two pairs of mutations were chosen that enabled the E. coli aspartokinase III (LysC or AKIII, encoded by lysC, SEQ ID NO: 10) to have an increased feedback resistance to lysine. The gene encoding the first mutant, LysC-1 (M318I, G323D) (SEQ. ID NO: 17) was constructed using the primers 318-F, 318-R, 323-F, 323-R. The genes encoding LysC-1 (M318I, G323D) was cloned into pCIB32 and replaced the wild-type E. coli aspartokinase, LysC, to create the plasmids pCIB43. The aspartokinase from Streptomyces strains that is capable of producing polylysine was previously suggested, but not proven, to be more feedback resistant to lysine compared to E. coli aspartokinase. As such, the aspartokinase gene from Streptomyces lividans was codon optimized, synthesized, and cloned in place of wild-type lysC in pCIB32 in order to create the plasmid pCIB55 using the primers SlysC-F and SlysC-R. The resulting aspartokinase protein that was expressed was named S-LysC (SEQ ID NO: 19).

Example 6: Construction of Plasmid Vectors Co-Expressing Synthetic Operon II that Contains Three Proteins (Asd, DapB, DapD, AspC) from the Lysine Biosynthetic Pathway Next, the expression of four additional genes, asd, dapB, dapD, and aspC, which are involved in the lysine biosynthetic pathway of *E. coli*, was enhanced. These genes encode the following enzymes: aspartate semialdehyde dehydrogenase (Asd (SEQ ID NO: 21), encoded by asd), dihydrodipicolinate reductase (DapB or DHDPR (SEQ ID NO: 23), encoded by dapB), tetrahydrodipicolinate succinylase (DapD (SEQ ID NO: 25), encoded by dapD), and aspartate transaminase (AspC (SEQ ID NO: 27), encoded by aspC). The gene asd was amplified from the *E. coli* MG1655 K12 genomic DNA using the primers asd-F and asd-R, and the amplified fragment was digested using SacI and BamHI, and ligated into pUC18 to create pCIB12. The gene dapB was amplified from the *E. coli* MG1655 K12 genomic DNA using the primers dapB-F and dapB-R, and the amplified fragment was digested using BamHI and XbaI, and ligated into pCIB12 to create pCIB13. The gene dapD was amplified from the *E. coli* MG1655 K12 genomic DNA using the primers dapD-F and dapD-R, and the amplified fragment was digested using XbaI and SalI, and ligated into pCIB13 to create pCIB14. Similarly, the gene aspC was amplified from the *E. coli* MG1655 K12 genomic DNA using the primers aspC-F and aspC-R, and the amplified fragment was digested using XbaI and SalI, and ligated into pCIB13 to create pCIB31. The gene tetA was amplified from pCIB20 using the primers tetA-F3 and tetA-R3, and the amplified fragment was digested using XhoI and SphI and ligated into pCIB14 and pCIB31 to generate plasmids pCIB15 and pCIB59, respectively.

Example 7: Construction of Plasmid Vectors Co-Expressing Synthetic Operons I and II that Contain Proteins from the Lysine Biosynthetic Pathway The two synthetic operons, Synthetic Operon I and Synthetic Operon II, consisting of the genes lysC, dapA, lysA, asd, dapB, and aspC were combined into a single vector. The operon from pCIB32 consisting of the genes lysC, dapA, and lysA was amplified using the primers LAL-F and LAL-R. The operon from pCIB59 consisting of the genes asd, dapB, and aspC and the tetA gene was amplified using the primers ABC-F and ABCT-R. The products were digested using the restriction enzymes ApaI and KpnI. The digested products of pCIB32 and pCIB59 were ligated to form pCIB103-1. Similarly, the variants of Synthetic Operon I that contain different aspartokinases were combined with Synthetic Operon II. The variant of Synthetic Operon I that contains LysC-1 was amplified from pCIB43 using the primers LAL-F and LAL-R, digested, and ligated with the digested product of pCIB59 to form pCIB103-2. The variant of Synthetic Operon I that contains S-LysC was amplified from pCIB55 using the primers SAL-F and SAL-R, digested, and ligated with the digested product of pCIB59 to form pCIB103-3.

Example 8: Production of Lysine from *E. coli* Over-Expressing Lysine Synthetic Operons I and II

*E. coli* MG1655 K12 was transformed with one of the following plasmids: pCIB20, pCIB103-1, pCIB103-2, or pCIB103-3, in order to make the respective strains: CIB20, CIB103-1, CIB103-2, or CIB103-3 (FIG. 2). Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, and tetracycline (10 µg/mL). The following day, each culture was inoculated into 100 mL of fresh medium with 30 g/L of glucose, 0.7% $Ca(HCO_3)_2$, and tetracycline (10 µg/mL) and grown for 72 hours at 37° C., at which point the concentration of lysine in each culture was determined (Table 1).

TABLE 1

Production of lysine by *E. coli* strains containing Synthetic Operons I and II.

| Strain | Protein(s) | Lysine (g/L) |
|---|---|---|
| CIB20 | TetA | n.d. |
| CIB103-1 | LysC, DapA, LysA, Asd, DapB, AspC, TetA | 1.0 ± 0.4 |
| CIB103-2 | LysC-1, DapA, LysA, Asd, DapB, AspC, TetA | 6.6 ± 0.2 |
| CIB103-3 | S-LysC, DapA, LysA, Asd, DapB, AspC, TetA | 6.0 ± 0.5 | n.d.: none detected

As shown in Table 1, the over production of different variants of aspartokinase (LysC-1, LysC-2, S-LysC) increased lysine production compared to the expression of wild-type *E. coli* aspartokinase (LysC)—compare 1.0 g/L for CIB103-1 to 6.6 g/L for CIB103-2, 6.0 g/L for CIB103-3.

Example 9: Production of Lysine from *E. coli* Co-Overexpressing Genes that Encode Biofilm Dispersal Proteins and Lysine Synthetic Operons I and II CIB103-3 was transformed with one of the plasmids overexpressing one of the biofilm dispersal proteins: pCIB119 or pCIB162, in order to create the respective strains: CIB119 or CIB162.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and tetracycline (10 µg/mL). The following day, each culture was inoculated into 50 mL of fresh medium with 40 g/L of glucose, 0.7% $CaCO_3$, ampicillin (100 µg/mL) and tetracycline (10 µg/mL), and grown for 72 hours at 37° C., at which point the concentration of lysine in each culture was determined (Table 2).

TABLE 2

Production of lysine by *E. coli* strains that contain the lysine Synthetic Operons I and II and overproduce biofilm dispersal proteins.

| Strain | Protein(s) | Lysine (g/L) |
|---|---|---|
| CIB103-3 | S-LysC, DapA, LysA, Asd, DapB, AspC, TetA | 6.2 ± 0.1 |
| CIB119 | S-LysC, DapA, LysA, Asd, DapB, AspC, TetA, BdcA | 7.3 ± 0.3 |
| CIB162 | S-LysC, DapA, LysA, Asd, DapB, AspC, TetA, YahA | 6.9 ± 0.2 |

As shown in Table 2, overexpression of certain genes that encode biofilm proteins increase lysine production. The overproduction of BdcA and YahA increased lysine production—compare 6.2 g/L for CIB103-3 with 7.3 g/L for CIB119 and 6.8 g/L for CIB162.

Example 10: Construction of Plasmid Vectors Co-Expressing Biofilm Dispersal Proteins and CadA The *E. coli* biofilm dispersal genes, bdcA and yahA, were amplified as described in Example 2 using the appropriate primers (bdcA-F3, bdcA-R3, yahA-F3, yahA-R3), digested using XbaI and HindIII, and ligated into pCIB71 in order to co-express the biofilm dispersal genes with the lysine decarboxylase gene cadA. The plasmid co-expressing cadA and bdcA is pCIB123, and cadA and yahA is pCIB163.

Example 11: Production of Cadaverine from *E. coli* Co-Overexpressing Genes that Encode a Lysine Decarboxylase and the Lysine Synthetic Operons I and II CIB103-1, CIB103-2, and CIB103-3 were transformed with pCIB71 in order to construct the strains CIB71-1, CIB71-2, and CIB71-3. CIB71-1, CIB71-2, and CIB71-3 all express the genes that encode the lysine decarboxylase gene cadA, and six lysine biosynthesis genes. However, CIB71-1 expresses the wild-type *E. coli* aspartokinase lysC, CIB71-2 expresses a mutant feedback-resistant aspartokinase lysC-1, and CIB71-3 expresses the wild-type *S. lividans* aspartokinase S-lysC.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and ampicillin (100 μg/mL). The following day, each culture was inoculated into 50 mL of fresh medium with 40 g/L of glucose, 0.7% $CaCO_3$, tetracycline (10 μg/mL) and ampicillin (100 μg/mL), and grown for 72 hours at 37° C., at which point the concentration of lysine in each culture was determined (Table 3).

TABLE 3

Production of lysine and cadaverine by *E. coli* strains containing Synthetic Operons I and II and co-producing CadA.

| Strain | Protein(s) | Lysine (g/L) | Cadaverine (g/L) | Total (g/L) |
| --- | --- | --- | --- | --- |
| CIB103-1 | LysC, DapA, LysA, Asd, DapB, AspC, TetA | 2.4 ± 0.2 | n.d. | 2.4 |
| CIB103-2 | LysC-1, DapA, LysA, Asd, DapB, AspC, TetA | 5.9 ± 0.1 | n.d. | 5.9 |
| CIB103-3 | S-LysC, DapA, LysA, Asd, DapB, AspC, TetA | 5.8 ± 0.2 | n.d. | 5.8 |
| CIB71-1 | LysC, DapA, LysA, Asd, DapB, AspC, TetA, CadA | 0.5 ± 0.1 | 2.0 ± 0.2 | 2.5 |
| CIB71-2 | LysC-1, DapA, LysA, Asd, DapB, AspC, TetA, CadA | 0.6 ± 0.2 | 5.4 ± 0.2 | 6.0 |
| CIB71-3 | S-LysC, DapA, LysA, Asd, DapB, AspC, TetA, CadA | 0.5 ± 0.1 | 5.5 ± 0.1 | 6.0 |

As shown in Table 3, the overproduction of CadA with the lysine Synthetic Operons I and II leads to the production of both lysine and cadaverine.

Example 12: Production of Cadaverine from *E. coli* Co-Overexpressing Genes that Encode a Lysine Decarboxylase, Biofilm Dispersal Proteins, and the Lysine Synthetic Operons I and II CIB103-3 was transformed with pCIB71, pCIB123, or pCIB163 to make the respective strains CIB71-3, CIB123-3, and CIB163-3.

Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, tetracycline (10 μg/mL), and ampicillin (100 μg/mL). The following day, each culture was inoculated into 50 mL of fresh medium with 40 g/L of glucose, 0.7% $CaCO_3$, tetracycline (10 μg/mL), and ampicillin (100 μg/mL), and grown for 72 hours at 37° C., at which point the concentration of lysine in each culture was determined (Table 4).

TABLE 4

Production of lysine and cadaverine by *E. coli* strains containing Synthetic Operons I and II and co-producing CadA and biofilm dispersal proteins.

| Strain | Protein(s) | Lysine (g/L) | Cadaverine (g/L) | Total (g/L) |
| --- | --- | --- | --- | --- |
| CIB103-3 | S-LysC, DapA, LysA, Asd, DapB, AspC, TetA | 6.0 ± 0.1 | n.d. | 6.0 |
| CIB71-3 | S-LysC, DapA, LysA, Asd, DapB, AspC, TetA, CadA | 0.5 ± 0.2 | 5.5 ± 0.1 | 6.0 |
| CIB123-3 | S-LysC, DapA, LysA, Asd, DapB, AspC, TetA, CadA, BdcA | 0.5 ± 0.2 | 6.7 ± 0.2 | 7.2 |
| CIB163-3 | S-LysC, DapA, LysA, Asd, DapB, AspC, TetA, CadA, YahA | 0.5 ± 0.1 | 6.5 ± 0.2 | 7.0 |

As shown in Table 4, overproduction of the biofilm dispersal proteins BdcA and YahA in addition to CadA increased total lysine and cadaverine production compared to the control that only overproduced CadA in *E. coli* co-expressing the lysine Synthetic Operons I and II—compare 6.0 g/L for CIB71-3 to 7.2 g/L for CIB123-3.

| Table of plasmids used in Examples | | | |
| --- | --- | --- | --- |
| Host | Protein(s) Overexpressed | Plasmid | Strain |
| | CadA | pCIB71 | |
| | BdcA | pCIB119 | |
| | YahA | pCIB62 | |
| | TetA | pCIB20 | |
| | LysC | pCIB7 | |
| | LysC, DapA | pCIB8 | |

Table of plasmids used in Examples

| Host | Protein(s) Overexpressed | Plasmid | Strain |
|---|---|---|---|
| | LysC, DapA, LysA | pCIB9 | |
| | LysC, DapA, LysA | pCIB32 | |
| | LysC, DapA, LysA, TetA | pCIB42 | |
| | LysC-1, DapA, LysA | pCIB43 | |
| | S-LysC, DapA, LysA | pCIB55 | |
| | Asd | pCIB12 | |
| | Asd, DapB | pCIB13 | |
| | Asd, DapB, DapD | pCIB14 | |
| | Asd, DapB, AspC | pCIB31 | |
| | Asd, DapB, DapD, TetA | pCIB15 | |
| | Asd, DapB, AspC, TetA | pCIB59 | |
| | LysC, DapA, LysA, Asd, DapB, AspC, TetA | pCIB103-1 | |
| | LysC-1, DapA, LysA, Asd, DapB, AspC, TetA | pCIB103-2 | |
| | S-LysC, DapA, LysA, Asd, DapB, AspC, TetA | pCIB103-3 | |
| E. coli | TetA | | CIB20 |
| E. coli | LysC, DapA, LysA, Asd, DapB, AspC, TetA | | CIB103-1 |
| E. coli | LysC-1, DapA, LysA, Asd, DapB, AspC, TetA | | CIB103-2 |
| E. coli | S-LysC, DapA, LysA, Asd, DapB, AspC, TetA | | CIB103-3 |
| E. coli | S-LysC, DapA, LysA, Asd, DapB, AspC, TetA, BdcA | | CIB119 |
| E. coli | S-LysC, DapA, LysA, Asd, DapB, AspC, TetA, YahA | | CIB162 |
| | CadA, BdcA | pCIB123 | |
| | CadA, YahA | pCIB163 | |
| E. coli | LysC, DapA, LysA, Asd, DapB, AspC, TetA, CadA | | CIB71-1 |
| E. coli | LysC-1, DapA, LysA, Asd, DapB, AspC, TetA, CadA | | CIB71-2 |
| E. coli | S-LysC, DapA, LysA, Asd, DapB, AspC, TetA, CadA | | CIB71-3 |
| E. coli | S-LysC, DapA, LysA, Asd, DapB, AspC, TetA, CadA, BdcA | | CIB123-3 |
| E. coli | S-LysC, DapA, LysA, Asd, DapB, AspC, TetA, CadA, YahA | | CIB163-3 |

Table of primer sequences used in Examples.

| Name | Sequence (5'-3') |
|---|---|
| cadA-F | ggcgagctcacacaggaaacagaccatgaacgttattgcaatattgaatcac (SEQ ID NO: 35) |
| cadA-R | ggctctagaccacttcccttgtacgagc (SEQ ID NO: 36) |
| cadA-F2 | atttcacacaggaaacagctatgaacgttattgcaatattgaat (SEQ ID NO: 37) |
| cadA-R2 | agctgtttcctgtgtgaaat (SEQ ID NO: 38) |
| bdcA-F | ggcgagctctaaatcaaggagtccttatgggc (SEQ ID NO: 39) |
| bdcA-R | ggctctagagcttaattgagcgtagtcggtta (SEQ ID NO: 40) |
| bdcA-F2 | atttcacacaggaaacagctatgggcgcttttacaggtaag (SEQ ID NO: 41) |
| bdcA-R2 | agctgtttcctgtgtgaaat (SEQ ID NO: 42) |
| bdcA-F3 | ggctctagaacacaggaaacagaccatgggcgcttttacaggtaag (SEQ ID NO: 43) |
| bdcA-R3 | ggcaagcttgcttaattgagcgtagtcggtt (SEQ ID NO: 44) |
| yahA-F | ggcgagctcccataggtagaagtatgaattcatgtgattttcgtg (SEQ ID NO: 45) |
| yahA-R | ggctctagatcaaccacctgctttcatta (SEQ ID NO: 46) |
| yahA-F2 | atttcacacaggaaacagctatgaattcatgtgattttcgtg (SEQ ID NO: 47) |
| yahA-R2 | agctgtttcctgtgtgaaat (SEQ ID NO: 48) |
| yahA-F3 | ggctctagaacacaggaaacagaccatgaattcatgtgattttcgtg (SEQ ID NO: 49) |
| yahA-R3 | ggcaagctttcaaccacctgctttcatta (SEQ ID NO: 50) |
| psyn-1 | ggcgaattcagtttattcttgacatgtagtgaggggggctggtataatgagctcggtacccggggat (SEQ ID NO: 51) |
| psyn-2 | ggcagtactcaaccaagtcattctgagaatagtg (SEQ ID NO: 52) |
| tetA-F | ggcgagctcacacaggaaacagaccatgaaatctaacaatgcgctcatc (SEQ ID NO: 53) |
| tetA-R | ggctctagatcaacgacaggagcacgatc (SEQ ID NO: 54) |
| lysC-F | ggcgagctcacacaggaaacagaccatgtctgaaattgttgtctcc (SEQ ID NO: 55) |
| lysC-R | ggcggatccttactcaaacaaattactatgcag (SEQ ID NO: 56) |
| dapA-F | ggcggatccacacaggaaacagaccatgttcacgggaagtattgtc (SEQ ID NO: 57) |

Table of primer sequences used in Examples.

| Name | Sequence (5'-3') |
|---|---|
| dapA-R | ggctctagattacagcaaaccggcatgc (SEQ ID NO: 58) |
| lysA-F | ggctctagaacacaggaaacagaccatgccacattcact gttcagc (SEQ ID NO: 59) |
| lysA-R | ggcgtcgacttaaagcaattccagcgccag (SEQ ID NO: 60) |
| tetA-F3 | ggcctcgagagtttattcttgacatgtagtgagg (SEQ ID NO: 61) |
| tetA-R3 | ggcgcatgctcaacgacaggagcacgatc (SEQ ID NO: 62) |
| 318-F | cagcctgaatatactgcattctc (SEQ ID NO: 63) |
| 318-R | gagaatgcagtatattcaggctg (SEQ ID NO: 64) |
| 323-F | gcattctcgcgatttcctcg (SEQ ID NO: 65) |
| 323-R | cgaggaaatcgcgagaatgc (SEQ ID NO: 66) |
| SlysC-F | ggcgagctcacacaggaaacagaccatgggcttagttgt gcagaaa (SEQ ID NO: 67) |
| SlysC-R | ggcggatccttaacgacctgtgccgccata (SEQ ID NO: 68) |
| asd-F | ggcgagctcacacaggaaacagaccatgaaaaatgttggt tttatcgg (SEQ ID NO: 69) |
| asd-R | ggcggatccttacgccagttgacgaagc (SEQ ID NO: 70) |
| dapB-F | ggcacacaggaaacagaccatgcatgatgcaaacatccg (SEQ ID NO: 71) |
| dapB-R | ggctctagattacaaattattgagatcaagtacatctc- (SEQ ID NO: 72) |
| dapD-F | ggctctagaacacaggaaacagaccatgcagcagttaca gaacat (SEQ ID NO: 73) |
| dapD-R | ggcgcatgcttagtcgatggtacgcagca (SEQ ID NO: 74) |
| aspC-F | ggctctagaacacaggaaacagaccatgtttgagaacatt accgcc (SEQ ID NO: 75) |
| aspC-R | ggcgcatgcgacctcgaggtagtcgacttacagcactgcc acaatcg (SEQ ID NO: 76) |
| LAL-F | ggcggtaccagtttattcttgacatgtagtgagg (SEQ ID NO: 77) |
| LAL-R | ggcgggcccttaaagcaattccagcgcca (SEQ ID NO: 78) |
| ABC-F | ggcgggccctgctggccttttgctcacat (SEQ ID NO: 79) |
| ABCT-R | ggcggtacctcaacgacaggagcacgatc (SEQ ID NO: 80) |
| SAL-F | ggcggtaccagtttattcttgacatgtagtgagg (SEQ ID NO: 81) |
| SAL-R | ggcgggcccttaaagcaattccagcgcca (SEQ ID NO: 82) |

Illustrative Sequences

*Escherichia coli* cadA nucleic acid sequence
SEQ ID NO: 1

ATGAACGTTATTGCAATATTGAATCACATGGGGGTTTATTTTAAAGAAGAACCCATC
CGTGAACTTCATCGCGCGCTTGAACGTCTGAACTTCCAGATTGTTTACCCGAACGAC
CGTGACGACTTATTAAAACTGATCGAAAACAATGCGCGTCTGTGCGGCGTTATTTTT
GACTGGGATAAATATAATCTCGAGCTGTGCGAAGAAATTAGCAAAATGAACGAGAA
CCTGCCGTTGTACGCGTTCGCTAATACGTATTCCACTCTCGATGTAAGCCTGAATGA
CCTGCGTTTACAGATTAGCTTCTTTGAATATGCGCTGGGTGCTGCTGAAGATATTGCT
AATAAGATCAAGCAGACCACTGACGAATATATCAACACTATTCTGCCTCCGCTGACT
AAAGCACTGTTTAAATATGTTCGTGAAGGTAAATATACTTTCTGTACTCCTGGTCAC
ATGGGCGGTACTGCATTCCAGAAAAGCCCGGTAGGTAGCCTGTTCTATGATTTCTTT
GGTCCGAATACCATGAAATCTGATATTTCCATTTCAGTATCTGAACTGGGTTCTCTGC
TGGATCACAGTGGTCCACACAAAGAAGCAGAACAGTATATCGCTCGCGTCTTTAAC
GCAGACCGCAGCTACATGGTGACCAACGGTACTTCCACTGCGAACAAATTGTTGGT
ATGTACTCTGCTCCAGCAGGCAGCACCATTCTGATTGACCGTAACTGCCACAAATCG
CTGACCCACCTGATGATGATGAGCGATGTTACGCCAATCTATTTCCGCCCGACCCGT
AACGCTTACGGTATTCTTGGTGGTATCCCACAGAGTGAATTCCAGCACGCTACCATT
GCTAAGCGCGTGAAAGAAACACCAAACGCAACCTGGCCGGTACATGCTGTAATTAC
CAACTCTACCTATGATGGTCTGCTGTACAACACCGACTTCATCAAGAAAACACTGGA

-continued

```
TGTGAAATCCATCCACTTTGACTCCGCGTGGGTGCCTTACACCAACTTCTCACCGATT

TACGAAGGTAAATGCGGTATGAGCGGTGGCCGTGTAGAAGGGAAAGTGATTTACGA

AACCCAGTCCACTCACAAACTGCTGGCGGCGTTCTCTCAGGCTTCCATGATCCACGT

TAAAGGTGACGTAAACGAAGAAACCTTTAACGAAGCCTACATGATGCACACCACCA

CTTCTCCGCACTACGGTATCGTGGCGTCCACTGAAACCGCTGCGGCGATGATGAAAG

GCAATGCAGGTAAGCGTCTGATCAACGGTTCTATTGAACGTGCGATCAAATTCCGTA

AAGAGATCAAACGTCTGAGAACGGAATCTGATGGCTGGTTCTTTGATGTATGGCAGC

CGGATCATATCGATACGACTGAATGCTGGCCGCTGCGTTCTGACAGCACCTGGCACG

GCTTCAAAAACATCGATAACGAGCACATGTATCTTGACCCGATCAAAGTCACCCTGC

TGACTCCGGGGATGGAAAAAGACGGCACCATGAGCGACTTTGGTATTCCGGCCAGC

ATCGTGGCGAAATACCTCGACGAACATGGCATCGTTGTTGAGAAAACCGGTCCGTAT

AACCTGCTGTTCCTGTTCAGCATCGGTATCGATAAGACCAAAGCACTGAGCCTGCTG

CGTGCTCTGACTGACTTTAAACGTGCGTTCGACCTGAACCTGCGTGTGAAAAACATG

CTGCCGTCTCTGTATCGTGAAGATCCTGAATTCTATGAAAACATGCGTATTCAGGAA

CTGGCTCAGAATATCCACAAACTGATTGTTCACCACAATCTGCCGGATCTGATGTAT

CGCGCATTTGAAGTGCTGCCGACGATGGTAATGACTCCGTATGCTGCATTCCAGAAA

GAGCTGCACGGTATGACCGAAGAAGTTTACCTCGACGAAATGGTAGGTCGTATTAA

CGCCAATATGATCCTTCCGTACCCGCCGGGAGTTCCTCTGGTAATGCCGGGTGAAAT

GATCACCGAAGAAAGCCGTCCGGTTCTGGAGTTCCTGCAGATGCTGTGTGAAATCGG

CGCTCACTATCCGGGCTTTGAAACCGATATTCACGGTGCATACCGTCAGGCTGATGG

CCGCTATACCGTTAAGGTATTGAAAGAAGAAAGCAAAAAATAA
```

CadA polypeptide sequence
SEQ ID NO: 2

```
MNVIAILNHMGVYFKEEPIRELHRALERLNFQIVYPNDRDDLLKLIENNARLCGVIFDWD

KYNLELCEEISKMNENLPLYAFANTYSTLDVSLNDLRLQISFFEYALGAAEDIANKIKQT

TDEYINTILPPLTKALFKYVREGKYTFCTPGHMGGTAFQKSPVGSLFYDFFGPNTMKSDI

SISVSELGSLLDHSGPHKEAEQYIARVFNADRSYMVTNGTSTANKIVGMYSAPAGSTILI

DRNCHKSLTHLMMMSDVTPIYFRPTRNAYGILGGIPQSEFQHATIAKRVKETPNATWPV

HAVITNSTYDGLLYNTDFIKKTLDVKSIHFDSAWVPYTNFSPIYEGKCGMSGGRVEGKVI

YETQSTHKLLAAFSQASMIHVKGDVNEETFNEAYMMHTTTSPHYGIVASTETAAAMMK

GNAGKRLINGSIERAIKFRKEIKRLRTESDGWFFDVWQPDHIDTTECWPLRSDSTWHGFK

NIDNEHMYLDPIKVTLLTPGMEKDGTMSDFGIPASIVAKYLDEHGIVVEKTGPYNLLFLF

SIGIDKTKALSLLRALTDFKRAFDLNLRVKNMLPSLYREDPEFYENMRIQELAQNIHKLI

VHHNLPDLMYRAFEVLPTMVMTPYAAFQKELHGMTEEVYLDEMVGRINANMILPYPP

GVPLVMPGEMITEESRPVLEFLQMLCEIGAHYPGFETDIHGAYRQA

DGRYTVKVLKEESKK
```

E. coli bdcA nucleic acid sequence
SEQ ID NO: 3

```
ATGGGCGCTTTTACAGGTAAGACAGTTCTCATCCTCGGTGGCAGTCGTGGTATCGGT

GCCGCTATCGTACGTCGTTTCGTCACCGATGGGGCCAATGTACGATTCACCTATGCG

GGGTCGAAAGATGCCGCTAAACGCCTGGCACAAGAGACTGGAGCGACAGCAGTATT

CACAGATAGTGCTGACAGAGACGCTGTCATTGATGTCGTTCGTAAGAGCGGCGCATT

GGATATCCTGGTGGTAAATGCAGGTATTGGCGTCTTTGGCGAGGCCCTGGAATTAAA
```

-continued

```
TGCCGACGATATTGATCGCCTTTTCAAAATCAATATTCATGCTCCTTATCATGCCTCT
GTTGAAGCCGCCCGGCAGATGCCCGAAGGCGGGCGCATCTTAATCATCGGCTCCGT
GAATGGCGATCGTATGCCTGTTGCAGGCATGGCTGCTTATGCCGCCAGCAAATCTGC
CCTGCAAGGCATGGCGCGCGGGCTGGCCCGTGATTTTGGACCGCGTGGGATCACCA
TTAACGTCGTCCAGCCAGGGCCAATTGATACCGACGCTAATCCCGCCAACGGGCCA
ATGCGCGATATGTTGCATAGTTTGATGGCTATCAAAAGACATGGGCAACCGGAAGA
GGTCGCTGGTATGGTCGCATGGTTAGCAGGGCCAGAAGCCAGTTTTGTTACCGGCGC
GATGCATACCATTGATGGCGCGTTTGGCGCATAA
```

BdcA polypeptide sequence

SEQ ID NO: 4

```
MGAFTGKTVLILGGSRGIGAAIVRRFVTDGANVRFTYAGSKDAAKRLAQE
TGATAVFTDSADRDAVIDVVRKSGALDILVVNAGIGVFGEALELNADDID
RLFKINIHAPYHASVEAARQMPEGGRILIIGSVNGDRMPVAGMAAYAASK
SALQGMARGLARDFGPRGITINVVQPGPIDTDANPANGPMRDMLHSLMAI
KRHGQPEEVAGMVAWLAGPEASFVTGAMHTIDGAFGA
```

E. coli yahA nucleic acid sequence

SEQ ID NO: 5

```
ATGAATTCATGTGATTTTCGTGTTTTTCTGCAAGAGTTCGGTACAACGGTTCATTTGT
CATTGCCTGGTAGCGTATCCGAGAAAGAACGACTGCTACTCAAGCTGCTGATGCAG
GGAATGTCTGTAACAGAAATATCACAGTACAGAAATCGCAGTGCAAAGACAATTTC
ACATCAAAAGAAACAGCTCTTTGAGAAACTGGGGATTCAGAGCGATATTACTTTCTG
GCGCGATATTTTCTTTCAGTACAATCCGGAGATCATATCCGCCACGGGGAGTAATAG
TCACAGATATATTAATGATAATCACTATCACCATATCGTCACGCCTGAAGCCATCAG
TCTGGCGTTGGAAAACCACGAATTCAAACCGTGGATCCAACCGGTTTTCTGCGCGCA
GACTGGCGTACTGACGGGCTGTGAGGTGCTTGTCCGCTGGGAACATCCACAAACGG
GAATTATCCCACCGGATCAGTTTATTCCTCTGGCGGAGTCATCCGGTCTTATTGTCAT
AATGACCCGCCAACTGATGAAACAGACTGCGGATATTCTGATGCCGGTAAAACATTT
GCTGCCGGACAATTTCCATATTGGCATCAACGTCTCGGCGGGTTGTTTTTTGGCAGC
GGGATTTGAAAAAGAGTGTCTGAACCTGGTTAATAAATTAGGTAACGATAAAATCA
AGCTGGTTCTCGAGCTAACGGAACGTAACCCTATTCCGGTAACGCCAGAAGCCAGA
GCGATATTTGACAGCCTTCATCAGCACAACATTACCTTTGCGCTGGATGACTTTGGT
ACGGGTTATGCGACCTATCGTTACTTGCAGGCGTTCCCGGTCGATTTTATTAAGATC
GATAAGTCATTTGTGCAAATGGCGAGTGTCGACGAAATCTCCGGTCATATTGTGGAC
AATATTGTCGAACTAGCGCGTAAGCCTGGTCTGAGTATCGTGGCGGAAGGGGTAGA
AACCCAGGAGCAGGCGGATTTAATGATCGGTAAAGGCGTTCACTTTTTGCAGGGCTA
TTTGTACTCTCCGCCAGTACCGGGTAATAAATTTATCTCTGAATGGGTAATGAAAGC
AGGTGGTTGA
```

YahA polypeptide sequence

SEQ ID NO: 6

```
MNSCDFRVFLQEFGTTVHLSLPGSVSEKERLLLKLLMQGMSVTEISQYRN
RSAKTISHQKKQLFEKLGIQSDITFWRDIFFQYNPEIISATGSNSHRYIN
DNHYHHIVTPEAISLALENHEFKPWIQPVFCAQTGVLTGCEVLVRWEHPQ
TGIIPPDQFIPLAESSGLIVIMTRQLMKQTADILMPVKHLLPDNFHGIN
```

-continued

VSAGCFLAAGFEKECLNLVNKLGNDKIKLVLELTERNPIPVTPEARAIFD

SLHQHNITFALDDFGTGYATYRYLQAFPVDFIKIDKSFVQMASVDEISGH

IVDNIVELARKPGLSIVAEGVETQEQADLMIGKGVHFLQGYLYSPPVPGN

KFISEWVMKAGG synthetic promoter nucleic acid sequence
SEQ ID NO: 7
AGTTTATTCTTGACATGTAGTGAGGGGGCTGGTATAAT tetA nucleic acid sequence
SEQ ID NO: 8
ATGAAATCTAACAATGCGCTCATCGTCATCCTCGGCACCGTCACCCTGGATGCTGTA

GGCATAGGCTTGGTTATGCCGGTACTGCCGGGCCTCTTGCGGGATATCGTCCATTCC

GACAGCATCGCCAGTCACTATGGCGTGCTGCTAGCGCTATATGCGTTGATGCAATTT

CTATGCGCACCCGTTCTCGGAGCACTGTCCGACCGCTTTGGCCGCCGCCCAGTCCTG

CTCGCTTCGCTACTTGGAGCCACTATCGACTACGCGATCATGGCGACCACACCCGTC

CTGTGGATCCTCTACGCCGGACGCATCGTGGCCGGCATCACCGGCGCCACAGGTGC

GGTTGCTGGCGCCTATATCGCCGACATCACCGATGGGGAAGATCGGGCTCGCCACTT

CGGGCTCATGAGCGCTTGTTTCGGCGTGGGTATGGTGGCAGGCCCCGTGGCCGGGG

GACTGTTGGGCGCCATCTCCTTGCATGCACCATTCCTTGCGGCGGCGGTGCTCAACG

GCCTCAACCTACTACTGGGCTGCTTCCTAATGCAGGAGTCGCATAAGGGAGAGCGTC

GACCGATGCCCTTGAGAGCCTTCAACCCAGTCAGCTCCTTCCGGTGGGCGCGGGCA

TGACTATCGTCGCCGCACTTATGACTGTCTTCTTTATCATGCAACTCGTAGGACAGGT

GCCGGCAGCGCTCTGGGTCATTTTCGGCGAGGACCGCTTTCGCTGGAGCGCGACGAT

GATCGGCCTGTCGCTTGCGGTATTCGGAATCTTGCACGCCCTCGCTCAAGCCTTCGT

CACTGGTCCCGCCACCAAACGTTTCGGCGAGAAGCAGGCCATTATCGCCGGCATGG

CGGCCGACGCGCTGGGCTACGTCTTGCTGGCGTTCGCGACGCGAGGCTGGATGGCCT

TCCCCATTATGATTCTTCTCGCTTCCGGCGGCATCGGGATGCCCGCGTTGCAGGCCA

TGCTGTCCAGGCAGGTAGATGACGACCATCAGGGACAGCTTCAAGGATCGCTCGCG

GCTCTTACCAGCCTAACTTCGATCATTGGACCGCTGATCGTCACGGCGATTTATGCC

GCCTCGGCGAGCACATGGAACGGGTTGGCATGGATTGTAGGCGCCGCCCTATACCTT

GTCTGCCTCCCCGCGTTGCGTCGCGGTGCATGGAGCCGGGCCACCTCGACCTGA

TetA polypeptide sequence
SEQ ID NO: 9
MKSNNALIVILGTVTLDAVGIGLVMPVLPGLLRDIVHSDSIASHYGVLLALYALMQFLC

APVLGALSDRFGRRPVLLASLLGATIDYAIMATTPVLWILYAGRIVAGITGATGAVAGA

YIADITDGEDRARHFGLMSACFGVGMVAGPVAGGLLGAISLHAPFLAAAVLNGLNLLL

GCFLMQESHKGERRPMPLRAFNPVSSFRWARGMTIVAALMTVFFINIQLVGQVPAALW

VIFGEDRFRWSATMIGLSLAVFGILHALAQAFVTGPATKRFGEKQAIIAGMAADALGYV

LLAFATRGWMAFPIMILLASGGIGMPALQAMLSRQVDDDHQGQLQGSLAALTSLTSIIG

PLIVTAIYAASASTWNGLAWIVGAALYLVCLPALRRGAWSRATST lysC nucleic acid sequence
SEQ ID NO: 10
ATGTCTGAAATTGTTGTCTCCAAATTTGGCGGTACCAGCGTAGCTGATTTTGACGCC

ATGAACCGCAGCGCTGATATTGTGCTTTCTGATGCCAACGTGCGTTTAGTTGTCCTCT

CGGCTTCTGCTGGTATCACTAATCTGCTGGTCGCTTTAGCTGAAGGACTGGAAC CTG

GCGAGCGATTCGAAAAACTCGACGCTATCCGCAACATCCAGTTTGCCATTCTGGAAC

-continued

```
GTCTGCGTTACCCGAACGTTATCCGTGAAGAGATTGAACGTCTGCTGGAGAACATTA
CTGTTCTGGCAGAAGCGGCGGCGCTGGCAACGTCTCCGGCGCTGACAGATGAGCTG
GTCAGCCACGGCGAGCTGATGTCGACCCTGCTGTTTGTTGAGATCCTGCGCGAACGC
GATGTTCAGGCACAGTGGTTTGATGTACGTAAAGTGATGCGTACCAACGACCGATTT
GGTCGTGCAGAGCCAGATATAGCCGCGCTGGCGGAACTGGCCGCGCTGCAGCTGCT
CCCACGTCTCAATGAAGGCTTAGTGATCACCCAGGGATTTATCGGTAGCGAAAATAA
AGGTCGTACAACGACGCTTGGCCGTGGAGGCAGCGATTATACGGCAGCCTTGCTGG
CGGAGGCTTTACACGCATCTCGTGTTGATATCTGGACCGACGTCCCGGGCATCTACA
CCACCGATCCACGCGTAGTTTCCGCAGCAAAACGCATTGATGAAATCGCGTTTGCCG
AAGCGGCAGAGATGGCAACTTTTGGTGCAAAAGTACTGCATCCGGCAACGTTGCTA
CCCGCAGTACGCAGCGATATCCCGGTCTTTGTCGGCTCCAGCAAAGACCCACGCGCA
GGTGGTACGCTGGTGTGCAATAAAACTGAAAATCCGCCGCTGTTCCGCGCTCTGGCG
CTTCGTCGCAATCAGACTCTGCTCACTTTGCACAGCCTGAATATGCTGCATTCTCGCG
GTTTCCTCGCGGAAGTTTTCGGCATCCTCGCGCGGCATAATATTTCGGTAGACTTAAT
CACCACGTCAGAAGTGAGCGTGGCATTAACCCTTGATACCACCGGTTCAACCTCCAC
TGGCGATACGTTGCTGACGCAATCTCTGCTGATGGAGCTTTCCGCACTGTGTCGGGT
GGAGGTGGAAGAAGGTCTGGCGCTGGTCGCGTTGATTGGCAATGACCTGTCAAAAG
CCTGCGGCGTTGGCAAAGAGGTATTCGGCGTACTGGAACCGTTCAACATTCGCATGA
TTTGTTATGGCGCATCCAGCCATAACCTGTGCTTCCTGGTGCCCGGCGAAGATGCCG
AGCAGGTGGTGCAAAAACTGCATAGTAATTTGTTTGAGTAA
```

LysC polypeptide sequence
SEQ ID NO: 11
```
MSEIVVSKFGGTSVADFDAMNRSADIVLSDANVRLVVLSASAGITNLLVALAEGLEPGE
RFEKLDAIRNIQFAILERLRYPNVIREEIERLLENITVLAEAAALATSPALTDELVSHGELM
STLLFVEILRERDVQAQWFDVRKVMRTNDRFGRAEPDIAALAELAALQLLPRLNEGLVI
TQGFIGSENKGRTTTLGRGGSDYTAALLAEALHASRVDIWTDVPGIYTTDPRVVSAAKRI
DEIAFAEAAEMATFGAKVLHPATLLPAVRSDIPVFVGSSKDPRAGGTLVCNKTENPPLFR
ALALRRNQTLLTLHSLNMLHSRGFLAEVFGILARHNISVDLITTSEVSVALTLDTTGSTST
GDTLLTQSLLMELSALCRVEVEEGLALVALIGNDLSKACGVGKEVFGVLEPFNIRMICY
GASSHNLCFLVPGEDAEQVVQKLHSNLFE
``` dapA nucleic acid sequence
SEQ ID NO: 12
```
ATGTTCACGGGAAGTATTGTCGCGATTGTTACTCCGATGGATGAAAAAGGTAATGTC
TGTCGGGCTAGCTTGAAAAAACTGATTGATTATCATGTCGCCAGCGGTACTTCGGCG
ATCGTTTCTGTTGGCACCACTGGCGAGTCCGCTACCTTAAATCATGACGAACATGCT
GATGTGGTGATGATGACGCTGGATCTGGCTGATGGGCGCATTCCGGTAATTGCCGGG
ACCGGCGCTAACGCTACTGCGGAAGCCATTAGCCTGACGCAGCGCTTCAATGACAG
TGGTATCGTCGGCTGCCTGACGGTAACCCCTTACTACAATCGTCCGTCGCAAGAAGG
TTTGTATCAGCATTTCAAAGCCATCGCTGAGCATACTGACCTGCCGCAAATTCTGTA
TAATGTGCCGTCCCGTACTGGCTGCGATCTGCTCCCGGAAACGGTGGGCCGTCTGGC
GAAAGTAAAAAATATTATCGGAATCAAAGAGGCAACAGGGAACTTAACGCGTGTAA
ACCAGATCAAAGAGCTGGTTTCAGATGATTTTGTTCTGCTGAGCGGCGATGATGCGA
```

-continued

```
GCGCGCTGGACTTCATGCAATTGGGCGGTCATGGGGTTATTTCCGTTACGGCTAACG

TCGCAGCGCGTGATATGGCCCAGATGTGCAAACTGGCAGCAGAAGGGCATTTTGCC

GAGGCACGCGTTATTAATCAGCGTCTGATGCCATTACACAACAAACTATTTGTCGAA

CCCAATCCAATCCCGGTGAAATGGGCATGTAAGGAACTGGGTCTTGTGGCGACCGA

TACGCTGCGCCTGCCAATGACACCAATCACCGACAGTGGTCGTGAGACGGTCAGAG

CGGCGCTTAAGCATGCCGGTTTGCTGTAA
```

DapA polypeptide sequence

SEQ ID NO: 13

```
MFTGSIVAIVTPMDEKGNVCRASLKKLIDYHVASGTSAIVSVGTTGESATLNHDEHADV

VMMTLDLADGRIPVIAGTGANATAEAISLTQRFNDSGIVGCLTVTPYYNRPSQEGLYQH

FKAIAEHTDLPQILYNVPSRTGCDLLPETVGRLAKVKNIIGIKEATGNLTRVNQIKELVSD

DFVLLSGDDASALDFMQLGGHGVISVTANVAARDMAQMCKLAAEGHFAEARVINQRL

MPLHNKLFVEPNPIPVKWACKELGLVATDTLRLPMTPITDSGRETVRAALKHAGLL
``` lysA nucleic acid sequence

SEQ ID NO: 14

```
ATGCCACATTCACTGTTCAGCACCGATACCGATCTCACCGCCGAAAATCTGCTGCGT

TTGCCCGCTGAATTTGGCTGCCCGGTGTGGGTCTACGATGCGCAAATTATTCGTCGG

CAGATTGCAGCGCTGAAACAGTTTGATGTGGTGCGCTTTGCACAGAAAGCCTGTTCC

AATATTCATATTTTGCGCTTAATGCGTGAGCAGGGCGTGAAAGTGGATTCCGTCTCG

TTAGGCGAAATAGAGCGTGCGTTGGCGGCGGGTTACAATCCGCAAACGCACCCCGA

TGATATTGTTTTTACGGCAGATGTTATCGATCAGGCGACGCTTGAACGCGTCAGTGA

ATTGCAAATTCCGGTGAATGCGGGTTCTGTTGATATGCTCGACCAACTGGGCCAGGT

TTCGCCAGGGCATCGGGTATGGCTGCGCGTTAATCCGGGGTTTGGTCACGGACATAG

CCAAAAAACCAATACCGGTGGCGAAAACAGCAAGCACGGTATCTGGTACACCGATC

TGCCCGCCGCACTGGACGTGATACAACGTCATCATCTGCAGCTGGTCGGCATTCACA

TGCACATTGGTTCTGGCGTTGATTATGCCCATCTGGAACAGGTGTGTGGTGCTATGG

TGCGTCAGGTCATCGAATTCGGTCAGGATTTACAGGCTATTTCTGCGGGCGGTGGGC

TTTCTGTTCCTTATCAACAGGGTGAAGAGGCGGTTGATACCGAACATTATTATGGTC

TGTGGAATGCCGCGCGTGAGCAAATCGCCCGCCATTTGGGCCACCCTGTGAAACTG

GAAATTGAACCGGGTCGCTTCCTGGTAGCGCAGTCTGGCGTATTAATTACTCAGGTG

CGGAGCGTCAAACAAATGGGGAGCCGCCACTTTGTGCTGGTTGATGCCGGGTTCAA

CGATCTGATGCGCCCGGCAATGTACGGTAGTTACCACCATATCAGTGCCCTGGCAGC

TGATGGTCGTTCTCTGGAACACGCGCCAACGGTGGAAACCGTCGTCGCCGGACCGTT

ATGTGAATCGGGCGATGTCTTTACCCAGCAGGAAGGGGGAAATGTTGAAACCCGCG

CCTTGCCGGAAGTGAAGGCAGGTGATTATCTGGTACTGCATGATACAGGGGCATAT

GGCGCATCAATGTCATCCAACTACAATAGCCGTCCGCTGTTACCAGAAGTTCTGTTT

GATAATGGTCAGGCGCGGTTGATTCGCCGTCGCCAGACCATCGAAGAATTACTGGC

GCTGGAATTGCTTTAA
```

LysA polypeptide sequence

SEQ ID NO: 15

```
MPHSLFSTDTDLTAENLLRLPAEFGCPVWVYDAQIIRRQIAALKQFDVVRFAQKACSNIH

ILRLMREQGVKVDSVSLGEIERALAAGYNPQTHPDDIVFTADVIDQATLERVSELQIPVN

AGSVDMLDQLGQVSPGHRVWLRVNPGFGHGHSQKTNTGGENSKHGIWYTDLPAALDV

IQRHHLQLVGIHMHIGSGVDYAHLEQVCGAMVRQVIEFGQDLQAISAGGGLSVPYQQG
```

EEAVDTEHYYGLWNAAREQIARHLGHPVKLEIEPGRFLVAQSGVLITQVRSVKQMGSR

HFVLVDAGFNDLMRPAMYGSYHHISALAADGRSLEHAPTVETVVAGPLCESGDVFTQQ

EGGNVETRALPEVKAGDYLVLHDTGAYGASMSSNYNSRPLLPEVLFDNGQARLIRRRQ

TIEELLALELL lysC-1 nucleic acid sequence

SEQ ID NO: 16

ATGTCTGAAATTGTTGTCTCCAAATTTGGCGGTACCAGCGTAGCTGATTTTGACGCC

ATGAACCGCAGCGCTGATATTGTGCTTTCTGATGCCAACGTGCGTTTAGTTGTCCTCT

CGGCTTCTGCTGGTATCACTAATCTGCTGGTCGCTTTAGCTGAAGGACTGGAACCTG

GCGAGCGATTCGAAAAACTCGACGCTATCCGCAACATCCAGTTTGCCATTCTGGAAC

GTCTGCGTTACCCGAACGTTATCCGTGAAGAGATTGAACGTCTGCTGGAGAACATTA

CTGTTCTGGCAGAAGCGGCGGCGCTGGCAACGTCTCCGGCGCTGACAGATGAGCTG

GTCAGCCACGGCGAGCTGATGTCGACCCTGCTGTTTGTTGAGATCCTGCGCGAACGC

GATGTTCAGGCACAGTGGTTTGATGTACGTAAAGTGATGCGTACCAACGACCGATTT

GGTCGTGCAGAGCCAGATATAGCCGCGCTGGCGGAACTGGCCGCGCTGCAGCTGCT

CCCACGTCTCAATGAAGGCTTAGTGATCACCCAGGGATTTATCGGTAGCGAAAATAA

AGGTCGTACAACGACGCTTGGCCGTGGAGGCAGCGATTATACGGCAGCCTTGCTGG

CGGAGGCTTTACACGCATCTCGTGTTGATATCTGGACCGACGTCCCGGGCATCTACA

CCACCGATCCACGCGTAGTTTCCGCAGCAAAACGCATTGATGAAATCGCGTTTGCCG

AAGCGGCAGAGATGGCAACTTTTGGTGCAAAAGTACTGCATCCGGCAACGTTGCTA

CCCGCAGTACGCAGCGATATCCCGGTCTTTGTCGGCTCCAGCAAAGACCCACGCGCA

GGTGGTACGCTGATGTGCAATAAAACTGAAAATCCGCCGCTGTTCCGCGCTCTGGCG

CTTCGTCGCAATCAGACTCTGCTCACTTTGCACAGCCTGAATATACTGCATTCTCGCG

ATTTCCTCGCGGAAGTTTTCGGCATCCTCGCGCGGCATAATATTTCGGTAGACTTAAT

CACCACGTCAGAAGTGAGCGTGGCATTAACCCTTGATACCACCGGTTCAACCTCCAC

TGGCGATACGTTGCTGACGCAATCTCTGCTGATGGAGCTTTCCGCACTGTGTCGGGT

GGAGGTGGAAGAAGGTCTGGCGCTGGTCGCGTTGATTGGCAATGACCTGCCAAAAG

CCTGCGGCGTTGGCAAAGAGGTATTCGGCGTACTGGAACCGTTCAACATTCGCATGA

TTTGTTATGGCGCATCCAGCCATAACCTGTGCTTCCTGGTGCCCGGCGAAGATGCCG

AGCAGGTGGTGCAAAAACTGCATAGTAATTTGTTTGAGTAA

LysC-1 polypeptide sequence

SEQ ID NO: 17

MSEIVVSKFGGTSVADFDAMNRSADIVLSDANVRLVVLSASAGITNLLVALAEGLEPGE

RFEKLDAIRNIQFAILERLRYPNVIREEIERLLENITVLAEAAALATSPALTDELVSHGELM

STLLFVEILRERDVQAQWFDVRKVMRTNDRFGRAEPDIAALAELAALQLLPRLNEGLVI

TQGFIGSENKGRTTTLGRGGSDYTAALLAEALHASRVDIWTDVPGIYTTDPRVVSAAKRI

DEIAFAEAAEMATFGAKVLHPATLLPAVRSDIPVFVGSSKDPRAGGTLVCNKTENPPLFR

ALALRRNQTLLTLHSLNILHSRDFLAEVFGILARHNISVDLITTSEVSVALTLDTTGSTSTG

DTLLTQSLLMELSALCRVEVEEGLALVALIGNDLSKACGVGKEVFGVLEPFNIRMICYG

ASSHNLCFLVPGEDAEQVVQKLHSNLFE

-continued

S-lysC nucleic acid sequence
SEQ ID NO: 18
ATGGGCTTAGTTGTGCAGAAATACGGCGGTAGTAGCGTGGCCGATGCCGAAGGCAT

CAAACGTGTTGCCAAACGCATTGTTGAAGCCAAAAAGAATGGTAATCAGGTTGTGG

TTGTCGTTTCAGCAATGGGCGATACCACAGATGAACTTATTGATCTGGCCCAGGAAG

TTAGCCCGATTCCGAGCGGTCGTGAATTTGATATGTTACTTACAGCCGGTGAACGTA

TTAGCATGGCCTTACTGGCCATGGCAATCAAAAATCTGGGTCACGAAGCCCAGAGCT

TCACAGGTTCACAGGCCGGTGTTATTACAGATAGCGTTCATAATAAAGCGCGCATTA

TCGATGTTACCCCGGGTCGTATTAAAGCAAGCCTGGATGAAGGCAACATCGCCATTG

TGGCAGGCTTTCAGGGTGTTAGCCAGGATAAAAAGGATATTACCACACTGGGTCGC

GGTGGCAGCGATACAACGGCAGTGGCCCTGGCAGCCGCATTAAATGCAGATGTTTG

TGAAATCTATACCGATGTTGATGGTGTTTTTACCGCAGATCCGCGCGTGGTTAAGAA

AGCCCGTAAAATTGAATGGATCTCATTCGAAGATATGCTGGAATTAGCCAGCAGCG

GTAGCAAAGTTCTGCTGCATCGTTGTGTTGAATATGCACGCCGTTACAATATTCCTAT

TCATGTTCGTTCAAGTTTTTCAGGTTTACAGGGCACATGGGTTAGCAATGAACCGCA

GGGTGATCGTCCGATGGAACAGGCAATCATTAGCGGTGTTGCACATGATACCTCAG

AAGCAAAAGTTACCGTTGTTGGTGTTCCGGATAAACCGGGCGAAGCAGCACGTATC

TTTCGGGCCATTGCCGATTCAGAAGTGAATATCGACATGGTGGTTCAGAATGTTAGC

GCAGCAAGCACCGGTCTGACCGATATTAGCTTTACCCTGCCGAAAGCAGAAGGTCG

TAAAGCAGTTGCAGCACTGGAGAAAACCCGTGCAGCCGTGGGCTTTGATAGTTTAC

GGTATGATGATCAGATTGCAAAAATTAGCCTGGTTGGTGCAGGTATGAAAACCAAT

CCGGGTGTGACCGCAACCTTTTTTGAAGCATTAAGCAATGCAGGCGTTAATATTGAA

CTGATTAGCACCAGTGAAATTCGTATCAGCGTTGTGACCCGCGCAGATGATGTTAAT

GAAGCCGTTCAGGCAGTTCATAGCGCATTTGGTCTGGATAGCGAAACCGATGAAGC

AGTGGTTTATGGCGGCACAGGTCGTTAA

S-LysC polypeptide sequence
SEQ ID NO: 19
MGLVVQKYGGSSVADAEGIKRVAKRIVEAKKNGNQVVAVVSAMGDTTDELIDLAEQV

SPIPAGRELDMLLTAGERISMALLAMAIKNLGREAQSFTGSQAGVITDSVHNKARIIDVT

PGRIRTSVDEGNVAIVAGFQGVSQDSKDITTLGRGGSDTTAVALAAALDADVCEIYTDV

DGVFTADPRVVPKAKKIDWISFEDMLELAASGSKVLLHRCVEYARRYNIPIHVRSSFSGL

QGTWVSSEPIKQGEKHVEQALISGVAHDTSEAKVTVVGVPDKPGEAAAIFRAIADAQVN

IDMVVQNVSAASTGLTDISFTLPKSEGRKAIDALEKNRPGIGFDSLRYDDQIGKISLVGAG

MKSNPGVTADFFTALSDAGVNIELISTSEIRISVVTRKDDVNEAVRAVHTAFGLDSDSDE

AVVYGGTGR asd nucleic acid sequence
SEQ ID NO: 20
ATGAAAAATGTTGGTTTTATCGGCTGGCGCGGTATGGTCGGCTCCGTTCTCATGCAA

CGCATGGTTGAAGAGCGCGACTTCGACGCCATTCGCCCTGTCTTCTTTTCTACTTCTC

AGCTTGGCCAGGCTGCGCCGTCTTTTGGCGGAACCACTGGCACACTTCAGGATGCCT

TTGATCTGGAGGCGCTAAAGGCCCTCGATATCATTGTGACCTGTCAGGGCGGCGATT

ATACCAACGAAATCTATCCAAAGCTTCGTGAAAGCGGATGGCAAGGTTACTGGATT

GACGCAGCATCGTCTCTGCGCATGAAAGATGACGCCATCATCATTCTTGACCCCGTC

```
AATCAGGACGTCATTACCGACGGATTAAATAATGGCATCAGGACTTTTGTTGGCGGT

AACTGTACCGTAAGCCTGATGTTGATGTCGTTGGGTGGTTTATTCGCCAATGATCTTG

TTGATTGGGTGTCCGTTGCAACCTACCAGGCCGCTTCCGGCGGTGGTGCGCGACATA

TGCGTGAGTTATTAACCCAGATGGGCCATCTGTATGGCCATGTGGCAGATGAACTCG

CGACCCCGTCCTCTGCTATTCTCGATATCGAACGCAAAGTCACAACCTTAACCCGTA

GCGGTGAGCTGCCGGTGGATAACTTTGGCGTGCCGCTGGCGGGTAGCCTGATTCCGT

GGATCGACAAACAGCTCGATAACGGTCAGAGCCGCGAAGAGTGGAAAGGGCAGGC

GGAAACCAACAAGATCCTCAACACATCTTCCGTAATTCCGGTAGATGGTTTATGTGT

GCGTGTCGGGGCATTGCGCTGCCACAGCCAGGCATTCACTATTAAATTGAAAAAAG

ATGTGTCTATTCCGACCGTGGAAGAACTGCTGGCTGCGCACAATCCGTGGGCGAAA

GTCGTTCCGAACGATCGGGAAATCACTATGCGTGAGCTAACCCCAGCTGCCGTTACC

GGCACGCTGACCACGCCGGTAGGCCGCCTGCGTAAGCTGAATATGGGACCAGAGTT

CCTGTCAGCCTTTACCGTGGGCGACCAGCTGCTGTGGGGGCCGCGGAGCCGCTGC

GTCGGATGCTTCGTCAACTGGCGTAA
```

Asd polypeptide sequence
                                                                   SEQ ID NO: 21
```
MKNVGFIGWRGMVGSVLMQRMVEERDFDAIRPVFFSTSQLGQAAPSFGGTTGTLQDAF

DLEALKALDIIVTCQGGDYTNEIYPKLRESGWQGYWIDAASSLRMKDDAIIILDPVNQDV

ITDGLNNGIRTFVGGNCTVSLMLMSLGGLFANDLVDWVSVATYQAASGGGARHMREL

LTQMGHLYGHVADELATPSSAILDIERKVTTLTRSGELPVDNFGVPLAGSLIPWIDKQLD

NGQSREEWKGQAETNKILNTSSVIPVDGLCVRVGALRCHSQAFTIKLKKDVSIPTVEELL

AAHNPWAKVVPNDREITMRELTPAAVTGTLTTPVGRLRKLNMGPEFLSAFTVGDQ
``` dapB nucleic acid sequence
                                                                   SEQ ID NO: 22
```
ATGCATGATGCAAACATCCGCGTTGCCATCGCGGGAGCCGGGGGCGTATGGGCCG

CCAGTTGATTCAGGCGGCGCTGGCATTAGAGGGCGTGCAGTTGGGCGCTGCGCTGG

AGCGTGAAGGATCTTCTTTACTGGGCAGCGACGCCGGTGAGCTGGCCGGAGCCGGG

AAAACAGGCGTTACCGTGCAAAGCAGCCTCGATGCGGTAAAAGATGATTTTGATGT

GTTTATCGATTTTACCCGTCCGGAAGGTACGCTGAACCATCTCGCTTTTTGTCGCCAG

CATGGCAAAGGGATGGTGATCGGCACTACGGGGTTTGACGAAGCCGGTAAACAAGC

AATTCGTGACGCCGCTGCCGATATTGCGATTGTCTTTGCTGCCAATTTTAGCGTTGGC

GTTAACGTCATGCTTAAGCTGCTGGAGAAAGCAGCCAAAGTGATGGGTGACTACAC

CGATATCGAAATTATTGAAGCACATCATAGACATAAAGTTGATGCGCCGTCAGGCA

CCGCACTGGCAATGGGAGAGGCGATCGCCCACGCCCTTGATAAAGATCTGAAAGAT

TGCGCGGTCTACAGTCGTGAAGGCCACACCGGTGAACGTGTGCCTGGCACCATTGGT

TTTGCCACCGTGCGTGCAGGTGACATCGTTGGTGAACATACCGCGATGTTTGCCGAT

ATTGGCGAGCGTCTGGAGATCACCCATAAGGCGTCCAGCCGTATGACATTTGCTAAC

GGCGCGGTAAGATCGGCTTTGTGGTTGAGTGGTAAGGAAAGCGGTCTTTTTGATATG

CGAGATGTACTTGATCTCAATAATTTGTAA
```

DapB polypeptide sequence
                                                                   SEQ ID NO: 23
```
MHDANIRVAIAGAGGRMGRQLIQAALALEGVQLGAALEREGSSLLGSDAGELAGAGKT

GVTVQSSLDAVKDDFDVFIDFTRPEGTLNHLAFCRQHGKGMVIGTTGFDEAGKQAIRDA

AADIAIVFAANFSVGVNVMLKLLEKAAKVMGDYTDIEIIEAHHRHKVDAPSGTALAMG
```

EMAHALDKDLKDCAVYSREGHTGERVPGTIGFATVRAGDIVGEHTAMFADIGERLEIT

HKASSRMTFANGAVRSALWLSGKESGLFDMRDVLDLNNL dapD nucleic acid sequence

SEQ ID NO: 24

ATGCAGCAGTTACAGAACATTATTGAAACCGCTTTTGAACGCCGTGCCGAGATCACG

CCAGCCAATGCAGACACCGTTACCCGCGAAGCGGTAAATCAGGTGATCGCCCTGCT

GGATTCCGGCGCACTGCGTGTAGCGGAAAAAATTGACGGTCAGTGGGTGACGCATC

AGTGGTTGAAAAAAGCGGTGCTGCTCTCTTTCCGTATTAATGATAATCAGGTGATCG

AAGGGGCAGAAAGCCGCTACTTCGACAAAGTGCCGATGAAATTCGCCGACTACGAC

GAAGCACGTTTCCAGAAAGAAGGCTTCCGCGTTGTGCCACCAGCGGCGGTACGTCA

GGGTGCGTTTATTGCCCGTAACACCGTGCTGATGCCGTCTTACGTCAACATCGGCGC

ATATGTTGATGAAGGCACCATGGTTGATACCTGGGCGACCGTCGGTTCTTGTGCGCA

GATTGGTAAAAACGTCCACCTTTCCGGTGGCGTGGGCATCGGCGGCGTGCTGGAACC

GCTGCAGGCTAACCCAACCATCATTGAAGATAATTGCTTCATCGGCGCGCGCTCTGA

AGTGGTTGAAGGGGTGATTGTCGAAGAAGGTTCCGTCATTTCCATGGGCGTATACAT

TGGTCAGAGCACCCGTATTTACGACCGTGAAACCGGCGAAATCCACTACGGTCGCG

TTCCGGCGGGGTCTGTGGTTGTTTCAGGTAATCTGCCGTCAAAAGATGGCAAATACA

GCCTCTACTGTGCGGTTATCGTTAAGAAAGTTGACGCGAAAACTCGCGGCAAAGTCG

GCATTAACGAACTGCTGCGTACCATCGACTAA

DapD polypeptide sequence

SEQ ID NO: 25

MQQLQNIIETAFERRAEITPANADTVTREAVNQVIALLDSGALRVAEKIDGQWVTHQWL

KKAVLLSFRINDNQVIEGAESRYFDKVPMKFADYDEARFQKEGFRVVPPAAVRQGAFIA

RNTVLMPSYVNIGAYVDEGTMVDTWATVGSCAQIGKNVHLSGGVGIGGVLEPLQANPT

IIEDNCFIGARSEVVEGVIVEEGSVISMGVYIGQSTRIYDRETGEHIYGRVPAGSVVVSGN

LPSKDGKYSLYCAVIVKKVDAKTRGKVGINELLRTID aspC nucleic acid sequence

SEQ ID NO: 26

ATGTTTGAGAACATTACCGCCGCTCCTGCCGACCCGATTCTGGGCCTGGCCGATCTG

TTTCGTGCCGATGAACGTCCCGGCAAAATTAACCTCGGGATTGGTGTCTATAAAGAT

GAGACGGGCAAAACCCCGGTACTGACCAGCGTGAAAAAGGCTGAACAGTATCTGCT

CGAAAATGAAACCACCAAAAATTACCTCGGCATTGACGGCATCCCTGAATTTGGTCG

CTGCACTCAGGAACTGCTGTTTGGTAAAGGTAGCGCCCTGATCAATGACAAACGTGC

TCGCACGGCACAGACTCCGGGGGGCACTGGCGCACTACGCGTGGCTGCCGATTTCCT

GGCAAAAAATACCAGCGTTAAGCGTGTGTGGGTGAGCAACCCAAGCTGGCCGAACC

ATAAGAGCGTCTTTAACTCTGCAGGTCTGGAAGTTCGTGAATACGCTTATTATGATG

CGGAAAATCACACTCTTGACTTCGATGCACTGATTAACAGCCTGAATGAAGCTCAGG

CTGGCGACGTAGTGCTGTTCCATGGCTGCTGCCATACCCAACCGGTATCGACCCTA

CGCTGGAACAATGGCAAACACTGGCACAACTCTCCGTTGAGAAAGGCTGGTTACCG

CTGTTTGACTTCGCTTACCAGGGTTTTGCCCGTGGTCTGGAAGAAGATGCTGAAGGA

CTGCGCGCTTTCGCGGCTATGCATAAAGAGCTGATTGTTGCCAGTTCCTACTCTAAA

AACTTTGGCCTGTACAACGAGCGTGTTGGCGCTTGTACTCTGGTTGCTGCCGACAGT

GAAACCGTTGATCGCGCATTCAGCCAAATGAAAGCGGCGATTCGCGCTAACTACTCT

-continued

```
AACCCACCAGCACACGGCGCTTCTGTTGTTGCCACCATCCTGAGCAACGATGCGTTA

CGTGCGATTTGGGAACAAGAGCTGACTGATATGCGCCAGCGTATTCAGCGTATGCGT

CAGTTGTTCGTCAATACGCTGCAGGAAAAAGGCGCAAACCGCGACTTCAGCTTTATC

ATCAAACAGAACGGCATGTTCTCCTTCAGTGGCCTGACAAAAGAACAAGTGCTGCG

TCTGCGCGAAGAGTTTGGCGTATATGCGGTTGCTTCTGGTCGCGTAAATGTGGCCGG

GATGACACCAGATAACATGGCTCCGCTGTGCGAAGCGATTGTGGCAGTGCTGTAA
```

AspC polypeptide sequence

SEQ ID NO: 27

```
MFENITAAPADPILGLADLFRADERPGKINLGIGVYKDETGKTPVLTSVKKAEQYLLENE

TTKNYLGIDGIPEFGRCTQELLFGKGSALINDKRARTAQTPGGTGALRVAADFLAKNTS

VKRVWVSNPSWPNHKSVFNSAGLEVREYAYYDAENHTLDFDALINSLNEAQAGDVVL

FHGCCHNPTGIDPTLEQWQTLAQLSVEKGWLPLFDFAYQGFARGLEEDAEGLRAFAAM

HKELIVASSYSKNFGLYNERVGACTLVAADSETVDRAFSQMKAAIRANYSNPPAHGAS

VVATILSNDALRAIWEQELTDMRQRIQRMRQLFVNTLQEKGANRDFSFIIKQNGMFSFS

GLTKEQVLRLREEFGVYAVASGRVNVAGMTPDNIVIAPLCEAIVAVL
```

---

What is claimed is:

1. A genetically modified host cell comprising a heterologous nucleic acid encoding a biofilm dispersal polypeptide that decreases intracellular c-di-GMP levels, wherein the host cell overexpresses the biofilm dispersal polypeptide relative to a counterpart host cell that has not been modified to express the heterologous nucleic acid; and has at least one additional genetic modification to increase production of an amino acid or an amino acid derivative compared to a wildtype host cell,
wherein the host cell is of the genus *Escherichia*, *Hafnia* or *Corynebacterium*, the amino acid is lysine and the amino acid derivative is cadaverine.

2. The genetically modified host cell of claim 1, wherein the biofilm dispersal polypeptide is a BdcA or YahA polypeptide.

3. The genetically modified host cell of claim 2, wherein the biofilm dispersal polypeptide has at least 70% identity, or at least 75%, 80%, 85%, 90%, or 95% identity to a biofilm dispersal polypeptide having a sequence set forth in SEQ ID NO: 4 or SEQ ID NO:6.

4. The genetically modified host cell of claim 1, wherein the biofilm dispersal polypeptide is exogenous to the host cell.

5. The genetically modified host cell of claim 1, wherein the heterologous nucleic acid encoding the biofilm dispersal polypeptide is encoded by an expression vector introduced into the cell, wherein the expression vector comprises the heterologous nucleic acid operably linked to a promoter.

6. The genetically modified host cell of claim 1, wherein the heterologous nucleic acid is integrated into the host chromosome.

7. The genetically modified host cell of claim 1, wherein the host cell overexpresses a lysine decarboxylase.

8. The genetically modified host cell of claim 1, wherein the host cell overexpresses one or more lysine biosynthesis polypeptides.

9. The genetically modified host cell of claim 1, wherein the host cell overexpresses a TetA polypeptide.

10. The genetically modified host cell of claim 1, wherein the host cell is *Escherichia coli*, *Hafnia alvei*, or *Corynebacterium glutamicum*.

11. The genetically modified host cell of claim 10, wherein the host cell is *Escherichia coli*.

12. The genetically modified host cell of claim 11, wherein the biofilm dispersal polypeptide is a BdcA or YahA polypeptide.

13. The genetically modified host cell of claim 12, wherein the host cell overexpresses a LysC, DapA, LysA, Asd, DapB, AspC, and TetA polypeptide.

14. The genetically modified host cell of claim 13, wherein the host cell overexpresses a lysine decarboxylase polypeptide.

15. The genetically modified host cell of claim 12, wherein the biofilm dispersal polypeptide is exogenous to the host cell.

16. The genetically modified host cell of claim 12, wherein the heterologous nucleic acid encoding the biofilm dispersal polypeptide is encoded by an expression vector introduced into the cell, wherein the expression vector comprises the heterologous nucleic acid operably linked to a promoter.

17. The genetically modified host cell of claim 12, wherein the heterologous nucleic acid is integrated into the host chromosome.

18. A method of producing an amino acid or an amino acid derivative, the method comprising culturing a host cell of claim 1 under conditions in which the biofilm dispersal polypeptide is overexpressed.

19. A method of engineering a host cell to increase production of an amino acid or an amino acid derivative, the method comprising introduce a heterologous nucleic acid encoding an biofilm dispersal polypeptide that decreases intracellular c-di-GMP levels into the host cell, wherein the host cell has at least one additional genetic modification to increase production of an amino acid or an amino acid derivative compared to a wildtype host cell; and
culturing the host cell under conditions in which the heterologous biofilm dispersal polypeptide is expressed, wherein expression of the biofilm dispersal polypeptide increases the production of an amino acid or an amino acid derivative relative to a counterpart control host cell that has not been modified to express the heterologous nucleic acid,
wherein the host cell is of the genus *Escherichia*, *Hafnia* or *Corynebacterium*, the amino acid is lysine and the amino acid derivative is cadaverine.

20. The method of claim 19, wherein the biofilm dispersal polypeptide is exogenous to the host cell.

21. The method of claim 19, wherein the heterologous nucleic acid encoding the biofilm dispersal polypeptide is encoded by an expression vector introduced into the cell, wherein the expression vector comprises the heterologous nucleic acid operably linked to a promoter.

22. The method of claim 19, wherein the heterologous nucleic acid is integrated into the host chromosome.

23. The method of claim 19, wherein the biofilm dispersal polypeptide is a BdcA or YahA polypeptide.

24. The method of claim 23, wherein the biofilm dispersal polypeptide has at least 70% identity, or at least 75%, 80%, 85%, 90%, or 95% identity to the region of SEQ ID NO: 4 or 6 that encodes the biofilm dispersal polypeptide.

25. The method of claim 19, wherein the host cell overexpresses one or more lysine biosynthesis polypeptides.

26. The method of claim 19, wherein the host cell overexpresses a TetA polypeptide.

27. The method of claim 19, wherein the host cell overexpresses a lysine decarboxylase.

28. The method of claim 19, wherein the host cell is *Escherichia coli, Hafnia alvei,* or *Corynebacterium glutamicum*.

29. The method of claim 28, wherein the host cell is *Escherichia coli*.

30. The method of claim 29, wherein the biofilm dispersal polypeptide is BdcA or YahA polypeptide.

31. The method of claim 30, wherein the host cell overexpresses a LysC, DapA, LysA, Asd, DapB, AspC, and TetA polypeptide.

32. The method of claim 31, wherein the host cell overexpresses a lysine decarboxylase polypeptide.

33. The genetically modified host cell of claim 2, wherein the biofilm dispersal polypeptide BdcA is an *Escherichia coli* BdcA polypeptide having the amino acid sequence set forth in SEQ ID NO:4 or the biofilm dispersal polypeptide YahA is an *Escherichia coli* YahA polypeptide having the amino acid sequence set forth in SEQ ID NO:6.

34. The genetically modified host cell of claim 12, wherein the biofilm dispersal polypeptide BdcA is an *Escherichia coli* BdcA polypeptide having the amino acid sequence set forth in SEQ ID NO:4 or the biofilm dispersal polypeptide YahA is an *Escherichia coli* YahA polypeptide having the amino acid sequence set forth in SEQ ID NO:6.

35. The genetically modified host cell of claim 23, wherein the biofilm dispersal polypeptide BdcA is an *Escherichia coli* BdcA polypeptide having the amino acid sequence set forth in SEQ ID NO:4 or the biofilm dispersal polypeptide YahA is an *Escherichia coli* YahA polypeptide having the amino acid sequence set forth in SEQ ID NO:6.

36. The genetically modified host cell of claim 30, wherein the biofilm dispersal polypeptide BdcA is an *Escherichia coli* BdcA polypeptide having the amino acid sequence set forth in SEQ ID NO:4 or the biofilm dispersal polypeptide YahA is an *Escherichia coli* YahA polypeptide having the amino acid sequence set forth in SEQ ID NO:6.

\* \* \* \* \*

SEQUENCE LISTING

<160> NUMBER OF SEQ ID NOS: 82

<210> SEQ ID NO 1
<211> LENGTH: 2148
<212> TYPE: DNA
<213> ORGANISM: Escherichia coli

<400> SEQUENCE: 1

| | | | | | |
|---|---|---|---|---|---|
| atgaacgtta | ttgcaatatt | gaatcacatg | ggggtttatt | ttaaagaaga | acccatccgt | 60 |
| gaacttcatc | gcgcgcttga | acgtctgaac | ttccagattg | tttacccgaa | cgaccgtgac | 120 |
| gacttattaa | aactgatcga | aaacaatgcg | cgtctgtgcg | gcgttatttt | tgactgggat | 180 |
| aaatataatc | tcgagctgtg | cgaagaaatt | agcaaaatga | cgagaaccct | gccgttgtac | 240 |
| gcgttcgcta | atacgtattc | cactctcgat | gtaagcctga | atgacctgcg | tttacagatt | 300 |
| agcttctttg | aatatgcgct | gggtgctgct | gaagatattg | ctaataagat | caagcagacc | 360 |
| actgacgaat | atatcaacac | tattctgcct | ccgctgacta | agcactgtt | taaatatgtt | 420 |
| cgtgaaggta | aatatacttt | ctgtactcct | ggtcacatgg | gcggtactgc | attccagaaa | 480 |
| agcccggtag | gtagcctgtt | ctatgatttc | tttggtccga | ataccatgaa | atctgatatt | 540 |
| tccatttcag | tatctgaact | gggttctctg | ctggatcaca | gtggtccaca | caaagaagca | 600 |
| gaacagtata | tcgctcgcgt | ctttaacgca | gaccgcagct | acatggtgac | caacggtact | 660 |
| tccactgcga | acaaaattgt | tggtatgtac | tctgctccag | caggcagcac | cattctgatt | 720 |
| gaccgtaact | gccacaaatc | gctgacccac | ctgatgatga | tgagcgatgt | tacgccaatc | 780 |
| tatttccgcc | cgacccgtaa | cgcttacggt | attcttggtg | gtatcccaca | gagtgaattc | 840 |
| cagcacgcta | ccattgctaa | gcgcgtgaaa | gaaacaccaa | acgcaacctg | gccggtacat | 900 |
| gctgtaatta | ccaactctac | ctatgatggt | ctgctgtaca | acaccgactt | catcaagaaa | 960 |
| acactggatg | tgaaatccat | ccactttgac | tccgcgtggg | tgccttacac | caacttctca | 1020 |
| ccgatttacg | aaggtaaatg | cggtatgagc | ggtggccgtg | tagaagggaa | agtgatttac | 1080 |
| gaaacccagt | ccactcacaa | actgctggcg | gcgttctctc | aggcttccat | gatccacgtt | 1140 |

```
aaaggtgacg taaacgaaga aacctttaac gaagcctaca tgatgcacac caccacttct   1200
ccgcactacg gtatcgtggc gtccactgaa accgctgcgg cgatgatgaa aggcaatgca   1260
ggtaagcgtc tgatcaacgg ttctattgaa cgtgcgatca aattccgtaa agagatcaaa   1320
cgtctgagaa cggaatctga tggctggttc tttgatgtat ggcagccgga tcatatcgat   1380
acgactgaat gctggccgct gcgttctgac agcacctggc acggcttcaa aaacatcgat   1440
aacgagcaca tgtatcttga cccgatcaaa gtcaccctgc tgactccggg gatggaaaaa   1500
gacggcacca tgagcgactt tggtattccg gccagcatcg tggcgaaata cctcgacgaa   1560
catggcatcg ttgttgagaa aaccggtccg tataacctgc tgttcctgtt cagcatcggt   1620
atcgataaga ccaaagcact gagcctgctg cgtgctctga ctgactttaa acgtgcgttc   1680
gacctgaacc tgcgtgtgaa aaacatgctg ccgtctctgt atcgtgaaga tcctgaattc   1740
tatgaaaaca tgcgtattca ggaactggct cagaatatcc acaaactgat tgttcaccac   1800
aatctgccgg atctgatgta tcgcgcattt gaagtgctgc cgacgatggt aatgactccg   1860
tatgctgcat tccagaaaga gctgcacggt atgaccgaag aagtttacct cgacgaaatg   1920
gtaggtcgta ttaacgccaa tatgatcctt ccgtacccgc cgggagttcc tctggtaatg   1980
ccgggtgaaa tgatcaccga agaaagccgt ccggttctgg agttcctgca gatgctgtgt   2040
gaaatcggcg ctcactatcc gggctttgaa accgatattc acggtgcata ccgtcaggct   2100
gatgccgct ataccgttaa ggtattgaaa gaagaaagca aaaataa              2148
```

<210> SEQ ID NO 2
<211> LENGTH: 715
<212> TYPE: PRT
<213> ORGANISM: Escherichia coli

<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
```

```
                195                 200                 205
Asn Ala Asp Arg Ser Tyr Met Val Thr Asn Gly Thr Ser Thr Ala Asn
210                 215                 220
Lys Ile Val Gly Met Tyr Ser Ala Pro Ala Gly Ser Thr Ile Leu Ile
225                 230                 235                 240
Asp Arg Asn Cys His Lys Ser Leu Thr His Leu Met Met Met Ser Asp
                245                 250                 255
Val Thr Pro Ile Tyr Phe Arg Pro Thr Arg Asn Ala Tyr Gly Ile Leu
                260                 265                 270
Gly Gly Ile Pro Gln Ser Glu Phe Gln His Ala Thr Ile Ala Lys Arg
                275                 280                 285
Val Lys Glu Thr Pro Asn Ala Thr Trp Pro Val His Ala Val Ile Thr
                290                 295                 300
Asn Ser Thr Tyr Asp Gly Leu Leu Tyr Asn Thr Asp Phe Ile Lys Lys
305                 310                 315                 320
Thr Leu Asp Val Lys Ser Ile His Phe Asp Ser Ala Trp Val Pro Tyr
                325                 330                 335
Thr Asn Phe Ser Pro Ile Tyr Glu Gly Lys Cys Gly Met Ser Gly Gly
                340                 345                 350
Arg Val Glu Gly Lys Val Ile Tyr Glu Thr Gln Ser Thr His Lys Leu
                355                 360                 365
Leu Ala Ala Phe Ser Gln Ala Ser Met Ile His Val Lys Gly Asp Val
370                 375                 380
Asn Glu Glu Thr Phe Asn Glu Ala Tyr Met Met His Thr Thr Thr Ser
385                 390                 395                 400
Pro His Tyr Gly Ile Val Ala Ser Thr Glu Thr Ala Ala Ala Met Met
                405                 410                 415
Lys Gly Asn Ala Gly Lys Arg Leu Ile Asn Gly Ser Ile Glu Arg Ala
                420                 425                 430
Ile Lys Phe Arg Lys Glu Ile Lys Arg Leu Arg Thr Glu Ser Asp Gly
                435                 440                 445
Trp Phe Phe Asp Val Trp Gln Pro Asp His Ile Asp Thr Thr Glu Cys
450                 455                 460
Trp Pro Leu Arg Ser Asp Ser Thr Trp His Gly Phe Lys Asn Ile Asp
465                 470                 475                 480
Asn Glu His Met Tyr Leu Asp Pro Ile Lys Val Thr Leu Leu Thr Pro
                485                 490                 495
Gly Met Glu Lys Asp Gly Thr Met Ser Asp Phe Gly Ile Pro Ala Ser
                500                 505                 510
Ile Val Ala Lys Tyr Leu Asp Glu His Gly Ile Val Val Glu Lys Thr
                515                 520                 525
Gly Pro Tyr Asn Leu Leu Phe Leu Phe Ser Ile Gly Ile Asp Lys Thr
                530                 535                 540
Lys Ala Leu Ser Leu Leu Arg Ala Leu Thr Asp Phe Lys Arg Ala Phe
545                 550                 555                 560
Asp Leu Asn Leu Arg Val Lys Asn Met Leu Pro Ser Leu Tyr Arg Glu
                565                 570                 575
Asp Pro Glu Phe Tyr Glu Asn Met Arg Ile Gln Glu Leu Ala Gln Asn
                580                 585                 590
Ile His Lys Leu Ile Val His His Asn Leu Pro Asp Leu Met Tyr Arg
                595                 600                 605
Ala Phe Glu Val Leu Pro Thr Met Val Met Thr Pro Tyr Ala Ala Phe
                610                 615                 620
```

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Pro Gly Val
            645                 650                 655

Pro Leu Val Met Pro Gly Glu Met Ile Thr Glu Ser Arg Pro Val
        660                 665                 670

Leu Glu Phe Leu Gln Met Leu Cys Glu Ile Gly Ala His Tyr Pro Gly
    675                 680                 685

Phe Glu Thr Asp Ile His Gly Ala Tyr Arg Gln Ala Asp Gly Arg Tyr
690                 695                 700

Thr Val Lys Val Leu Lys Glu Glu Ser Lys Lys
705                 710                 715

<210> SEQ ID NO 3
<211> LENGTH: 714
<212> TYPE: DNA
<213> ORGANISM: Escherichia coli

<400> SEQUENCE: 3
atgggcgctt ttacaggtaa gacagttctc atcctcggtg gcagtcgtgg tatcggtgcc      60
gctatcgtac gtcgtttcgt caccgatggg gccaatgtac gattcaccta tgcggggtcg     120
aaagatgccg ctaaacgcct ggcacaagag actggagcga cagcagtatt cacagatagt     180
gctgacagag acgctgtcat tgatgtcgtt cgtaagagcg gcgcattgga tatcctggtg     240
gtaaatgcag gtattggcgt ctttggcgag gccctggaat aaatgccga cgatattgat      300 cgccttttca aaatcaatat tcatgctcct tatcatgcct ctgttgaagc cgcccggcag     360
atgcccgaag gcgggcgcat cttaatcatc ggctccgtga atggcgatcg tatgcctgtt     420
gcaggcatgg ctgcttatgc cgccagcaaa tctgccctgc aaggcatggc gcgcgggctg     480
gcccgtgatt ttggaccgcg tgggatcacc attaacgtcg tccagccagg gccaattgat     540
accgacgcta atcccgccaa cgggccaatg cgcgatatgt tgcatagttt gatggctatc     600
aaaagacatg gcaaccgga agaggtcgct ggtatggtcg catggttagc agggccagaa     660
gccagttttg ttaccggcgc gatgcatacc attgatggcg cgtttggcgc ataa           714

<210> SEQ ID NO 4
<211> LENGTH: 237
<212> TYPE: PRT
<213> ORGANISM: Escherichia coli

<400> SEQUENCE: 4

Met Gly Ala Phe Thr Gly Lys Thr Val Leu Ile Leu Gly Gly Ser Arg
1               5                   10                  15

Gly Ile Gly Ala Ala Ile Val Arg Arg Phe Val Thr Asp Gly Ala Asn
            20                  25                  30

Val Arg Phe Thr Tyr Ala Gly Ser Lys Asp Ala Ala Lys Arg Leu Ala
        35                  40                  45

Gln Glu Thr Gly Ala Thr Ala Val Phe Thr Asp Ser Ala Asp Arg Asp
    50                  55                  60

Ala Val Ile Asp Val Val Arg Lys Ser Gly Ala Leu Asp Ile Leu Val
65                  70                  75                  80

Val Asn Ala Gly Ile Gly Val Phe Gly Glu Ala Leu Glu Leu Asn Ala
                85                  90                  95

Asp Asp Ile Asp Arg Leu Phe Lys Ile Asn Ile His Ala Pro Tyr His
            100                 105                 110

```
Ala Ser Val Glu Ala Ala Arg Gln Met Pro Glu Gly Gly Arg Ile Leu
        115                 120                 125

Ile Ile Gly Ser Val Asn Gly Asp Arg Met Pro Val Ala Gly Met Ala
130                 135                 140

Ala Tyr Ala Ala Ser Lys Ser Ala Leu Gln Gly Met Ala Arg Gly Leu
145                 150                 155                 160

Ala Arg Asp Phe Gly Pro Arg Gly Ile Thr Ile Asn Val Val Gln Pro
                165                 170                 175

Gly Pro Ile Asp Thr Asp Ala Asn Pro Ala Asn Gly Pro Met Arg Asp
            180                 185                 190

Met Leu His Ser Leu Met Ala Ile Lys Arg His Gly Gln Pro Glu Glu
        195                 200                 205

Val Ala Gly Met Val Ala Trp Leu Ala Gly Pro Glu Ala Ser Phe Val
210                 215                 220

Thr Gly Ala Met His Thr Ile Asp Gly Ala Phe Gly Ala
225                 230                 235

<210> SEQ ID NO 5
<211> LENGTH: 1089
<212> TYPE: DNA
<213> ORGANISM: Escherichia coli

<400> SEQUENCE: 5
atgaattcat gtgattttcg tgtttttctg caagagttcg gtacaacggt tcatttgtca        60
ttgcctggta gcgtatccga aaagaacga ctgctactca agctgctgat gcagggaatg       120
tctgtaacag aaatatcaca gtacagaaat cgcagtgcaa agacaatttc acatcaaaag       180
aaacagctct tgagaaaact ggggattcag agcgatatta ctttctggcg cgatattttc       240
tttcagtaca atccggagat catatccgcc acggggagta atagtcacag atatattaat       300
gataatcact atcaccatat cgtcacgcct gaagccatca gtctggcgtt ggaaaaccac       360
gaattcaaac cgtggatcca accggttttc tgcgcgcaga ctggcgtact gacgggctgt       420
gaggtgcttg tccgctggga acatccacaa acgggaatta tcccaccgga tcagtttatt       480
cctctggcgg agtcatccgg tcttattgtc ataatgaccc gccaactgat gaaacagact       540
gcggatattc tgatgccggt aaaacatttg ctgccggaca atttccatat tggcatcaac       600
gtctcggcgg ttgtttttt ggcagcggga tttgaaaaag agtgtctgaa cctggttaat       660
aaattaggta acgataaaat caagctggtt ctcgagctaa cggaacgtaa ccctattccg       720
gtaacgccag aagccagagc gatatttgac agccttcatc agcacaacat taccttggcg       780
ctggatgact ttggtacggg ttatgcgacc tatcgttact tgcaggcgtt cccggtcgat       840
tttattaaga tcgataagtc atttgtgcaa atggcgagtg tcgacgaaat ctccggtcat       900
attgtggaca atattgtcga actagcgcgt aagcctggtc tgagtatcgt ggcggaaggg       960
gtagaaaccc aggagcaggc ggatttaatg atcggtaaag cgttcacttt tttgcagggc      1020
tatttgtact ctccgccagt accgggtaat aaatttatct ctgaatgggt aatgaaagca      1080
ggtggttga                                                              1089

<210> SEQ ID NO 6
<211> LENGTH: 362
<212> TYPE: PRT
<213> ORGANISM: Escherichia coli

<400> SEQUENCE: 6
```

Met Asn Ser Cys Asp Phe Arg Val Phe Leu Gln Glu Phe Gly Thr Thr
1               5                   10                  15

Val His Leu Ser Leu Pro Gly Ser Val Ser Glu Lys Glu Arg Leu Leu
            20                  25                  30

Leu Lys Leu Leu Met Gln Gly Met Ser Val Thr Glu Ile Ser Gln Tyr
        35                  40                  45

Arg Asn Arg Ser Ala Lys Thr Ile Ser His Gln Lys Lys Gln Leu Phe
    50                  55                  60

Glu Lys Leu Gly Ile Gln Ser Asp Ile Thr Phe Trp Arg Asp Ile Phe
65                  70                  75                  80

Phe Gln Tyr Asn Pro Glu Ile Ile Ser Ala Thr Gly Ser Asn Ser His
                85                  90                  95

Arg Tyr Ile Asn Asp Asn His Tyr His Ile Val Thr Pro Glu Ala
            100                 105                 110

Ile Ser Leu Ala Leu Glu Asn His Glu Phe Lys Pro Trp Ile Gln Pro
            115                 120                 125

Val Phe Cys Ala Gln Thr Gly Val Leu Thr Gly Cys Glu Val Leu Val
        130                 135                 140

Arg Trp Glu His Pro Gln Thr Gly Ile Ile Pro Pro Asp Gln Phe Ile
145                 150                 155                 160

Pro Leu Ala Glu Ser Ser Gly Leu Ile Val Ile Met Thr Arg Gln Leu
                165                 170                 175

Met Lys Gln Thr Ala Asp Ile Leu Met Pro Val Lys His Leu Leu Pro
            180                 185                 190

Asp Asn Phe His Ile Gly Ile Asn Val Ser Ala Gly Cys Phe Leu Ala
        195                 200                 205

Ala Gly Phe Glu Lys Glu Cys Leu Asn Leu Val Asn Lys Leu Gly Asn
    210                 215                 220

Asp Lys Ile Lys Leu Val Leu Glu Leu Thr Glu Arg Asn Pro Ile Pro
225                 230                 235                 240

Val Thr Pro Glu Ala Arg Ala Ile Phe Asp Ser Leu His Gln His Asn
                245                 250                 255

Ile Thr Phe Ala Leu Asp Asp Phe Gly Thr Gly Tyr Ala Thr Tyr Arg
            260                 265                 270

Tyr Leu Gln Ala Phe Pro Val Asp Phe Ile Lys Ile Asp Lys Ser Phe
        275                 280                 285

Val Gln Met Ala Ser Val Asp Glu Ile Ser Gly His Ile Val Asp Asn
    290                 295                 300

Ile Val Glu Leu Ala Arg Lys Pro Gly Leu Ser Ile Val Ala Glu Gly
305                 310                 315                 320

Val Glu Thr Gln Glu Gln Ala Asp Leu Met Ile Gly Lys Gly Val His
                325                 330                 335

Phe Leu Gln Gly Tyr Leu Tyr Ser Pro Pro Val Pro Gly Asn Lys Phe
            340                 345                 350

Ile Ser Glu Trp Val Met Lys Ala Gly Gly
            355                 360

<210> SEQ ID NO 7
<211> LENGTH: 38
<212> TYPE: DNA
<213> ORGANISM: Artificial Sequence
<220> FEATURE:
<223> OTHER INFORMATION: synthetic promoter nucleic acid sequence

<400> SEQUENCE: 7

```
agtttattct tgacatgtag tgaggggct ggtataat                              38
```

<210> SEQ ID NO 8
<211> LENGTH: 1191
<212> TYPE: DNA
<213> ORGANISM: Escherichia coli

<400> SEQUENCE: 8

```
atgaaatcta acaatgcgct catcgtcatc ctcggcaccg tcaccctgga tgctgtaggc    60
ataggcttgg ttatgccggt actgccgggc ctcttgcggg atatcgtcca ttccgacagc   120
atcgccagtc actatggcgt gctgctagcg ctatatgcgt tgatgcaatt tctatgcgca   180
cccgttctcg gagcactgtc cgaccgcttt ggccgccgcc agtcctgct  cgcttcgcta   240
cttggagcca ctatcgacta cgcgatcatg gcgaccacac ccgtcctgtg atcctctac   300
gccggacgca tcgtggccgg catcaccggc gccacaggtg cggttgctgg cgcctatatc   360
gccgacatca ccgatgggga agatcgggct cgccacttcg ggctcatgag cgcttgtttc   420
ggcgtgggta tggtggcagg ccccgtggcc ggggactgt  tgggcgccat ctccttgcat   480
gcaccattcc ttgcggcggc ggtgctcaac ggcctcaacc tactactggg ctgcttccta   540
atgcaggagt cgcataaggg agagcgtcga ccgatgccct tgagagcctt caacccagtc   600
agctccttcc ggtgggcgcg gggcatgact atcgtcgccg cacttatgac tgtcttcttt   660
atcatgcaac tcgtaggaca ggtgccggca gcgctctggg tcattttcgg cgaggaccgc   720
tttcgctgga gcgcgacgat gatcggcctg tcgcttgcgg tattcggaat cttgcacgcc   780
ctcgctcaag ccttcgtcac tggtcccgcc accaaacgtt tcggcgagaa gcaggccatt   840
atcgccggca tggcggccga cgcgctgggc tacgtcttgc tggcgttcgc gacgcgaggc   900
tggatggcct tccccattat gattcttctc gcttccggcg catcgggat  gcccgcgttg   960
caggccatgc tgtccaggca ggtagatgac gaccatcagg acagcttca  aggatcgctc  1020
gcggctctta ccagcctaac ttcgatcatt ggaccgctga tcgtcacggc gatttatgcc  1080
gcctcggcga gcacatggaa cgggttggca tggattgtag gcgccgccct ataccttgtc  1140
tgcctccccg cgttgcgtcg cggtgcatgg agccgggcca cctcgacctg a           1191
```

<210> SEQ ID NO 9
<211> LENGTH: 396
<212> TYPE: PRT
<213> ORGANISM: Escherichia coli

<400> SEQUENCE: 9

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110
```

Gly Ala Val Ala Gly Ala Tyr Ile Ala Asp Ile Thr Asp Gly Glu Asp
              115                 120                 125

Arg Ala Arg His Phe Gly Leu Met Ser Ala Cys Phe Gly Val Gly Met
        130                 135                 140

Val Ala Gly Pro Val Ala Gly Leu Leu Gly Ala Ile Ser Leu His
145                 150                 155                 160

Ala Pro Phe Leu Ala Ala Val Leu Asn Gly Leu Asn Leu Leu Leu
                165                 170                 175

Gly Cys Phe Leu Met Gln Glu Ser His Lys Gly Glu Arg Arg Pro Met
                180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
                260                 265                 270

Arg Phe Gly Glu Lys Gln Ala Ile Ala Gly Met Ala Ala Asp Ala
        275                 280                 285

Leu Gly Tyr Val Leu Leu Ala Phe Ala Thr Arg Gly Trp Met Ala Phe
        290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp Asp His Gln Gly Gln Leu
                325                 330                 335

Gln Gly Ser Leu Ala Ala Leu Thr Ser Leu Thr Ser Ile Ile Gly Pro
                340                 345                 350

Leu Ile Val Thr Ala Ile Tyr Ala Ala Ser Ala Ser Thr Trp Asn Gly
                355                 360                 365

Leu Ala Trp Ile Val Gly Ala Ala Leu Tyr Leu Val Cys Leu Pro Ala
        370                 375                 380

Leu Arg Arg Gly Ala Trp Ser Arg Ala Thr Ser Thr
385                 390                 395

<210> SEQ ID NO 10
<211> LENGTH: 1350
<212> TYPE: DNA
<213> ORGANISM: Escherichia coli

<400> SEQUENCE: 10
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag actggaacc tggcgagcga      180 ttcgaaaaac tcgacgctat ccgcaacatc cagtttgcca ttctggaacg tctgcgttac     240
ccgaacgtta tccgtgaaga gattgaacgt ctgctggaga acattactgt tctggcagaa     300
gcggcggcgc tggcaacgtc tccggcgctg acagatgagc tggtcagcca cggcgagctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540

```
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cgggcatcta caccaccgat ccacgcgtag tttccgcagc aaaacgcatt    720
gatgaaatcg cgtttgccga agcggcagag atggcaactt ttggtgcaaa agtactgcat    780
ccggcaacgt tgctacccgc agtacgcagc gatatcccgg tctttgtcgg ctccagcaaa    840
gacccacgcg caggtggtac gctggtgtgc aataaaactg aaaatccgcc gctgttccgc    900
gctctggcgc ttcgtcgcaa tcagactctg ctcactttgc acagcctgaa tatgctgcat    960
tctcgcggtt tcctcgcgga agttttcggc atcctcgcgc ggcataatat ttcggtagac   1020
ttaatcacca cgtcagaagt gagcgtggca ttaaccctig ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgtc aaaagcctgc   1200
ggcgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                    1350
```

<210> SEQ ID NO 11
<211> LENGTH: 449
<212> TYPE: PRT
<213> ORGANISM: Escherichia coli

<400> SEQUENCE: 11

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220
```

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 12
<211> LENGTH: 879
<212> TYPE: DNA
<213> ORGANISM: Escherichia coli

<400> SEQUENCE: 12
atgttcacgg gaagtattgt cgcgattgtt actccgatgg atgaaaaagg taatgtctgt       60
cgggctagct tgaaaaaact gattgattat catgtcgcca gcggtacttc ggcgatcgtt      120
tctgttggca ccactggcga gtccgctacc ttaaatcatg acgaacatgc tgatgtggtg      180
atgatgacgc tggatctggc tgatgggcgc attccggtaa ttgccgggac cggcgctaac      240
gctactgcgg aagccattag cctgacgcag cgcttcaatg acagtggtat cgtcggctgc      300
ctgacggtaa ccccttacta caatcgtccg tcgcaagaag gtttgtatca gcatttcaaa      360
gccatcgctg agcatactga cctgccgcaa attctgtata atgtgccgtc ccgtactggc      420
tgcgatctgc tcccggaaac ggtgggccgt ctggcgaaag taaaaaatat tatcggaatc      480
aaagaggcaa cagggaactt aacgcgtgta accagatcaa agagctggt tcagatgat      540 tttgttctgc tgagcggcga tgatgcgagc gcgctggact tcatgcaatt gggcggtcat      600
ggggttattt ccgttacggc taacgtcgca gcgcgtgata tggcccagat gtgcaaactg      660
gcagcagaag gcatttttgc cgaggcacgc gttattaatc agcgtctgat gccattacac      720
aacaaactat ttgtcgaacc caatccaatc ccggtgaaat gggcatgtaa ggaactgggt      780
cttgtggcga ccgatacgct cgcgcctgcca atgacaccaa tcaccgacag tggtcgtgag      840
acggtcagag cggcgcttaa gcatgccggt ttgctgtaa            879

<210> SEQ ID NO 13
<211> LENGTH: 292
<212> TYPE: PRT
<213> ORGANISM: Escherichia coli

<400> SEQUENCE: 13

```
Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290
```

<210> SEQ ID NO 14
<211> LENGTH: 1263
<212> TYPE: DNA
<213> ORGANISM: Escherichia coli

<400> SEQUENCE: 14
atgccacatt cactgttcag caccgatacc gatctcaccg ccgaaaatct gctgcgtttg            60
cccgctgaat ttggctgccc ggtgtgggtc tacgatgcgc aaattattcg tcggcagatt           120

-continued

```
gcagcgctga acagtttga tgtggtgcgc tttgcacaga aagcctgttc caatattcat      180
attttgcgct taatgcgtga gcagggcgtg aaagtggatt ccgtctcgtt aggcgaaata      240
gagcgtgcgt tggcggcggg ttacaatccg caaacgcacc ccgatgatat tgttttttacg    300
gcagatgtta tcgatcaggc gacgcttgaa cgcgtcagtg aattgcaaat tccggtgaat     360
gcgggttctg ttgatatgct cgaccaactg ggccaggttt cgccagggca tcgggtatgg    420
ctgcgcgtta atccggggtt tggtcacgga catagccaaa aaaccaatac cggtggcgaa    480
aacagcaagc acggtatctg gtacaccgat ctgcccgccg cactggacgt gatacaacgt     540
catcatctgc agctggtcgg cattcacatg cacattggtt ctggcgttga ttatgcccat    600
ctggaacagg tgtgtggtgc tatggtgcgt caggtcatcg aattcggtca ggatttacag    660
gctatttctg cgggcggtgg gctttctgtt ccttatcaac agggtgaaga ggcggttgat    720
accgaacatt attatggtct gtggaatgcc gcgcgtgagc aaatcgcccg ccatttgggc    780
caccctgtga aactggaaat tgaaccgggt cgcttcctgg tagcgcagtc tggcgtatta   840
attactcagg tgcggagcgt caaacaaatg gggagccgcc actttgtgct ggttgatgcc   900
gggttcaacg atctgatgcg cccggcaatg tacggtagtt accaccatat cagtgccctg   960
gcagctgatg gtcgttctct ggaacacgcg ccaacggtgg aaaccgtcgt cgccggaccg  1020
ttatgtgaat cgggcgatgt ctttacccag caggaagggg gaaatgttga acccgcgcc   1080
ttgccggaag tgaaggcagg tgattatctg gtactgcatg atacaggggc atatggcgca  1140
tcaatgtcat ccaactacaa tagccgtccg ctgttaccag aagttctgtt tgataatggt  1200
caggcgcggt tgattcgccg tcgccagacc atcgaagaat tactggcgct ggaattgctt  1260
taa                                                                  1263
```

<210> SEQ ID NO 15
<211> LENGTH: 420
<212> TYPE: PRT
<213> ORGANISM: Escherichia coli

<400> SEQUENCE: 15

```
Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
                20                  25                  30

Ala Gln Ile Ile Arg Arg Gln Ile Ala Ala Leu Lys Gln Phe Asp Val
            35                  40                  45

Val Arg Phe Ala Gln Lys Ala Cys Ser Asn Ile His Ile Leu Arg Leu
        50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160
```

Asn Ser Lys His Gly Ile Trp Tyr Thr Asp Leu Pro Ala Ala Leu Asp
            165                 170                 175

Val Ile Gln Arg His His Leu Gln Leu Val Gly Ile His Met His Ile
        180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
        210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
        290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
        370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 16
<211> LENGTH: 1350
<212> TYPE: DNA
<213> ORGANISM: Artificial Sequence
<220> FEATURE:
<223> OTHER INFORMATION: lysC-1 nucleic acid sequence

<400> SEQUENCE: 16
atgtctgaaa ttgttgtctc caaatttggc ggtaccagcg tagctgattt tgacgccatg      60
aaccgcagcg ctgatattgt gctttctgat gccaacgtgc gtttagttgt cctctcggct     120
tctgctggta tcactaatct gctggtcgct ttagctgaag gactggaacc tggcgagcga     180
ttcgaaaaac tcgacgctat ccgcaacatc cagtttgcca ttctgaacg tctgcgttac      240 ccgaacgtta tccgtgaaga gattgaacgt ctgctggaga acattactgt tctggcagaa     300
gcggcggcgc tggcaacgtc tccggcgctg acagatgagc tggtcagcca cggcgagctg     360
atgtcgaccc tgctgtttgt tgagatcctg cgcgaacgcg atgttcaggc acagtggttt     420
gatgtacgta aagtgatgcg taccaacgac cgatttggtc gtgcagagcc agatatagcc     480
gcgctggcgg aactggccgc gctgcagctg ctcccacgtc tcaatgaagg cttagtgatc     540

```
acccagggat ttatcggtag cgaaaataaa ggtcgtacaa cgacgcttgg ccgtggaggc    600
agcgattata cggcagcctt gctggcggag gctttacacg catctcgtgt tgatatctgg    660
accgacgtcc cgggcatcta caccaccgat ccacgcgtag tttccgcagc aaaacgcatt    720
gatgaaatcg cgtttgccga agcggcgagg atggcaactt ttggtgcaaa agtactgcat    780
ccggcaacgt tgctacccgc agtacgcagc gatatcccgg tctttgtcgg ctccagcaaa    840
gacccacgcg caggtggtac gctgatgtgc aataaaactg aaaatccgcc gctgttccgc    900
gctctggcgc ttcgtcgcaa tcagactctg ctcactttgc acagcctgaa atatactgca t  960 tctcgcgatt cctcgcgga agttttcggc atcctcgcgc ggcataatat ttcggtagac    1020
ttaatcacca cgtcagaagt gagcgtggca ttaacccttg ataccaccgg ttcaacctcc    1080
actggcgata cgttgctgac gcaatctctg ctgatggagc tttccgcact gtgtcgggtg    1140
gaggtggaag aaggtctggc gctggtcgcg ttgattggca atgacctgcc aaaagcctgc    1200
ggcgttggca agaggtatt cggcgtactg gaaccgttca acattcgcat gatttgttat     1260
ggcgcatcca gccataacct gtgcttcctg gtgcccggcg aagatgccga gcaggtggtg    1320
caaaaactgc atagtaattt gtttgagtaa                                    1350
```

<210> SEQ ID NO 17
<211> LENGTH: 449
<212> TYPE: PRT
<213> ORGANISM: Artificial Sequence
<220> FEATURE:
<223> OTHER INFORMATION: LysC-1 polypeptide sequence

<400> SEQUENCE: 17

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220
```

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
            245                 250                 255

Lys Val Leu His Pro Ala Thr Leu Leu Pro Ala Val Arg Ser Asp Ile
        260                 265                 270

Pro Val Phe Val Gly Ser Ser Lys Asp Pro Arg Ala Gly Gly Thr Leu
    275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Ile Leu His
305                 310                 315                 320

Ser Arg Asp Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 18
<211> LENGTH: 1272
<212> TYPE: DNA
<213> ORGANISM: Artificial Sequence
<220> FEATURE:
<223> OTHER INFORMATION: S-lysC nucleic acid sequence

<400> SEQUENCE: 18
atgggcttag ttgtgcagaa atacggcggt agtagcgtgg ccgatgccga aggcatcaaa      60
cgtgttgcca acgcattgt tgaagccaaa aagaatggta atcaggttgt ggttgtcgtt     120
tcagcaatgg gcgataccac agatgaactt attgatctgg cccaggaagt tagcccgatt     180
ccgagcggtc gtgaatttga tatgttactt acagccggtg aacgtattag catggcctta     240
ctggccatgg caatcaaaaa tctgggtcac gaagcccaga gcttcacagg ttcacaggcc     300
ggtgttatta cagatagcgt tcataataaa gcgcgcatta tcgatgttac cccgggtcgt     360
attaaagcaa gcctggatga aggcaacatc gccattgtgg caggctttca gggtgttagc     420
caggataaaa aggatattac cacactgggt cgcggtggca gcgatacaac ggcagtggcc     480
ctggcagccg cattaaatgc agatgttgt gaaatctata ccgatgttga tggtgttttt     540
accgcagatc cgcgcgtggt taagaaagcc cgtaaaattg aatggatctc attcgaagat     600
atgctggaat tagccagcag cggtagcaaa gttctgctgc atcgttgtgt tgaatatgca     660
cgccgttaca atattcctat tcatgttcgt tcaagttttt caggtttaca gggcacatgg     720

```
gttagcaatg aaccgcaggg tgatcgtccg atggaacagg caatcattag cggtgttgca    780
catgataccT cagaagcaaa agttaccgtt gttggtgttc cggataaacc gggcgaagca    840
gcacgtatct ttcgggccat tgccgattca gaagtgaata tcgacatggt ggttcagaat    900
gttagcgcag caagcaccgg tctgaccgat attagcttta ccctgccgaa agcagaaggt    960
cgtaaagcag ttgcagcact ggagaaaacc cgtgcagccg tgggctttga tagtttacgg   1020
tatgatgatc agattgcaaa aattagcctg gttggtgcag gtatgaaaac caatccgggt   1080
gtgaccgcaa ccttttttga agcattaagc aatgcaggcg ttaatattga actgattagc   1140
accagtgaaa ttcgtatcag cgttgtgacc cgcgcagatg atgttaatga agccgttcag   1200
gcagttcata gcgcatttgg tctggatagc gaaaccgatg aagcagtggt ttatggcggc   1260
acaggtcgtt aa                                                       1272
```

```
<210> SEQ ID NO 19
<211> LENGTH: 425
<212> TYPE: PRT
<213> ORGANISM: Artificial Sequence
<220> FEATURE:
<223> OTHER INFORMATION: S-LysC polypeptide sequence

<400> SEQUENCE: 19
```

Met Gly Leu Val Val Gln Lys Tyr Gly Gly Ser Ser Val Ala Asp Ala
1               5                   10                  15

Glu Gly Ile Lys Arg Val Ala Lys Arg Ile Val Glu Ala Lys Lys Asn
            20                  25                  30

Gly Asn Gln Val Val Ala Val Val Ser Ala Met Gly Asp Thr Thr Asp
        35                  40                  45

Glu Leu Ile Asp Leu Ala Glu Gln Val Ser Pro Ile Pro Ala Gly Arg
    50                  55                  60

Glu Leu Asp Met Leu Leu Thr Ala Gly Glu Arg Ile Ser Met Ala Leu
65                  70                  75                  80

Leu Ala Met Ala Ile Lys Asn Leu Gly His Glu Ala Gln Ser Phe Thr
                85                  90                  95

Gly Ser Gln Ala Gly Val Ile Thr Asp Ser Val His Asn Lys Ala Arg
            100                 105                 110

Ile Ile Asp Val Thr Pro Gly Arg Ile Arg Thr Ser Val Asp Glu Gly
        115                 120                 125

Asn Val Ala Ile Val Ala Gly Phe Gln Gly Val Ser Gln Asp Ser Lys
    130                 135                 140

Asp Ile Thr Thr Leu Gly Arg Gly Gly Ser Asp Thr Thr Ala Val Ala
145                 150                 155                 160

Leu Ala Ala Ala Leu Asp Ala Asp Val Cys Glu Ile Tyr Thr Asp Val
                165                 170                 175

Asp Gly Val Phe Thr Ala Asp Pro Arg Val Val Pro Lys Ala Lys Lys
            180                 185                 190

Ile Asp Trp Ile Ser Phe Glu Asp Met Leu Glu Leu Ala Ala Ser Gly
        195                 200                 205

Ser Lys Val Leu Leu His Arg Cys Val Glu Tyr Ala Arg Arg Tyr Asn
    210                 215                 220

Ile Pro Ile His Val Arg Ser Ser Phe Ser Gly Leu Gln Gly Thr Trp
225                 230                 235                 240

Val Ser Ser Glu Pro Ile Lys Gln Gly Glu Lys His Val Glu Gln Ala
                245                 250                 255

Leu Ile Ser Gly Val Ala His Asp Thr Ser Glu Ala Lys Val Thr Val

```
                260             265             270
Val Gly Val Pro Asp Lys Pro Gly Glu Ala Ala Ile Phe Arg Ala
            275             280             285

Ile Ala Asp Ala Gln Val Asn Ile Asp Met Val Val Gln Asn Val Ser
            290             295             300

Ala Ala Ser Thr Gly Leu Thr Asp Ile Ser Phe Thr Leu Pro Lys Ser
305             310             315             320

Glu Gly Arg Lys Ala Ile Asp Ala Leu Glu Lys Asn Arg Pro Gly Ile
            325             330             335

Gly Phe Asp Ser Leu Arg Tyr Asp Asp Gln Ile Gly Lys Ile Ser Leu
            340             345             350

Val Gly Ala Gly Met Lys Ser Asn Pro Gly Val Thr Ala Asp Phe Phe
            355             360             365

Thr Ala Leu Ser Asp Ala Gly Val Asn Ile Glu Leu Ile Ser Thr Ser
    370             375             380

Glu Ile Arg Ile Ser Val Val Thr Arg Lys Asp Asp Val Asn Glu Ala
385             390             395             400

Val Arg Ala Val His Thr Ala Phe Gly Leu Asp Ser Asp Ser Asp Glu
            405             410             415

Ala Val Val Tyr Gly Gly Thr Gly Arg
            420             425

<210> SEQ ID NO 20
<211> LENGTH: 1104
<212> TYPE: DNA
<213> ORGANISM: Escherichia coli

<400> SEQUENCE: 20
atgaaaaatg ttggttttat cggctggcgc ggtatggtcg ctccgttct catgcaacgc      60
atggttgaag agcgcgactt cgacgccatt cgccctgtct tcttttctac ttctcagctt    120
ggccaggctg cgccgtcttt tggcggaacc actggcacac ttcaggatgc ctttgatctg    180
gaggcgctaa aggccctcga tatcattgtg acctgtcagg cggcgattaa taccaacgaa    240
atctatccaa agcttcgtga agcggatgg caaggttact ggattgacgc agcatcgtct    300
ctgcgcatga agatgacgc catcatcatt cttgaccccg tcaatcagga cgtcattacc    360
gacggattaa ataatggcat caggactttt gttggcggta actgtaccgt aagcctgatg    420
ttgatgtcgt tgggtggttt attcgccaat gatcttgttg attgggtgtc cgttgcaacc    480
taccaggccg cttccggcgg tggtgcgcga catatgcgtg agttattaac ccagatgggc    540
catctgtatg ccatgtggc agatgaactc gcgaccccgt cctctgctat tctcgatatc    600
gaacgcaaag tcacaacctt aacccgtagc ggtgagctgc cggtggataa ctttggcgtg    660
ccgctggcgg gtagcctgat ccgtggatc gacaaacagc tcgataacgg tcagagccgc    720
gaagagtgga agggcaggc ggaaaccaac aagatcctca acacatcttc cgtaattccg    780
gtagatggtt tatgtgtgcg tgtcggggca ttgcgctgcc acagccaggc attcactatt    840
aaattgaaaa aagatgtgtc tattccgacc gtggaagaac tgctggctgc gcacaatccg    900
tgggcgaaag tcgttccgaa cgatcgggaa atcactatgc gtgagctaac ccagctgcc    960
gttaccggca cgctgaccac gccggtaggc cgcctgcgta agctgaatat gggaccagag   1020
ttcctgtcag cctttaccgt gggcgaccag ctgctgtggg gggccgcgga gccgctgcgt   1080
cggatgcttc gtcaactggc gtaa                                          1104
```

-continued

```
<210> SEQ ID NO 21
<211> LENGTH: 350
<212> TYPE: PRT
<213> ORGANISM: Escherichia coli

<400> SEQUENCE: 21

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln
            340                 345                 350

<210> SEQ ID NO 22
<211> LENGTH: 822
<212> TYPE: DNA
<213> ORGANISM: Escherichia coli
```

<400> SEQUENCE: 22

```
atgcatgatg caaacatccg cgttgccatc gcgggagccg gggggcgtat gggccgccag    60
ttgattcagg cggcgctggc attagagggc gtgcagttgg gcgctgcgct ggagcgtgaa   120
ggatcttctt tactgggcag cgacgccggt gagctggccg gagccgggaa aacaggcgtt   180
accgtgcaaa gcagcctcga tgcggtaaaa gatgattttg atgtgtttat cgattttacc   240
cgtccggaag gtacgctgaa ccatctcgct ttttgtcgcc agcatggcaa agggatggtg   300
atcggcacta cggggtttga cgaagccggt aaacaagcaa ttcgtgacgc cgctgccgat   360
attgcgattg tctttgctgc caattttagc gttggcgtta acgtcatgct taagctgctg   420
gagaaagcag ccaaagtgat gggtgactac accgatatcg aaattattga agcacatcat   480
agacataaag ttgatgcgcc gtcaggcacc gcactggcaa tgggagaggc gatcgcccac   540
gcccttgata aagatctgaa agattgcgcg gtctacagtc gtgaaggcca caccggtgaa   600
cgtgtgcctg gcaccattgg ttttgccacc gtgcgtgcag gtgacatcgt tggtgaacat   660
accgcgatgt ttgccgatat tggcgagcgt ctggagatca cccataaggc gtccagccgt   720
atgacatttg ctaacggcgc ggtaagatcg gctttgtggt tgagtggtaa ggaaagcggt   780
cttttttgata tgcgagatgt acttgatctc aataatttgt aa                     822
```

<210> SEQ ID NO 23
<211> LENGTH: 273
<212> TYPE: PRT
<213> ORGANISM: Escherichia coli

<400> SEQUENCE: 23

```
Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
            20                  25                  30

Leu Gly Ala Ala Leu Glu Arg Glu Gly Ser Ser Leu Leu Gly Ser Asp
        35                  40                  45

Ala Gly Glu Leu Ala Gly Ala Gly Lys Thr Gly Val Thr Val Gln Ser
    50                  55                  60

Ser Leu Asp Ala Val Lys Asp Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Ala Asp Ile Ala Ile Val Phe Ala Ala Asn
        115                 120                 125

Phe Ser Val Gly Val Asn Val Met Leu Lys Leu Leu Glu Lys Ala Ala
    130                 135                 140

Lys Val Met Gly Asp Tyr Thr Asp Ile Glu Ile Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
    210                 215                 220
```

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu

<210> SEQ ID NO 24
<211> LENGTH: 825
<212> TYPE: DNA
<213> ORGANISM: Escherichia coli

<400> SEQUENCE: 24

```
atgcagcagt tacagaacat tattgaaacc gcttttgaac gccgtgccga gatcacgcca    60
gccaatgcag acaccgttac ccgcgaagcg gtaaatcagg tgatcgccct gctggattcc   120
ggcgcactgc gtgtagcgga aaaaattgac ggtcagtggg tgacgcatca gtggttgaaa   180
aaagcggtgc tgctctcttt ccgtattaat gataatcagg tgatcgaagg ggcagaaagc   240
cgctacttcg acaaagtgcc gatgaaattc gccgactacg acgaagcacg tttccagaaa   300
gaaggcttcc gcgttgtgcc accagcggcg gtacgtcagg gtgcgtttat tgcccgtaac   360
accgtgctga tgccgtctta cgtcaacatc ggcgcatatg ttgatgaagg caccatggtt   420
gatacctggg cgaccgtcgg ttcttgtgcg cagattggta aaacgtcca cctttccggt   480
ggcgtgggca tcggcggcgt gctggaaccg ctgcaggcta acccaaccat cattgaagat   540
aattgcttca tcggcgcgcg ctctgaagtg gttgaagggg tgattgtcga agaaggttcc   600
gtcatttcca tggcgtata cattggtcag agcacccgta tttacgaccg tgaaaccggc   660
gaaatccact acgtcgcgt tccggcgggg tctgtggttg tttcaggtaa tctgccgtca   720
aaagatggca aatacagcct ctactgtgcg gttatcgtta agaaagttga cgcgaaaact   780
cgcggcaaag tcggcattaa cgaactgctg cgtaccatcg actaa              825
```

<210> SEQ ID NO 25
<211> LENGTH: 274
<212> TYPE: PRT
<213> ORGANISM: Escherichia coli

<400> SEQUENCE: 25

Met Gln Gln Leu Gln Asn Ile Ile Glu Thr Ala Phe Glu Arg Arg Ala
1               5                   10                  15

Glu Ile Thr Pro Ala Asn Ala Asp Thr Val Thr Arg Glu Ala Val Asn
            20                  25                  30

Gln Val Ile Ala Leu Leu Asp Ser Gly Ala Leu Arg Val Ala Glu Lys
        35                  40                  45

Ile Asp Gly Gln Trp Val Thr His Gln Trp Leu Lys Lys Ala Val Leu
    50                  55                  60

Leu Ser Phe Arg Ile Asn Asp Asn Gln Val Ile Glu Gly Ala Glu Ser
65                  70                  75                  80

Arg Tyr Phe Asp Lys Val Pro Met Lys Phe Ala Asp Tyr Asp Glu Ala
                85                  90                  95

Arg Phe Gln Lys Glu Gly Phe Arg Val Val Pro Ala Ala Val Arg
            100                 105                 110

Gln Gly Ala Phe Ile Ala Arg Asn Thr Val Leu Met Pro Ser Tyr Val
        115                 120                 125

```
Asn Ile Gly Ala Tyr Val Asp Glu Gly Thr Met Val Asp Thr Trp Ala
130                 135                 140

Thr Val Gly Ser Cys Ala Gln Ile Gly Lys Asn Val His Leu Ser Gly
145                 150                 155                 160

Gly Val Gly Ile Gly Gly Val Leu Glu Pro Leu Gln Ala Asn Pro Thr
                165                 170                 175

Ile Ile Glu Asp Asn Cys Phe Ile Gly Ala Arg Ser Glu Val Val Glu
            180                 185                 190

Gly Val Ile Val Glu Glu Gly Ser Val Ile Ser Met Gly Val Tyr Ile
        195                 200                 205

Gly Gln Ser Thr Arg Ile Tyr Asp Arg Glu Thr Gly Glu Ile His Tyr
210                 215                 220

Gly Arg Val Pro Ala Gly Ser Val Val Val Ser Gly Asn Leu Pro Ser
225                 230                 235                 240

Lys Asp Gly Lys Tyr Ser Leu Tyr Cys Ala Val Ile Val Lys Lys Val
                245                 250                 255

Asp Ala Lys Thr Arg Gly Lys Val Gly Ile Asn Glu Leu Leu Arg Thr
            260                 265                 270

Ile Asp

<210> SEQ ID NO 26
<211> LENGTH: 1191
<212> TYPE: DNA
<213> ORGANISM: Escherichia coli

<400> SEQUENCE: 26
atgtttgaga acattaccgc cgctcctgcc gacccgattc tgggcctggc cgatctgttt      60
cgtgccgatg aacgtcccgg caaaattaac ctcgggattg tgtctataa agatgagacg      120
ggcaaaaccc cggtactgac cagcgtgaaa aaggctgaac agtatctgct cgaaaatgaa     180
accaccaaaa attacctcgg cattgacggc atccctgaat tggtcgctg cactcaggaa     240
ctgctgtttg gtaaaggtag cgccctgatc aatgacaaac gtgctcgcac ggcacagact     300
ccgggggca ctggcgcact acgcgtggct gccgatttcc tggcaaaaaa taccagcgtt      360
aagcgtgtgt gggtgagcaa cccaagctgg ccgaaccata gagcgtcttt taactctgca     420
ggtctggaag ttcgtgaata cgcttattat gatgcggaaa atcacactct tgacttcgat     480
gcactgatta cagcctgaa tgaagctcag gctggcgacg tagtgctgtt ccatggctgc     540
tgccataacc caaccggtat cgaccctacg ctggaacaat ggcaaacact ggcacaactc     600
tccgttgaga aaggctggtt accgctgttt gacttcgctt accagggttt tgcccgtggt     660
ctggaagaag atgctgaagg actgcgcgct ttcgcggcta tgcataaaga gctgattgtt     720
gccagttcct actctaaaaa ctttggcctg tacaacgagc gtgttggcgc ttgtactctg     780
gttgctgccg acagtgaaac cgttgatcgc gcattcagcc aaatgaaagc ggcgattcgc     840
gctaactact ctaacccacc agcacacggc gcttctgttg ttgccaccat cctgagcaac     900
gatgcgttac gtgcgatttg gaacaagag ctgactgata tgcgccagcg tattcagcgt     960
atgcgtcagt tgttcgtcaa tacgctgcag gaaaaaggcg caaaccgcga cttcagcttt    1020
atcatcaaac agaacggcat gttctccttc agtggcctga caaagaaca gtgctgcgt     1080
ctgcgcgaag agtttggcgt atatgcggtt gcttctggtc gcgtaaatgt ggccgggatg    1140
acaccagata acatggctcc gctgtgcgaa gcgattgtgg cagtgctgta a             1191
```

```
<210> SEQ ID NO 27
<211> LENGTH: 396
<212> TYPE: PRT
<213> ORGANISM: Escherichia coli

<400> SEQUENCE: 27
```

| | | | | | | | | | | | | | | | |
|---|---|---|---|---|---|---|---|---|---|---|---|---|---|---|---|
| Met | Phe | Glu | Asn | Ile | Thr | Ala | Ala | Pro | Ala | Asp | Pro | Ile | Leu | Gly | Leu |
| 1 | | | | 5 | | | | | 10 | | | | | 15 | |
| Ala | Asp | Leu | Phe | Arg | Ala | Asp | Glu | Arg | Pro | Gly | Lys | Ile | Asn | Leu | Gly |
| | | | 20 | | | | | 25 | | | | | 30 | | |
| Ile | Gly | Val | Tyr | Lys | Asp | Glu | Thr | Gly | Lys | Thr | Pro | Val | Leu | Thr | Ser |
| | | | 35 | | | | 40 | | | | | 45 | | | |
| Val | Lys | Lys | Ala | Glu | Gln | Tyr | Leu | Leu | Glu | Asn | Glu | Thr | Thr | Lys | Asn |
| 50 | | | | | 55 | | | | | 60 | | | | | |
| Tyr | Leu | Gly | Ile | Asp | Gly | Ile | Pro | Glu | Phe | Gly | Arg | Cys | Thr | Gln | Glu |
| 65 | | | | 70 | | | | | 75 | | | | | 80 | |
| Leu | Leu | Phe | Gly | Lys | Gly | Ser | Ala | Leu | Ile | Asn | Asp | Lys | Arg | Ala | Arg |
| | | | | 85 | | | | | 90 | | | | | 95 | |
| Thr | Ala | Gln | Thr | Pro | Gly | Gly | Thr | Gly | Ala | Leu | Arg | Val | Ala | Ala | Asp |
| | | | | 100 | | | | | 105 | | | | | 110 | |
| Phe | Leu | Ala | Lys | Asn | Thr | Ser | Val | Lys | Arg | Val | Trp | Val | Ser | Asn | Pro |
| | | | 115 | | | | | 120 | | | | | 125 | | |
| Ser | Trp | Pro | Asn | His | Lys | Ser | Val | Phe | Asn | Ser | Ala | Gly | Leu | Glu | Val |
| | 130 | | | | | 135 | | | | | 140 | | | | |
| Arg | Glu | Tyr | Ala | Tyr | Tyr | Asp | Ala | Glu | Asn | His | Thr | Leu | Asp | Phe | Asp |
| 145 | | | | | 150 | | | | | 155 | | | | | 160 |
| Ala | Leu | Ile | Asn | Ser | Leu | Asn | Glu | Ala | Gln | Ala | Gly | Asp | Val | Val | Leu |
| | | | | 165 | | | | | 170 | | | | | 175 | |
| Phe | His | Gly | Cys | Cys | His | Asn | Pro | Thr | Gly | Ile | Asp | Pro | Thr | Leu | Glu |
| | | | 180 | | | | | 185 | | | | | 190 | | |
| Gln | Trp | Gln | Thr | Leu | Ala | Gln | Leu | Ser | Val | Glu | Lys | Gly | Trp | Leu | Pro |
| | | 195 | | | | | 200 | | | | | 205 | | | |
| Leu | Phe | Asp | Phe | Ala | Tyr | Gln | Gly | Phe | Ala | Arg | Gly | Leu | Glu | Glu | Asp |
| 210 | | | | | 215 | | | | | 220 | | | | | |
| Ala | Glu | Gly | Leu | Arg | Ala | Phe | Ala | Ala | Met | His | Lys | Glu | Leu | Ile | Val |
| 225 | | | | | 230 | | | | | 235 | | | | | 240 |
| Ala | Ser | Ser | Tyr | Ser | Lys | Asn | Phe | Gly | Leu | Tyr | Asn | Glu | Arg | Val | Gly |
| | | | | 245 | | | | | 250 | | | | | 255 | |
| Ala | Cys | Thr | Leu | Val | Ala | Ala | Asp | Ser | Glu | Thr | Val | Asp | Arg | Ala | Phe |
| | | | 260 | | | | | 265 | | | | | 270 | | |
| Ser | Gln | Met | Lys | Ala | Ala | Ile | Arg | Ala | Asn | Tyr | Ser | Asn | Pro | Pro | Ala |
| | | 275 | | | | | 280 | | | | | 285 | | | |
| His | Gly | Ala | Ser | Val | Val | Ala | Thr | Ile | Leu | Ser | Asn | Asp | Ala | Leu | Arg |
| | 290 | | | | | 295 | | | | | 300 | | | | |
| Ala | Ile | Trp | Glu | Gln | Glu | Leu | Thr | Asp | Met | Arg | Gln | Arg | Ile | Gln | Arg |
| 305 | | | | | 310 | | | | | 315 | | | | | 320 |
| Met | Arg | Gln | Leu | Phe | Val | Asn | Thr | Leu | Gln | Glu | Lys | Gly | Ala | Asn | Arg |
| | | | | 325 | | | | | 330 | | | | | 335 | |
| Asp | Phe | Ser | Phe | Ile | Ile | Lys | Gln | Asn | Gly | Met | Phe | Ser | Phe | Ser | Gly |
| | | | 340 | | | | | 345 | | | | | 350 | | |
| Leu | Thr | Lys | Glu | Gln | Val | Leu | Arg | Leu | Arg | Glu | Glu | Phe | Gly | Val | Tyr |
| | | 355 | | | | | 360 | | | | | 365 | | | |
| Ala | Val | Ala | Ser | Gly | Arg | Val | Asn | Val | Ala | Gly | Met | Thr | Pro | Asp | Asn |
| 370 | | | | | 375 | | | | | 380 | | | | | |

```
Met Ala Pro Leu Cys Glu Ala Ile Val Ala Val Leu
385                 390                 395
```

```
<210> SEQ ID NO 28
<211> LENGTH: 240
<212> TYPE: PRT
<213> ORGANISM: Pseudomonas aeruginosa

<400> SEQUENCE: 28
```

```
Ala Asp Val Val Arg Gly Leu Asp Asn Gly Glu Phe Glu Ala Tyr Tyr
1               5                   10                  15

Gln Pro Lys Val Ala Leu Asp Gly Gly Leu Ile Gly Ala Glu Val
            20                  25                  30

Leu Ala Arg Trp Asn His Pro His Leu Gly Val Leu Pro Pro Ser His
        35                  40                  45

Phe Leu Tyr Val Met Glu Thr Tyr Asn Leu Val Asp Lys Leu Phe Trp
50                  55                  60

Gln Leu Phe Ser Gln Gly Leu Ala Thr Arg Arg Lys Leu Ala Gln Leu
65                  70                  75                  80

Gly Gln Pro Ile Asn Leu Ala Phe Asn Val His Pro Ser Gln Leu Gly
                85                  90                  95

Ser Arg Ala Leu Ala Glu Asn Ile Ser Ala Leu Leu Thr Glu Phe His
            100                 105                 110

Leu Pro Pro Ser Ser Val Met Phe Glu Ile Thr Glu Thr Gly Leu Ile
            115                 120                 125

Ser Ala Pro Ala Ser Ser Leu Glu Asn Leu Val Arg Leu Arg Ile Met
        130                 135                 140

Gly Cys Gly Leu Ala Met Asp Asp Phe Gly Ala Gly Tyr Ser Ser Leu
145                 150                 155                 160

Asp Arg Leu Cys Glu Phe Pro Phe Ser Gln Ile Lys Leu Asp Arg Thr
                165                 170                 175

Phe Val Gln Lys Met Lys Thr Gln Pro Arg Ser Cys Ala Val Ile Ser
            180                 185                 190

Ser Val Val Ala Leu Ala Gln Ala Leu Gly Ile Ser Leu Val Val Glu
        195                 200                 205

Gly Val Glu Ser Asp Glu Gln Arg Val Arg Leu Ile Glu Leu Gly Cys
    210                 215                 220

Ser Ile Ala Gln Gly Tyr Leu Phe Ala Arg Pro Met Pro Glu Gln His
225                 230                 235                 240
```

```
<210> SEQ ID NO 29
<211> LENGTH: 235
<212> TYPE: PRT
<213> ORGANISM: Vibrio cholerae

<400> SEQUENCE: 29
```

```
Glu Ile Glu Gln Ala Phe Leu His Asp His Ile Phe Asn Tyr Tyr Gln
1               5                   10                  15

Pro Gln Phe Asp Phe Arg Ser Gly Ala Met Val Gly Val Glu Ala Leu
            20                  25                  30

Val Arg Tyr Glu His Pro Thr His Gly Met Leu Ser Pro Ala Val Phe
        35                  40                  45

Leu Pro Leu Ile Glu Gln Cys Gly Leu His Glu Lys Leu Phe Leu Thr
50                  55                  60

Val Leu Glu Lys Ser Val Ser Leu Ala Ser Ile Gly Ala Asp Leu
65                  70                  75                  80
```

```
Gln Leu Ser Val Asn Ile Ser Gln Arg Asn Leu Gln His Ser Ile Cys
                85                  90                  95

Asp Pro Ile Leu Ala Ile Cys Glu Arg Tyr Gly Phe Pro Ala Ser Lys
            100                 105                 110

Leu Thr Leu Glu Met Thr Glu His Glu Val Tyr Asn Gly Thr Pro Thr
        115                 120                 125

Ser Leu Ala Asn Leu Ala Arg Leu Arg Met Tyr Gly Val Gly Leu Ser
    130                 135                 140

Ile Asp Asp Phe Gly Thr Gly Tyr Ala Ser Leu Gly Gln Leu Ala Gln
145                 150                 155                 160

Leu Pro Phe Thr Glu Leu Lys Ile Asp Arg Ser Phe Val His Asp Leu
                165                 170                 175

Ala Thr Asn Tyr Lys His Gln Gln Leu Thr Asn Met Cys Leu Leu Leu
            180                 185                 190

Ala Gln Ser Leu Gly Leu His Cys Val Val Glu Gly Val Glu Asn Glu
        195                 200                 205

Glu Thr Trp Gln Tyr Leu Arg Gln Leu Gly Val Asp Thr Cys Gln Gly
    210                 215                 220

Tyr Tyr Ala Ala Lys Pro Met Pro Ile Ala Gln
225                 230                 235

<210> SEQ ID NO 30
<211> LENGTH: 238
<212> TYPE: PRT
<213> ORGANISM: Escherichia coli

<400> SEQUENCE: 30

Glu Ala Ile Ser Leu Ala Leu Glu Asn His Glu Phe Lys Pro Trp Ile
1               5                   10                  15

Gln Pro Val Phe Cys Ala Gln Thr Gly Val Leu Thr Gly Cys Glu Val
            20                  25                  30

Leu Val Arg Trp Glu His Pro Gln Thr Gly Ile Ile Pro Pro Asp Gln
        35                  40                  45

Phe Ile Pro Leu Ala Glu Ser Ser Gly Leu Ile Val Ile Met Thr Arg
    50                  55                  60

Gln Leu Met Lys Gln Thr Ala Asp Ile Leu Met Pro Val Lys His Leu
65                  70                  75                  80

Leu Pro Asp Asn Phe His Ile Gly Ile Asn Val Ser Ala Gly Cys Phe
                85                  90                  95

Leu Ala Ala Gly Phe Glu Lys Glu Cys Leu Asn Leu Val Lys Lys Leu
            100                 105                 110

Gly Asn Asp Lys Ile Lys Leu Val Leu Glu Leu Thr Glu Arg Asn Pro
        115                 120                 125

Ile Pro Val Thr Pro Glu Ala Arg Ala Ile Phe Asp Ser Leu His Gln
    130                 135                 140

His Asn Ile Thr Phe Ala Leu Asp Asp Phe Gly Thr Gly Tyr Ala Thr
145                 150                 155                 160

Tyr Arg Tyr Leu Gln Ala Phe Pro Val Asp Phe Ile Lys Ile Asp Lys
                165                 170                 175

Ser Phe Val Gln Met Ala Ser Val Asp Glu Ile Ser Gly His Ile Val
            180                 185                 190

Asp Asn Ile Val Glu Leu Ala Arg Lys Pro Gly Leu Ser Ile Val Ala
        195                 200                 205

Glu Gly Val Glu Thr Gln Glu Gln Ala Asp Leu Met Ile Gly Lys Gly
    210                 215                 220
```

```
Val His Phe Leu Gln Gly Tyr Leu Tyr Ser Pro Pro Val Pro
225                 230                 235

<210> SEQ ID NO 31
<211> LENGTH: 240
<212> TYPE: PRT
<213> ORGANISM: Pseudomonas aeruginosa

<400> SEQUENCE: 31

Asp Leu Arg Asp Ala Leu Gln Arg His Glu Leu His Leu Val Tyr Gln
1               5                   10                  15

Pro Gln Val Asp Tyr Arg Asp His Arg Val Val Gly Val Glu Ala Leu
            20                  25                  30

Leu Arg Trp Gln His Pro Leu His Gly Phe Val Pro Pro Asp Leu Phe
        35                  40                  45

Ile Pro Leu Ala Glu Gln Asn Gly Ser Ile Phe Ser Ile Gly Glu Trp
    50                  55                  60

Val Leu Asp Gln Ala Cys Arg Gln Leu Arg Glu Trp His Asp Gln Gly
65                  70                  75                  80

Phe Asp Asp Leu Arg Met Ala Val Asn Leu Ser Thr Val Gln Leu His
                85                  90                  95

His Asn Ala Leu Pro Arg Val Val Ser Asn Leu Leu Gln Val Tyr Arg
            100                 105                 110

Leu Pro Ala Arg Ser Leu Glu Leu Glu Val Thr Glu Thr Gly Leu Met
        115                 120                 125

Glu Asp Ile Ser Thr Ala Ala Gln His Leu Leu Ser Leu Arg Arg Ala
130                 135                 140

Gly Ala Leu Ile Ala Ile Asp Asp Phe Gly Thr Gly Tyr Ser Ser Leu
145                 150                 155                 160

Ser Tyr Leu Lys Ser Leu Pro Leu Asp Lys Ile Lys Ile Asp Lys Ser
                165                 170                 175

Phe Val Gln Asp Leu Leu Gln Asp Glu Asp Ala Thr Ile Val Arg
            180                 185                 190

Ala Ile Ile Gln Leu Gly Lys Ser Leu Gly Met Gln Val Ile Ala Glu
        195                 200                 205

Gly Val Glu Thr Ala Glu Gln Glu Ala Tyr Ile Ile Ala Glu Gly Cys
    210                 215                 220

Asn Glu Gly Gln Gly Tyr Leu Tyr Ser Lys Pro Leu Pro Ala Arg Glu
225                 230                 235                 240

<210> SEQ ID NO 32
<211> LENGTH: 257
<212> TYPE: PRT
<213> ORGANISM: Ralstonia eutropha

<400> SEQUENCE: 32

Met Arg Gly Ser His His His His His His Gly Ser Thr Gln Arg Ile
1               5                   10                  15

Ala Tyr Val Thr Gly Gly Met Gly Gly Ile Gly Thr Ala Ile Cys Gln
            20                  25                  30

Arg Leu Ala Lys Asp Gly Phe Arg Val Val Ala Gly Cys Gly Pro Asn
        35                  40                  45

Ser Pro Arg Arg Glu Lys Trp Leu Glu Gln Gln Lys Ala Leu Gly Phe
    50                  55                  60

Asp Phe Ile Ala Ser Glu Gly Asn Val Ala Asp Trp Asp Ser Thr Lys
65                  70                  75                  80
```

```
Thr Ala Phe Asp Lys Val Lys Ser Glu Val Gly Glu Val Asp Val Leu
                85                  90                  95

Ile Asn Asn Ala Gly Ile Thr Arg Asp Val Val Phe Arg Lys Met Thr
            100                 105                 110

Arg Ala Asp Trp Asp Ala Val Ile Asp Thr Asn Leu Thr Ser Leu Phe
        115                 120                 125

Asn Val Thr Lys Gln Val Ile Asp Gly Met Ala Asp Arg Gly Trp Gly
    130                 135                 140

Arg Ile Val Asn Ile Ser Ser Val Asn Gly Gln Lys Gly Gln Phe Gly
145                 150                 155                 160

Gln Thr Asn Tyr Ser Thr Ala Lys Ala Gly Leu His Gly Phe Thr Met
                165                 170                 175

Ala Leu Ala Gln Glu Val Ala Thr Lys Gly Val Thr Val Asn Thr Val
            180                 185                 190

Ser Pro Gly Tyr Ile Ala Thr Asp Met Val Lys Ala Ile Arg Gln Asp
        195                 200                 205

Val Leu Asp Lys Ile Val Ala Thr Ile Pro Val Lys Arg Leu Gly Leu
    210                 215                 220

Pro Glu Glu Ile Ala Ser Ile Cys Ala Trp Leu Ser Ser Glu Glu Ser
225                 230                 235                 240

Gly Phe Ser Thr Gly Ala Asp Phe Ser Leu Asn Gly Gly Leu His Met
                245                 250                 255

Gly

<210> SEQ ID NO 33
<211> LENGTH: 269
<212> TYPE: PRT
<213> ORGANISM: Synechoccus elongatus

<400> SEQUENCE: 33

Met Gly Ser Ser His His His His His His Ser Ser Gly Leu Val Pro
1               5                   10                  15

Arg Gly Ser His Met Thr Ala Leu Pro Leu Thr Asp Arg Ile Ala Leu
            20                  25                  30

Val Thr Gly Ala Ser Arg Gly Ile Gly Arg Ala Ile Ala Leu Glu Leu
        35                  40                  45

Ala Ala Ala Gly Ala Lys Val Ala Val Asn Tyr Ala Ser Ser Ala Gly
    50                  55                  60

Ala Ala Asp Glu Val Val Ala Ile Ala Ala Gly Gly Glu Ala
65                  70                  75                  80

Phe Ala Val Lys Ala Asp Val Ser Gln Glu Ser Glu Val Glu Ala Leu
                85                  90                  95

Phe Ala Ala Val Ile Glu Arg Trp Gly Arg Leu Asp Val Leu Val Asn
            100                 105                 110

Asn Ala Gly Ile Thr Arg Asp Thr Leu Leu Leu Arg Met Lys Arg Asp
        115                 120                 125

Asp Trp Gln Ser Val Leu Asp Leu Asn Leu Gly Gly Val Phe Leu Cys
    130                 135                 140

Ser Arg Ala Ala Ala Lys Ile Met Leu Lys Gln Arg Ser Gly Arg Ile
145                 150                 155                 160

Ile Asn Ile Ala Ser Val Val Gly Glu Met Gly Asn Pro Gly Gln Ala
                165                 170                 175

Asn Tyr Ser Ala Ala Lys Ala Gly Val Ile Gly Leu Thr Lys Thr Val
            180                 185                 190
```

```
Ala Lys Glu Leu Ala Ser Arg Gly Ile Thr Val Asn Ala Val Ala Pro
        195                 200                 205

Gly Phe Ile Ala Thr Asp Met Thr Ser Glu Leu Ala Ala Glu Lys Leu
    210                 215                 220

Leu Glu Val Ile Pro Leu Gly Arg Tyr Gly Glu Ala Ala Glu Val Ala
225                 230                 235                 240

Gly Val Val Arg Phe Leu Ala Ala Asp Pro Ala Ala Tyr Ile Thr
                245                 250                 255

Gly Gln Val Ile Asn Ile Asp Gly Gly Leu Val Met Ala
                260                 265

<210> SEQ ID NO 34
<211> LENGTH: 246
<212> TYPE: PRT
<213> ORGANISM: Bacillus subtilis

<400> SEQUENCE: 34

Met Leu Asn Asp Lys Thr Ala Ile Val Thr Gly Ala Ser Arg Gly Ile
1               5                   10                  15

Gly Arg Ser Ile Ala Leu Asp Leu Ala Lys Ser Gly Ala Asn Val Val
            20                  25                  30

Val Asn Tyr Ser Gly Asn Glu Ala Lys Ala Asn Glu Val Val Asp Glu
        35                  40                  45

Ile Lys Ser Met Gly Arg Lys Ala Ile Ala Val Lys Ala Asp Val Ser
    50                  55                  60

Asn Pro Glu Asp Val Gln Asn Met Ile Lys Glu Thr Leu Ser Val Phe
65                  70                  75                  80

Ser Thr Ile Asp Ile Leu Val Asn Asn Ala Gly Ile Thr Arg Asp Asn
                85                  90                  95

Leu Ile Met Arg Met Lys Glu Asp Glu Trp Asp Asp Val Ile Asn Ile
            100                 105                 110

Asn Leu Lys Gly Val Phe Asn Cys Thr Lys Ala Val Thr Arg Gln Met
        115                 120                 125

Met Lys Gln Arg Ser Gly Arg Ile Ile Asn Val Ser Ser Ile Val Gly
    130                 135                 140

Val Ser Gly Asn Pro Gly Gln Ala Asn Tyr Val Ala Ala Lys Ala Gly
145                 150                 155                 160

Val Ile Gly Leu Thr Lys Ser Ser Ala Lys Glu Leu Ala Ser Arg Asn
                165                 170                 175

Ile Thr Val Asn Ala Ile Ala Pro Gly Phe Ile Ser Thr Asp Met Thr
            180                 185                 190

Asp Lys Leu Ala Lys Asp Val Gln Asp Glu Met Leu Lys Gln Ile Pro
        195                 200                 205

Leu Ala Arg Phe Gly Glu Pro Ser Asp Val Ser Ser Val Val Thr Phe
    210                 215                 220

Leu Ala Ser Glu Gly Ala Arg Tyr Met Thr Gly Gln Thr Leu His Ile
225                 230                 235                 240

Asp Gly Gly Met Val Met
                245

<210> SEQ ID NO 35
<211> LENGTH: 52
<212> TYPE: DNA
<213> ORGANISM: Artificial Sequence
<220> FEATURE:
<223> OTHER INFORMATION: cadA-F
```

<400> SEQUENCE: 35
ggcgagctca cacaggaaac agaccatgaa cgttattgca atattgaatc ac        52

<210> SEQ ID NO 36
<211> LENGTH: 28
<212> TYPE: DNA
<213> ORGANISM: Artificial Sequence
<220> FEATURE:
<223> OTHER INFORMATION: cadA-R

<400> SEQUENCE: 36
ggctctagac cacttccctt gtacgagc        28

<210> SEQ ID NO 37
<211> LENGTH: 44
<212> TYPE: DNA
<213> ORGANISM: Artificial Sequence
<220> FEATURE:
<223> OTHER INFORMATION: cadA-F2

<400> SEQUENCE: 37
atttcacaca ggaaacagct atgaacgtta ttgcaatatt gaat        44

<210> SEQ ID NO 38
<211> LENGTH: 20
<212> TYPE: DNA
<213> ORGANISM: Artificial Sequence
<220> FEATURE:
<223> OTHER INFORMATION: cadA-R2

<400> SEQUENCE: 38
agctgttccc tgtgtgaaat        20

<210> SEQ ID NO 39
<211> LENGTH: 32
<212> TYPE: DNA
<213> ORGANISM: Artificial Sequence
<220> FEATURE:
<223> OTHER INFORMATION: bdcA-F

<400> SEQUENCE: 39
ggcgagctct aaatcaagga gtccttatgg gc        32

<210> SEQ ID NO 40
<211> LENGTH: 32
<212> TYPE: DNA
<213> ORGANISM: Artificial Sequence
<220> FEATURE:
<223> OTHER INFORMATION: bdcA-R

<400> SEQUENCE: 40
ggctctagag cttaattgag cgtagtcggt ta        32

<210> SEQ ID NO 41
<211> LENGTH: 41
<212> TYPE: DNA
<213> ORGANISM: Artificial Sequence
<220> FEATURE:
<223> OTHER INFORMATION: bdcA-F2

<400> SEQUENCE: 41
atttcacaca ggaaacagct atgggcgctt ttacaggtaa g        41

<210> SEQ ID NO 42

```
<211> LENGTH: 20
<212> TYPE: DNA
<213> ORGANISM: Artificial Sequence
<220> FEATURE:
<223> OTHER INFORMATION: bdcA-R2

<400> SEQUENCE: 42
agctgtttcc tgtgtgaaat                                          20

<210> SEQ ID NO 43
<211> LENGTH: 46
<212> TYPE: DNA
<213> ORGANISM: Artificial Sequence
<220> FEATURE:
<223> OTHER INFORMATION: bdcA-F3

<400> SEQUENCE: 43
ggctctagaa cacaggaaac agaccatggg cgcttttaca ggtaag             46

<210> SEQ ID NO 44
<211> LENGTH: 31
<212> TYPE: DNA
<213> ORGANISM: Artificial Sequence
<220> FEATURE:
<223> OTHER INFORMATION: bdcA-R3

<400> SEQUENCE: 44
ggcaagcttg cttaattgag cgtagtcggt t                             31

<210> SEQ ID NO 45
<211> LENGTH: 45
<212> TYPE: DNA
<213> ORGANISM: Artificial Sequence
<220> FEATURE:
<223> OTHER INFORMATION: yahA-F

<400> SEQUENCE: 45
ggcgagctcc cataggtaga agtatgaatt catgtgattt tcgtg              45

<210> SEQ ID NO 46
<211> LENGTH: 29
<212> TYPE: DNA
<213> ORGANISM: Artificial Sequence
<220> FEATURE:
<223> OTHER INFORMATION: yahA-R

<400> SEQUENCE: 46
ggctctagat caaccacctg ctttcatta                                29

<210> SEQ ID NO 47
<211> LENGTH: 42
<212> TYPE: DNA
<213> ORGANISM: Artificial Sequence
<220> FEATURE:
<223> OTHER INFORMATION: yahA-F2

<400> SEQUENCE: 47
atttcacaca ggaaacagct atgaattcat gtgattttcg tg                 42

<210> SEQ ID NO 48
<211> LENGTH: 20
<212> TYPE: DNA
<213> ORGANISM: Artificial Sequence
<220> FEATURE:
<223> OTHER INFORMATION: yahA-R2

<400> SEQUENCE: 48
```

-continued agctgtttcc tgtgtgaaat                                              20

<210> SEQ ID NO 49
<211> LENGTH: 47
<212> TYPE: DNA
<213> ORGANISM: Artificial Sequence
<220> FEATURE:
<223> OTHER INFORMATION: yahA-F3

<400> SEQUENCE: 49
ggctctagaa cacaggaaac agaccatgaa ttcatgtgat tttcgtg                47

<210> SEQ ID NO 50
<211> LENGTH: 29
<212> TYPE: DNA
<213> ORGANISM: Artificial Sequence
<220> FEATURE:
<223> OTHER INFORMATION: yahA-R3

<400> SEQUENCE: 50
ggcaagcttt caaccacctg ctttcatta                                    29

<210> SEQ ID NO 51
<211> LENGTH: 66
<212> TYPE: DNA
<213> ORGANISM: Artificial Sequence
<220> FEATURE:
<223> OTHER INFORMATION: psyn-1

<400> SEQUENCE: 51
ggcgaattca gtttattctt gacatgtagt gaggggggctg gtataatgag ctcggtaccc 60
ggggat                                                             66

<210> SEQ ID NO 52
<211> LENGTH: 34
<212> TYPE: DNA
<213> ORGANISM: Artificial Sequence
<220> FEATURE:
<223> OTHER INFORMATION: psyn-2

<400> SEQUENCE: 52
ggcagtactc aaccaagtca ttctgagaat agtg                              34

<210> SEQ ID NO 53
<211> LENGTH: 49
<212> TYPE: DNA
<213> ORGANISM: Artificial Sequence
<220> FEATURE:
<223> OTHER INFORMATION: tetA-F

<400> SEQUENCE: 53
ggcgagctca cacaggaaac agaccatgaa atctaacaat gcgctcatc              49

<210> SEQ ID NO 54
<211> LENGTH: 29
<212> TYPE: DNA
<213> ORGANISM: Artificial Sequence
<220> FEATURE:
<223> OTHER INFORMATION: tetA-R

<400> SEQUENCE: 54
ggctctagat caacgacagg agcacgatc                                    29

<210> SEQ ID NO 55

```
<211> LENGTH: 46
<212> TYPE: DNA
<213> ORGANISM: Artificial Sequence
<220> FEATURE:
<223> OTHER INFORMATION: lysC-F

<400> SEQUENCE: 55
ggcgagctca cacaggaaac agaccatgtc tgaaattgtt gtctcc          46

<210> SEQ ID NO 56
<211> LENGTH: 33
<212> TYPE: DNA
<213> ORGANISM: Artificial Sequence
<220> FEATURE:
<223> OTHER INFORMATION: lysC-R

<400> SEQUENCE: 56
ggcggatcct tactcaaaca aattactatg cag                        33

<210> SEQ ID NO 57
<211> LENGTH: 46
<212> TYPE: DNA
<213> ORGANISM: Artificial Sequence
<220> FEATURE:
<223> OTHER INFORMATION: dapA-F

<400> SEQUENCE: 57
ggcggatcca cacaggaaac agaccatgtt cacgggaagt attgtc          46

<210> SEQ ID NO 58
<211> LENGTH: 28
<212> TYPE: DNA
<213> ORGANISM: Artificial Sequence
<220> FEATURE:
<223> OTHER INFORMATION: dapA-R

<400> SEQUENCE: 58
ggctctagat tacagcaaac cggcatgc                              28

<210> SEQ ID NO 59
<211> LENGTH: 46
<212> TYPE: DNA
<213> ORGANISM: Artificial Sequence
<220> FEATURE:
<223> OTHER INFORMATION: lysA-F

<400> SEQUENCE: 59
ggctctagaa cacaggaaac agaccatgcc acattcactg ttcagc          46

<210> SEQ ID NO 60
<211> LENGTH: 30
<212> TYPE: DNA
<213> ORGANISM: Artificial Sequence
<220> FEATURE:
<223> OTHER INFORMATION: lysA-R

<400> SEQUENCE: 60
ggcgtcgact taaagcaatt ccagcgccag                            30

<210> SEQ ID NO 61
<211> LENGTH: 34
<212> TYPE: DNA
<213> ORGANISM: Artificial Sequence
<220> FEATURE:
<223> OTHER INFORMATION: tetA-F3

<400> SEQUENCE: 61
```

```
ggcctcgaga gtttattctt gacatgtagt gagg                                     34

<210> SEQ ID NO 62
<211> LENGTH: 29
<212> TYPE: DNA
<213> ORGANISM: Artificial Sequence
<220> FEATURE:
<223> OTHER INFORMATION: tetA-R3

<400> SEQUENCE: 62
ggcgcatgct caacgacagg agcacgatc                                           29

<210> SEQ ID NO 63
<211> LENGTH: 23
<212> TYPE: DNA
<213> ORGANISM: Artificial Sequence
<220> FEATURE:
<223> OTHER INFORMATION: 318-F

<400> SEQUENCE: 63
cagcctgaat atactgcatt ctc                                                 23

<210> SEQ ID NO 64
<211> LENGTH: 23
<212> TYPE: DNA
<213> ORGANISM: Artificial Sequence
<220> FEATURE:
<223> OTHER INFORMATION: 318-R

<400> SEQUENCE: 64
gagaatgcag tatattcagg ctg                                                 23

<210> SEQ ID NO 65
<211> LENGTH: 20
<212> TYPE: DNA
<213> ORGANISM: Artificial Sequence
<220> FEATURE:
<223> OTHER INFORMATION: 323-F

<400> SEQUENCE: 65
gcattctcgc gatttcctcg                                                     20

<210> SEQ ID NO 66
<211> LENGTH: 20
<212> TYPE: DNA
<213> ORGANISM: Artificial Sequence
<220> FEATURE:
<223> OTHER INFORMATION: 323-R

<400> SEQUENCE: 66
cgaggaaatc gcgagaatgc                                                     20

<210> SEQ ID NO 67
<211> LENGTH: 46
<212> TYPE: DNA
<213> ORGANISM: Artificial Sequence
<220> FEATURE:
<223> OTHER INFORMATION: SlysC-F

<400> SEQUENCE: 67
ggcgagctca cacaggaaac agaccatggg cttagttgtg cagaaa                        46

<210> SEQ ID NO 68
<211> LENGTH: 30
<212> TYPE: DNA
```

```
<213> ORGANISM: Artificial Sequence
<220> FEATURE:
<223> OTHER INFORMATION: SlysC-R

<400> SEQUENCE: 68
ggcggatcct taacgacctg tgccgccata                                30

<210> SEQ ID NO 69
<211> LENGTH: 48
<212> TYPE: DNA
<213> ORGANISM: Artificial Sequence
<220> FEATURE:
<223> OTHER INFORMATION: asd-F

<400> SEQUENCE: 69
ggcgagctca cacaggaaac agaccatgaa aaatgttggt tttatcgg             48

<210> SEQ ID NO 70
<211> LENGTH: 28
<212> TYPE: DNA
<213> ORGANISM: Artificial Sequence
<220> FEATURE:
<223> OTHER INFORMATION: asd-R

<400> SEQUENCE: 70
ggcggatcct tacgccagtt gacgaagc                                  28

<210> SEQ ID NO 71
<211> LENGTH: 39
<212> TYPE: DNA
<213> ORGANISM: Artificial Sequence
<220> FEATURE:
<223> OTHER INFORMATION: dapB-F

<400> SEQUENCE: 71
ggcacacagg aaacagacca tgcatgatgc aaacatccg                      39

<210> SEQ ID NO 72
<211> LENGTH: 38
<212> TYPE: DNA
<213> ORGANISM: Artificial Sequence
<220> FEATURE:
<223> OTHER INFORMATION: dapB-R

<400> SEQUENCE: 72
ggctctagat tacaaattat tgagatcaag tacatctc                       38

<210> SEQ ID NO 73
<211> LENGTH: 45
<212> TYPE: DNA
<213> ORGANISM: Artificial Sequence
<220> FEATURE:
<223> OTHER INFORMATION: dapD-F

<400> SEQUENCE: 73
ggctctagaa cacaggaaac agaccatgca gcagttacag aacat               45

<210> SEQ ID NO 74
<211> LENGTH: 29
<212> TYPE: DNA
<213> ORGANISM: Artificial Sequence
<220> FEATURE:
<223> OTHER INFORMATION: dapD-R

<400> SEQUENCE: 74
ggcgcatgct tagtcgatgg tacgcagca                                 29
```

<210> SEQ ID NO 75
<211> LENGTH: 46
<212> TYPE: DNA
<213> ORGANISM: Artificial Sequence
<220> FEATURE:
<223> OTHER INFORMATION: aspC-F

<400> SEQUENCE: 75
ggctctagaa cacaggaaac agaccatgtt tgagaacatt accgcc       46

<210> SEQ ID NO 76
<211> LENGTH: 47
<212> TYPE: DNA
<213> ORGANISM: Artificial Sequence
<220> FEATURE:
<223> OTHER INFORMATION: aspC-R

<400> SEQUENCE: 76
ggcgcatgcg acctcgaggt agtcgactta cagcactgcc acaatcg      47

<210> SEQ ID NO 77
<211> LENGTH: 34
<212> TYPE: DNA
<213> ORGANISM: Artificial Sequence
<220> FEATURE:
<223> OTHER INFORMATION: LAL-F

<400> SEQUENCE: 77
ggcggtacca gtttattctt gacatgtagt gagg       34

<210> SEQ ID NO 78
<211> LENGTH: 29
<212> TYPE: DNA
<213> ORGANISM: Artificial Sequence
<220> FEATURE:
<223> OTHER INFORMATION: LAL-R

<400> SEQUENCE: 78
ggcgggccct taaagcaatt ccagcgcca       29

<210> SEQ ID NO 79
<211> LENGTH: 29
<212> TYPE: DNA
<213> ORGANISM: Artificial Sequence
<220> FEATURE:
<223> OTHER INFORMATION: ABC-F

<400> SEQUENCE: 79
ggcgggccct gctggccttt tgctcacat       29

<210> SEQ ID NO 80
<211> LENGTH: 29
<212> TYPE: DNA
<213> ORGANISM: Artificial Sequence
<220> FEATURE:
<223> OTHER INFORMATION: ABCT-R

<400> SEQUENCE: 80
ggcggtacct caacgacagg agcacgatc       29

<210> SEQ ID NO 81
<211> LENGTH: 34
<212> TYPE: DNA
<213> ORGANISM: Artificial Sequence
<220> FEATURE:

```
<223> OTHER INFORMATION: SAL-F

<400> SEQUENCE: 81
ggcggtacca gtttattctt gacatgtagt gagg                                34

<210> SEQ ID NO 82
<211> LENGTH: 29
<212> TYPE: DNA
<213> ORGANISM: Artificial Sequence
<220> FEATURE:
<223> OTHER INFORMATION: SAL-R

<400> SEQUENCE: 82
ggcgggccct taaagcaatt ccagcgcca                                      29
```